United States Patent [19]
Maccecchini

[11] Patent Number: 6,110,894
[45] Date of Patent: Aug. 29, 2000

[54] ALLOSTERIC MODULATORS OF THE NMDA RECEPTOR AND THEIR USE IN THE TREATMENT OF CNS DISORDERS AND ENHANCEMENT OF CNS FUNCTION

[75] Inventor: Maria-Luisa Maccecchini, West Chester, Pa.

[73] Assignee: Bearsden Bio, Inc., Aston, Pa.

[21] Appl. No.: 09/146,269

[22] Filed: Sep. 3, 1998

Related U.S. Application Data

[60] Division of application No. 08/413,490, Mar. 30, 1995, Pat. No. 5,854,217, which is a continuation-in-part of application No. 08/323,436, Oct. 14, 1994, Pat. No. 5,830,998, which is a continuation-in-part of application No. 07/952,818, Sep. 28, 1992, abandoned.

[51] Int. Cl.[7] .................................................... A61K 38/04
[52] U.S. Cl. ............................................ 514/13; 530/326
[58] Field of Search ................................. 514/12, 13, 18; 530/324, 326, 330

[56] References Cited

U.S. PATENT DOCUMENTS

| | | |
|---|---|---|
| 5,051,403 | 9/1991 | Miljanich et al. . |
| 5,559,095 | 9/1996 | Miljanich et al. . |
| 5,830,908 | 11/1998 | Maccecchini . |
| 5,844,077 | 12/1998 | Saydoff . |

OTHER PUBLICATIONS

Hernandez, J.–F. et al., J. Cell Biochem. Suppl. O(14 Part C), 242, 1990, and attached presentation slide copies.

*Primary Examiner*—Marianne P. Allen
*Attorney, Agent, or Firm*—Rothwell, Figg, Ernst & Kurz, P.C.

[57] ABSTRACT

Novel compounds and compositions for modulating NMDA receptor function comprising Conantokin-G and derivatives thereof; methods for modulating NMDA receptor function and methods for treating neuropsychopharmacological disorders, using the novel compounds and compositions of the invention; and a method for screening compounds capable of binding to a novel allosteric modulatory site, are described.

2 Claims, 20 Drawing Sheets

ALLOSTERIC MODULATORS OF THE NMDA RECEPTOR AND THEIR USE IN THE TREATMENT OF CNS DISORDERS AND ENHANCEMENT OF CNS FUNCTION

This application is a divisional of U.S. application Ser. No. 08/413,490, filed Mar. 30, 1995 now U.S. Pat. No. 5,854,217, which is a continuation-in-part of U.S. application Ser. No. 08/323,436, filed Oct. 14, 1994, now U.S. Pat. No. 383,0998 which is a continuation-in-part of U.S. application Ser. No. 07/952,818, filed Sept. 28, 1992, abandoned the disclosures of which are incorporated herein by reference.

FIELD OF THE INVENTION

This invention relates to compounds and compositions which modulate the NMDA receptor and, more specifically, which modulate the receptor through a novel complex site.

BACKGROUND OF THE INVENTION

The N-methyl-D-aspartate (NMDA) receptor is a postsynaptic, ionotropic receptor which is responsive to, inter alia, the excitatory amino acids glutamate and glycine and the synthetic compound NMDA, hence the receptor name. The NMDA receptor controls the flow of both divalent ($Ca^{++}$) and monovalent ($Na^+$, $K^+$) ions into the postsynaptic neural cell through a receptor associated channel. Foster et al., "Taking apart NMDA receptors", Nature, 329:395–396, 1987; Mayer et al., "Excitatory amino acid receptors, second messengers and regulation of intracellular $Ca^{2+}$ in mammalian neurons," Trends in Pharmacol. Sci., 11:254–260, 1990.

The NMDA receptor has been implicated during development in specifying neuronal architecture and synaptic connectivity, and may be involved in experience dependent synaptic modifications. In addition, NMDA receptors are also thought to be involved in long term potentiation, Central Nervous System (CNS) plasticity, cognitive processes, memory acquisition, retention, and learning. Furthermore, the NMDA receptor has also drawn particular interest since it appears to be involved in a broad spectrum of CNS disorders.

For instance, during brain ischemia caused by stroke or traumatic injury, excessive amounts of the excitatory amino acid glutamate are released from damaged or oxygen deprived neurons. This excess glutamate binds to the NMDA receptor which opens the ligand-gated ion channel thereby allowing $Ca^{++}$ influx producing a high level of intracellular $Ca^{++}$ which activates biochemical cascades resulting in protein, DNA, and membrane degradation leading to cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures.

Neuropsychiatric involvement of the NMDA receptor has also been recognized. Blockage of the NMDA receptor $Ca^{++}$ channel by the animal anesthetic PCP (phencyclidine) produces a psychotic state in humans similar to schizophrenia (reviewed in Johnson et al., "Neuropharmacology of Phencyclidine: Basic Mechanisms and Therapeutic Potential," Annu. Rev. Pharmacol. Toxicol., 30:707–750, 1990.) Further, NMDA receptors have also been implicated in certain types of spatial learning. Bliss et al., Nature, 361:31 (1993). Interestingly, both the spatial and temporal distribution of NMDA receptors in mammalian nervous systems have been found to vary. Thus, cells may produce NMDA receptors at different times in their life cycles and not all neural cells may utilize the NMDA receptor.

Due to its broad-spectrum of neurological involvement, yet non-universal distribution, investigators have been interested in the identification and development of drugs acting at the NMDA receptor. Drugs acting on the NMDA receptor are, therefore, expected to have enormous therapeutic potential. For instance, U.S. Pat. No. 4,904,681, issued to Cordi et al. (Cordi I), describes the use of D-Cycloserine, which was known to modulate the NMDA receptor, to improve/enhance memory and to treat cognitive deficits linked to a neurological disorder. D-Cycloserine is described as a glycine agonist which binds to the strychnine-insensitive glycine receptor.

U.S. Pat. No. 5,061,721, issued to Cordi et al. (Cordi II), describes the use of a combination of D-cycloserine and D-alanine to treat Alzheimer's disease, age-associated memory impairment, learning deficits, and psychotic disorders, as well as to improve memory or learning in healthy individuals. D-alanine is administered in combination with D-Cycloserine to reduce the side effects observed in clinical trials of D-Cycloserine, mainly those due to its growth-inhibiting effect on bacteria resulting in depletion of natural intestinal flora. D-Alanine reverses the growth-inhibiting effect of D-Cycloserine on bacteria. It is also reported that D-Cycloserine actually has partial agonist character.

U.S. Pat. No. 5,086,072, issued to Trullas et al., describes the use of 1-aminocyclopropanecarboxylic acid (ACPC), which was known to modulate the NMDA receptor as a partial agonist of the strychnine-insensitive glycine binding site, to treat mood disorders including major depression, bipolar disorder, dysthymia and seasonal effective disorder. It is also therein described that ACPC mimics the actions of clinically effective antidepressants in animal models. Again, in the examples provided, the compound was administered ip. In addition, a copending U.S. patent application is cited that describes that ACPC and its derivatives may be used to treat neuropharmacological disorders resulting from excessive activation of the NMDA receptor.

None of the foregoing offers, however, a satisfactory mechanism for modulating NMDA receptor function. Since glycine is necessary for receptor function, compounds modulating the glycine site offer a limited range of control. Further, glycine displays only limited sub-type specificity and compounds modulating the glycine site are expected to behave similarly.

Development of drugs targeting the NMDA receptor, although desirous, has been hindered because the structure of the NMDA receptor has not yet been completely elucidated. It is believed to consist of several protein chains (subunits) embedded in the postsynaptic membrane. The first two subunits determined so far form a large extracellular region which probably contains most of the allosteric binding sites, several transmembrane regions looped and folded to form a pore or channel which is permeable to $Ca^{++}$, and a carboxyl terminal region with an as yet unknown function. The opening and closing of the channel is regulated by the binding of various ligands to domains of the protein residing on the extracellular surface and separate from the channel. As such, these ligands are all known as allosteric ligands. The binding of two coagonist ligands—glycine and glutamate—is thought to effect a conformational change in the overall structure of the protein which is ultimately reflected in the channel opening, partially opening, partially closing, or closing. The binding of other allosteric ligands modulates the conformational change caused or effected by glutamate and glycine.

A representation of the NMDA receptor showing schematically the principal recognition/binding sites which had been elucidated in the literature is depicted in FIG. 1. The sites marked "Glu" and "Gly" are the receptor sites for the principal excitatory amino acid neurotransmitters, glutamate and glycine. The glutamate site also selectively binds NMDA. Since the binding of glutamate and glycine has been shown to stimulate the flow of $Ca^{++}$ through the channel, glutamate and glycine are said to have a co-agonist (stimulatory) activity. Several competitive inhibitors of the actions of glutamate or glycine also bind to these sites and include those identified in the boxes in FIG. 1 labeled "NMDA Antagonists" and "Glycine Antagonists." Since these competitive inhibitors of the glutamate site block the flow of $Ca^{++}$ through the channel, they are said to have an antagonist activity. The ligand-gated ion channel of the NMDA receptor is, thus, under the control of at least two distinct allosteric sites.

Two subunits of the mouse NMDA receptor channel have been identified by cloning and expression of complementary DNAs designated NR1 and NR2. Four subtypes of NR2 have been identified: NR2a, NR2b, NR2c, and NR2d. The heteromeric NR1/NR2a, NR1/NR2b and NR1/NR2c NMDA receptor channels exhibit distinct functional properties in affinities for agonists and sensitivities to competitive antagonists and $Mg^{2+}$ block. In contrast to the wide distribution of the NR1 and NR2a subunit messenger RNAs in the brain, the NR2b subunit mRNA is expressed only in the forebrain and the NR2c subunit mRNA is found predominantly in the cerebellum. These findings suggest that the molecular diversity of the NR2 subunit family underlies the functional heterogeneity of the NMDA receptor channel. Kutsuwada et al, *Nature*, 358:36–40 (1992).

Several compounds are known which are antagonistic to the flow of cations through the NMDA receptor but which do not competitively inhibit the binding of allosteric ligands to any of the known sites. Instead, these compounds bind inside the open cation channel and are generally known as channel blockers. These are shown in FIG. 1 in the box labeled "Channel Blockers." In fact, binding of a radiolabeled form of one such channel blocker, dizocilpine (i.e., [$^3$H]MK-801), is a good measure of the activation of the NMDA receptor complex. When the channel is open, [$^3$H] MK-801 may freely pass into the channel and bind to its recognition site in the channel. Conversely, when the channel is closed, [$^3$H]MK-801 may not freely pass into the channel and bind. When the channel is partially open (partially closed) less [$^3$H]MK-801 is able to bind than when the channel is fully open.

Channel blockers such as MK-801 and antagonists are known to protect cells from excitotoxic death, but in their case the cure may be as undesirable as the death since they block any flux of $Ca^{++}$ thereby eliminating any chance of resumed normal activity. Channel blockers and glutamate site antagonists are known to cause hallucinations, high blood pressure, loss of coordination, vacuolation in the brain, learning disability and memory loss. PCP, discussed previously, produces a schizophrenic state in man.

$Mg^{++}$ and $Zn^{++}$ also modulate the NMDA receptor. The exact location of the divalent cation binding sites is still unclear. $Zn^{++}$ appears to be antagonistic to channel opening and appears to bind to an extracellular domain. $Mg^{++}$ shows a biphasic activation curve—at low concentrations, it is an agonist for NMDA receptor function and at high concentrations it is an antagonist. It appears to be absolutely necessary for proper receptor functioning and appears to bind at two sites—a voltage dependant binding site for $Mg^{++}$ within the channel and another non-voltage dependent binding site on the extracellular domain. These sites are also indicated in FIG. 1 by "$Mg^{++}$" and "$Zn^{++}$".

It is believed that the channel is in constant motion, alternating between a cation passing (open) and a cation blocking (closed) state. It is not known at present whether the allosteric modulators actually increase the time during which the channel is open to the flow of ions, or whether the modulators increase the frequency of opening. Both effects might be occurring at the same time. Thus, the terms open and close, or agonistic and antagonistic, as used herein refer to a time averaged affect.

Recently, a third class of agonists which modulate the excitatory synaptic transmission at the NMDA receptor has been identified. (Ransom et al., "Cooperative modulation of [$^3$H]MK-801 binding to the N-methyl-D-aspartate receptor-ion channel complex by L-glutamate, glycine, and polyamines," *J. Neurochem.*, 51:830–836, 1988; Reynolds et al., "Ifenprodil is a novel type of N-methyl-D-aspartate receptor antagonist: interaction with polyamines" *Molec. Pharmacol.*, 36:758–765, 1989; reviewed in Williams et al., "Modulation of the NMDA Receptor by Polyamines," *Life Sci.*, 48:469–498, 1991.) These agonists are polyamines, principally the endogenous polyamines spermine and spermidine, which bind to other extracellular allosteric sites on the NMDA receptor. In FIG. 1, the allosteric polyamine binding site is labeled "PA." The polyamines do not bind to the glutamate/NMDA site, the glycine site, or the channel blocker sites. However, polyamines do also bind inside the channel. There may be some relation between the $Mg^{++}$ binding sites and the polyamine sites, but this relationship has not yet been fully elucidated. In contrast, there is strong evidence accumulating that polyamine binding is not thought to be necessary for functioning/activation of the NMDA receptor coupled cation channel, but is necessary for maximum activation. The polyamines, thus, are allosteric modulators of the NMDA receptor.

There appears to be a broad range of polyamine (diamine, triamine, and tetraamine) compounds which will modulate the site, some of which appear to be agonists, others partial agonists, and, finally, some antagonists. Binding of the compound 1,10-diaminodecane (DA10) decreases rather than increases the channel opening. This activity has been termed "inverse agonist" activity. Such inverse agonist binds competitively at the same site as an agonist but produces the opposite effect as the agonist.

Ideally, a drug for regulating the NMDA receptor will modulate the response of one of the endogenous ligands, and not itself be an endogenous ligand. The drug must be specific, i.e., it must affect an identifiable molecular mechanism unique to target cells that bear receptors for that drug.

It is therefore an object of the present invention to provide a class of specific drugs through the discovery of a novel binding site on the NMDA receptor for a compound which is not an endogenous ligand of the receptor.

It is a further object of the present invention to provide novel compounds for regulating the flow of $Ca^{++}$ through the NMDA receptor, and compositions and methods for treating neurodegenerative disorders linked to NMDA receptor function.

SUMMARY OF THE INVENTION

Compounds, derived from the snail peptide Conantokin-G, act as allosteric modulators of the NMDA receptor cation channel and have effects ranging from inhibitory to partial modulatory to fully stimulatory on the polyamine or a closely associated modulatory site of the NMDA receptor. These compounds, therapeutic compositions, and their use for 1) treating neurological, neuropsychological, neuropsychiatric, neurodegenerative, neuropsychopharmacological and functional disorders associated with excessive or insufficient activation of the glutamate subtype of the NMDA receptor; 2) treating cognitive disorders associated with suboptimal activation or deactivation of the glutamate subtype of the NMDA receptor; and 3) improving and enhancing memory, learning, and associated mental processes, are disclosed. Examples of these disorders include acute or chronic neurodegenerative diseases, seizures, depression, anxiety, and substance addiction. The compositions can also be used to enhance learning and memory.

In one aspect, the compounds have the following formula (Formula I):

$$R^1\text{---}(A^0)_xa\text{---}[(A^1)\text{---}(A^2)\text{---}(A^3)\text{---}(A^4)\text{---}(A^5)]_m\text{---}(A^6)_xb\text{---}(A^7)_xc\text{---}[(A^8)\text{---}((A^9)\text{---}(A^{10}))_xd\text{---}NHR^2]_n \qquad (I)$$

amino terminus                                                                                                             carboxy terminus wherein
- $A^0$ is an amino acid selected from the group consisting of natural, modified, or non-natural amino acids;
- $A^1$ is an uncharged, hydrophobic amino acid;
- $A^2$, $A^3$ and $A^4$ are amino acids independently selected from glutamate, aspartic acid, γ-carboxyglutamate (Gla), 3-carboxyaspartic acid, D-glutamate, phosphoserine, or phosphothreonine;
- $A^5$ is an uncharged, hydrophobic amino acid;
- $A^6$ is a peptide chain of from about 2 to about 15 amino acids, said amino acids selected from natural, modified, or non-natural amino acids;
- $A^7$ is an amino acid selected from the group consisting of natural, modified, or non-natural amino acids;
- $A^8$ is a basic amino acid selected from lysine or arginine;
- $A^9$ and $A^{10}$ are amino acids selected from the group consisting of natural, modified, or non-natural amino acids;
- $R_1$ is H, C1–C6—CO—, -benzoyl, or -benzoyloxy;
- $R^2$ is H or C1–C6-alkyl;
- $x^a$ $x^b$, $X^c$, and $x^d$ are independently 0 or 1;
- m and n are independently 0 or 1;
- provided that m and n may not both be 0; and
- pharmaceutically acceptable salts thereof.

It is provided that the compound of Formula I cannot be $x^a$, is 0, $A^1$ is glycine, $A^2$ is glutamate, $A^3$ is γ-carboxyglutamate, $A^4$ is γ-carboxyglutamate, $A^5$ is leucine, $A^6$ is a peptide chain of 8 amino acids of the following composition Gln-Gla-Asn-Gln-Gla-Leu-Ile-Arg, $A^7$ is γ-carboxyglutamate, $A^8$ is lysine, $A^9$ is serine, $A^{10}$ is asparagine, and $R^1$ and $R^2$ are H.

It is further provided that the compound of Formula I is preferably not $x^a$ is 0, $A^1$ is glycine, $A^2$ is glutamate, $A^3$ is glutamate, $A^4$ is glutamate, $A^5$ is leucine, $A^6$ is a peptide chain of 8 amino acids of the following composition Gln-Glu-Asn-Gln-Glu-Leu-Ile-Arg, $A^7$ is glutamate, $A^8$ is lysine, $A^9$ is serine, $A^{10}$ is asparagine, and $R^1$ and $R^2$ are H.

Preferred compounds are compounds of Formula I where $A^6$ is a peptide chain consisting of from about 7 to about 9 natural and/or non-natural amino acids;
- $R^1$ is H;
- $R^2$ is H; and
- $X^a$ is 0;

and pharmaceutically acceptable salts thereof.

Further preferred compounds of formula I wherein $A_1$ and $A^5$ are amino acids selected from the group glycine, alanine, valine, leucine, or isoleucine.

More preferred compounds ate compounds of Formula I wherein:
- $A^6$ is a peptide chain consisting of about 8 natural amino acids.

Compounds preferred for their antagonistic properties are compounds of Formula I wherein n is zero.

Compounds preferred for their agonistic properties are compounds of Formula I wherein m is zero.

Specifically preferred for their modulatory activity are the following compounds:

Gly-Glu-Glu-Glu-Leu-Gln-Glu-Asn-Gln-Glu-Leu-Ile-Arg-Glu-Lys-Ser-Asn-NH$_2$ (SEQ ID NO:5);

Tyr-Gly-Glu-Glu-Glu-Leu-Gln-Glu-Asn-Gln-Glu-Leu-Ile-Arg-Glu-Lys-Ser-Asn-NH$_2$ (SEQ ID NO:6);

Ile-Arg-Glu-Lys-Ser-Asn-NH$_2$ (SEQ ID NO:7);

Glu-Glu-Glu-Leu-Gln-Glu-Asn-Gln-Glu-Leu-Ile-Arg-Glu-Lys-Ser-Asn-NH$_2$ (SEQ ID NO:10);

Gly-D-Glu-D-Glu-D-Glu-Leu-Gln-D-Glu-Asn-Gln-D-Glu-Leu-Ile-Arg-D-Glu-Lys-Ser-Asn-NH$_2$ (SEQ ID NO:11);

Gly-Glu-Ala-Gla-Leu-Gln-Gla-Asn-Gln-Gla-Leu-Ile-Arg-Gla-Lys-Ser-Asn-NH$_2$ (SEQ ID NO:22);

Gly-Glu-Ser-Gla-Leu-Gln-Gla-Asn-Gln-Gla-Leu-Ile-Arg-Gla-Lys-Ser-Asn-NH$_2$ (SEQ ID NO: 23);

Gly-Glu-Ser(p)-Gla-Leu-Gln-Gla-Asn-Gln-Gla-Leu-Ile-Arg-Gla-Lys-Ser-Asn-NH$_2$ (SEQ ID NO:24);

AcTyr-Gly-Glu-Gla-Gla-Leu-Gln-Gla-Asn-Gln-Gla-Leu-Ile-Arg-Gla-Lys-Ser-Asn-NH$_2$ (SEQ ID NO:13);

Asn-Gly-Glu-Gla-Gla-Leu-Gln-Gla-Asn-Gin-Gla-Leu-Ile-Arg-Gla-Lys-Ser-Asn-NH$_2$ (SEQ ID NO: 14);

Asn(GlcNAc)-Gly-Glu-Gla-Gla-Leu-Gln-Gla-Asn-Gln-Gla-Leu-Ile-Arg-Gla-Lys-Ser-Asn-NH$_2$ (SEQ ID NO: 15);

Phe-Gly-Glu-Gla-Gla-Leu-Gln-Gla-Asn-Gln-Gla-Leu-Ile-Arg-Gla-Lys-Ser-Asn-NH$_2$ (SEQ ID NO: 16);

tBuTyr-Gly-Glu-Gla-Gla-Leu-Gln-Gla-Asn-Gln-Gla-Leu-Ile-Arg-Gla-Lys-Ser-Asn-NH$_2$ (SEQ ID NO:20);

Ser-Gly-Glu-Gla-Gla-Leu-Gln-Gla-Asn-Gln-Gla-Leu-Ile-Arg-Gla-Lys-Ser-Asn-NH$_2$ (SEQ ID NO:21);

Gly-Glu-Gla-Gla-Leu-Gln-Gla-Asn-Gln-Ala-Leu-Ile-Arg-Gla-Lys-Ser-Asn-NH$_2$ (SEQ ID NO:35);

Gly-Glu-Gla-Gla-Leu-Gln-Gla-Asn-Gln-Ser-Leu-Ile-Arg-Gla-Lys-Ser-Asn-NH$_2$ (SEQ ID NO:36);

Gly-Glu-Gla-Gla-Leu-Gln-Gla-Asn-Gln-Ser(p)-Leu-Ile-Arg-Gla-Lys-Ser-Asn-NH$_2$ (SEQ ID NO:37);

Gly-Glu-Gla-Gla-Leu-Gln-Gla-Asn-Gln-Gla-Leu-Ile-Arg-Ala-Lys-Ser-Asn-NH$_2$ (SEQ ID NO:38);

Gly-Glu-Gla-Gla-Leu-Gln-Gla-Asn-Gln-Gla-Uu-Ile-Arg-Ser-Lys-Ser-Asn-NH$_2$ (SEQ ID NO: 39);

Gly-Glu-Gla-Gla-Leu-Gln-Glu-Asn-Gln-Glu-Leu-Ile-Arg-Glu-Lys-Ser-Asn-NH$_2$ (SEQ ID NO:41);

Gly-Glu-Gla-Gla-Leu-Gln-Ala-Asn-Gln-Gla-Leu-Ile-Arg-Gla-Lys-Ser-Asn-NH$_2$ (SEQ ID NO:32);

GIy-Glu-Gla-Gla-Leu-Gln-Ala-Asn-Gln-Ala-Leu-Ile-Arg-Ala-Lys-Ser-Asn-NH$_2$ (SEQ ID NO:42);

Gly-Glu-Gla-Gla-Leu-Gln-Ser-Asn-Gln-Gla-Leu-Ile-Arg-Gla-Lys-Ser-Asn-NH$_2$ (SEQ ID NO: 33);

Gly-Glu-Gla-Gla-Leu-Gln-Ser(p)-Asn-Gln-Gla-Leu-Ile-Arg-Gla-Lys-Ser-Asn-NH$_2$ (SEQ ID NO:34);

Gly-Glu-Gla-Gla-Leu-Gln-iodoTyr-Asn-Gln-Gla-Leu-Ile-Arg-Gla-Lys-Ser-Asn-NH$_2$ (SEQ ID NO:53);

Gly-Glu-Gla-Gla-Leu-Gln-di-iodoTyr-Asn-Gln-Gla-Leu-Ile-Arg-Gla-Lys-Ser-Asn-NH$_2$ (SEQ ID NO:54);

Gly-Glu-Gla-Gla-Leu-Gln-Tyr-Asn-Gln-Gla-Leu-Ile-Arg-Gla-Lys-Ser-Asn-NH$_2$ (SEQ ID NO:31);

Gly-Glu-Gla-Gla-Leu-NH$_2$ (SEQ ID NO:52);

Gla-Lys-Ser-Asn-NH$_2$ (SEQ ID NO:49);

Ile-Arg-Gla-Asn-NH$_2$ (SEQ ID NO:50); and

Lys-Ser-Asn-NH$_2$ (SEQ ID NO:51).

DETAILED DESCRIPTION OF THE INVENTION

During the past few years, a number of unusual polypeptides have been isolated from the paralytic venoms of the fish hunting cone snails of the genus Conus found in the Philippine archipelago. Many of these, designated "conotoxins," have been discovered to affect ion channel function. The paralytic $\alpha$, $\mu$, and $\omega$ conotoxins block nicotinic acetylcholine receptors, sodium channels, and voltage sensitive calcium channels, respectively (reviewed in Olivera et al., "Diversity of Conus neuropeptides," *Science*, 249:257–263, 1990.).

Non-paralytic peptides from two of the snails, *Conus tulipa* and *Conus geographus*, have particularly unique compositions since they contain the unusual amino acid $\gamma$-carboxyglutamate (Gla), Conantokin-T (21 amino acids from *tulipas*) containing 4 and Conantokin-G (hereinafter "Con-G") (17 amino acids from *geographus*) containing 5, and also contain an amide group on the carboxyl terminal peptide. The sequence of these amino acids is shown below with the $\gamma$-carboxyglutamate shown in bold:

Conantokin-G: Gly-Glu-Gla-Gla-Leu-Gln-Gla-Asn-Gln-Gla-Leu-Ile-Arg-Gla-Lys-Ser-Asn-NH$_2$ (SEQ ID NO: 1)

Conantokin-T: Gly-Glu-Gla-Gla-Tyr-Gln-Lys-Met-Leu-Gla-Asn-Leu-Arg-Gla-Ala-Glu-Val-Lys-Lys-Asn-Ala-NH$_2$ (SEQ ID NO:12)

Conantokin-T (Con-T) and Conantokin-G (Con-G) were recently reported to act as NMDA receptor antagonists. Haack et al., "Conantokin-T (A $\gamma$-carboxyglutamate containing peptide with N-methyl-D-aspartate antagonist activity)," *J. Biol. Chem.*, 265:6025–6029, 1990; Mena et al., "ConantokinG: a novel peptide antagonist to the N-methyl-D-aspartic acid (NMDA) receptor," *Neurosci. Let.*, 118:241–244, 1990. These two snail peptides were shown to decrease NMDA induced increases of intracellular Ca$^{++}$ levels and to block NMDA induced increases in cGMP levels in both primary neuronal cell cultures and brain slice preparations. Mena et al. (1990), supra, noted that the mechanism of antagonism of Conantokin-G appeared to be different from previously described competitive and non-competitive NMDA receptor antagonists but did not report or suggest the mechanism(s) underlying the antagonism of Conantokin-G or Conantokin-T to NMDA receptor response.

Figure 1:
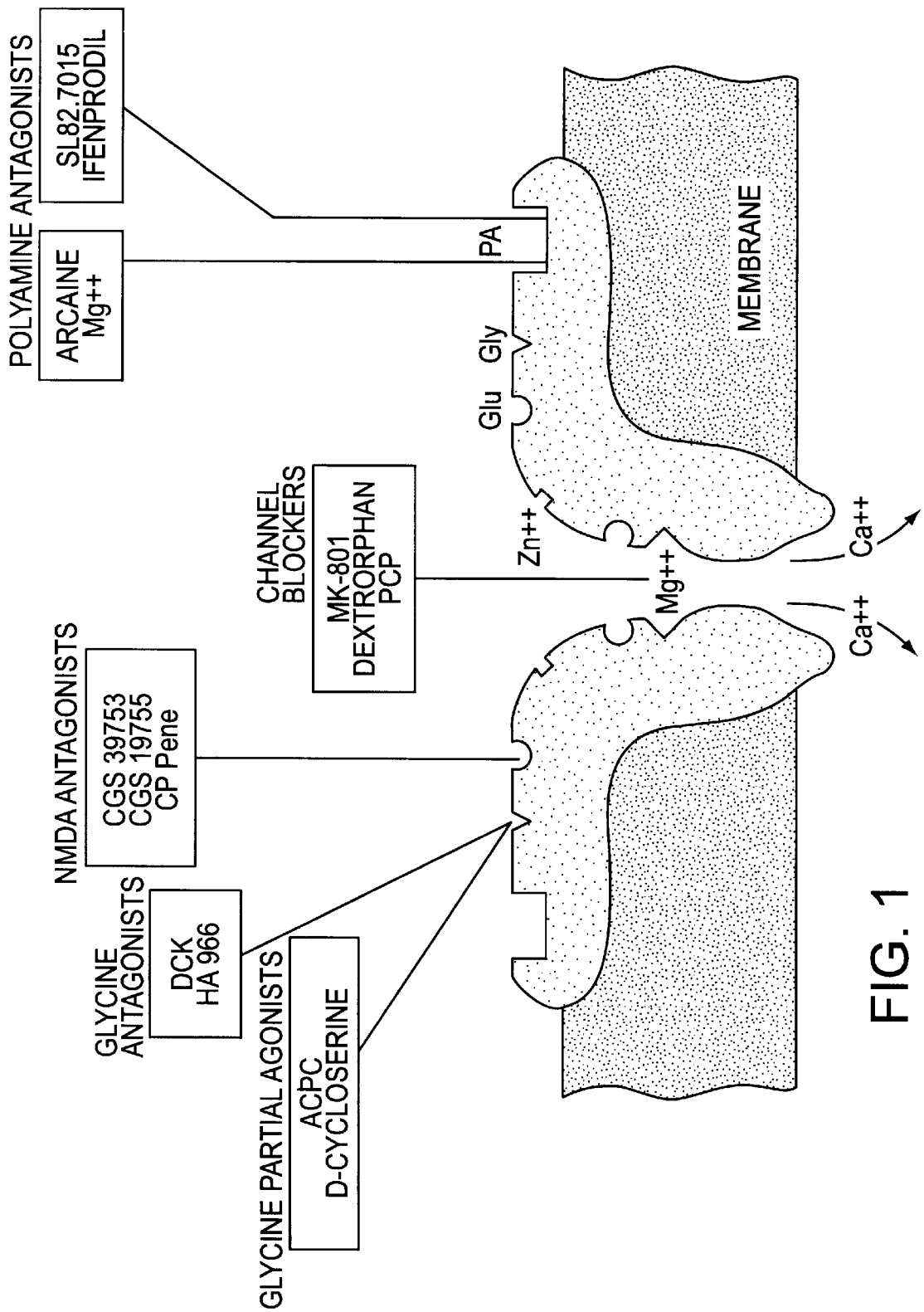
FIG. 1 is a schematic representation of the known binding sites on the NMDA receptor described in the literature indicating both the sites at which stimulatory agonists and inhibitory antagonists bind.
Figure 2:
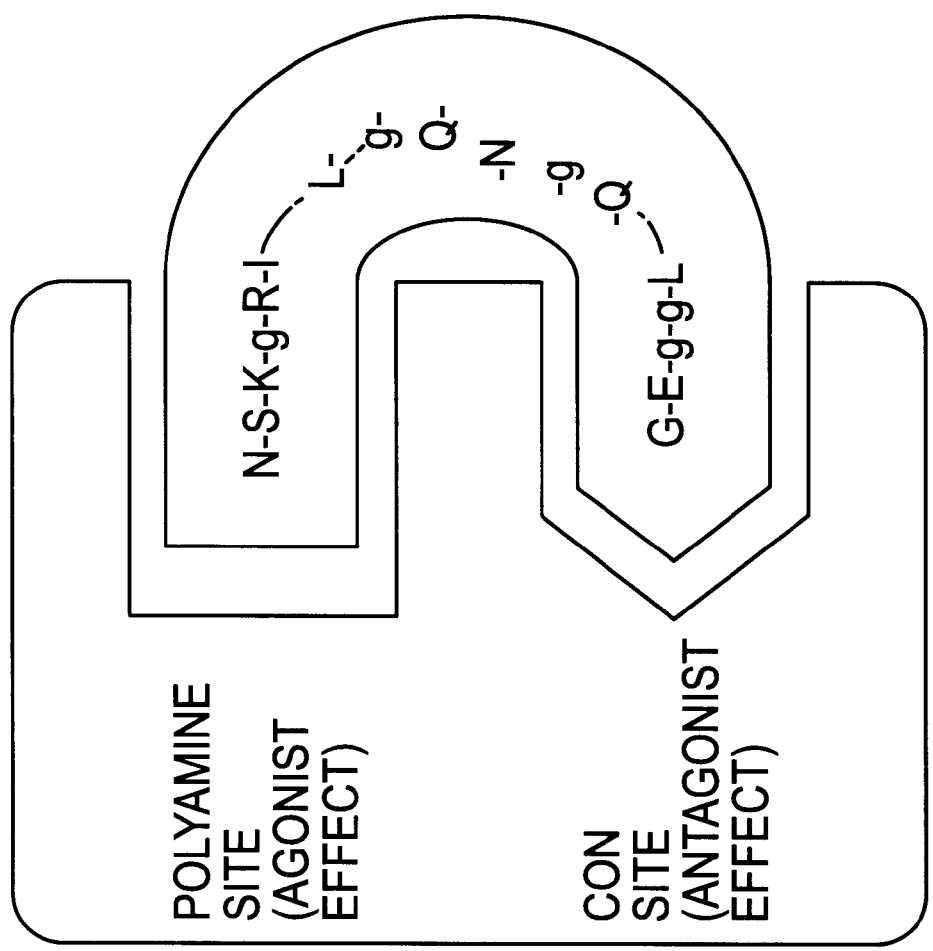
FIG. 2 depicts the Con-G allosteric modulatory complex site and the proposed binding of Con-G thereto.

While Mena et al., supra, had reported that Con-G was an NMDA receptor antagonist which was not competitive with previously known agonists or antagonists, no one had: 1) elucidated the underlying mechanism by which the antagonism is mediated; 2) taught how such antagonism can be utilized to control properties of the receptor; or 3) described accurately the chemical/biological structural requirements for modulatory activity. It has been discovered that Con-G inhibits the stimulatory effect of polyamines on the NMDA receptor. However, Con-G does not act at the polyamine site alone, but also acts at a new and unique modulatory site. In fact, Con-G bridges both sites when functioning. Thus, the Con-G site is actually a complex including at least a portion of the polyamine site and a novel site designated herein as the Con site. (See FIG. 2.)

It has been discovered, by the present inventor, that Con-G acts as an antagonist of the NMDA receptor through its action as a potent, selective, and noncompetitive inhibitor of the polyamine modulated responses with a neurochemical profile which is distinct from previously described polyamine antagonists. It has also been determined that Con-G binds at a unique and heretofore unidentified site on the extracellular domains of the NMDA receptor.

Further, a new class of allosteric modulators has been discovered which are derived from Con-G and act as partial agonists, full agonists, or full antagonists of the NMDA receptor at the polyamine site or a site associated with the polyamine site, both of which are encompassed within the Con-G site. One of these compounds, a four peptide unit—Gla-Lys-Ser-Asn (SEQ ID NO:49)—is a much more potent agonist for the polyamine site than any known polyamine. Another derivative, substituting a Gla with Ala at amino acid residue 7 in the native Con-G sequence, is actually a more potent antagonist than Con-G.

As discussed earlier, in Cordi I and II, supra, and Trullas, supra, agents which act as partial agonists of allosteric sites on the NMDA receptor were used to selectively modulate the receptor's function, apparently without producing the side effects associated with compounds that close the NMDA receptor channel. In addition, Cordi I and II and Trullas described that modulation of NMDA receptor activity by partial agonists is useful in the treatment of a wide range of CNS disorders as well as in enhancement of CNS function.

Specifically, Cordi I and II and Trullas relate to the use of partial agonists of the glycine site to enhance memory, treat learning and cognitive deficits, treat Alzheimers and age associated memory impairment, treat psychotic disorders, improve memory, and treat mood disorders. Recent evidence also indicates that certain types of drug induced convulsions are associated with chemical toxicity affecting the NMDA receptor. Greater control over the modulation of the NMDA receptor, as is possible with the compounds described herein, presents one of the best hopes for dealing with one of the less tractable current societal problems.

Definitions

The following are definitions of terms as used throughout the present specification. These definitions are provided to assist interpretation of, not limit, the invention.

The term "amino acid" as used herein means an α amino acid. Included within this term are natural amino acids, including unusual amino acids such as γ-carboxyglutamate, as well as modified and non-natural amino acids, such as those disclosed in, for example, Roberts et al., *The Peptides*, 5:342–429, 1983, the teachings of which are hereby incorporated by reference.

The term "basic amino acid" as used herein means an amino acid as defined above, in which the side chain has a net positive charge at pH 7.0 including, but not limited to, lysine, arginine, and histidine.

The term "uncharged, hydrophobic amino acid" as used herein means an α amino acid with a hydrocarbon side chain, branched or unbranched, of one to eight carbons.

The abbreviation "Gla" as used herein refers to the amino acid γcarboxyglutamate or γ-carboxyglutamic acid.

The abbreviation "Glu" as used herein refers to the amino acid L-glutamate or L-glutamic acid.

The abbreviation "D-Glu" as used herein refers to the amino acid D-glutamate or D-glutamic acid.

The term "agonist" as used herein includes any compound which increases the flow of cations through an ionotropic receptor such as NMDA, i.e., a channel opener, and which has not been observed to decrease the flow of cations through the same receptor.

The term "antagonist" as used herein includes any compound which reduces the flow of cations through an ionotropic receptor such as NMDA, i.e., a channel closer, and which has not been observed to increase the flow of cations through the same receptor.

The term "partial agonist" as used herein refers to a compound which regulates an allosteric site on an ionotropic receptor, such as the NMDA receptor, to increase or decrease the flux of cations through the ligand-gated channel depending on the presence or absence of the principal site ligand. In the absence of the principal site ligand, a partial agonist increases the flow of cations through the ligand-gated channel, but at a lower flux than achieved by the principal site ligand. A partial agonist partially opens the receptor channel. In the presence of the principal site ligand, a partial agonist decreases the flow of cations through the ligand-gated channel below the flux normally achieved by the principal site ligand. In the presence of the principal site ligand, a partial agonist is, thus, a "partial antagonist." The term "principal site ligand" as used herein refers to known endogenous ligands binding to a site.

The term "agonistic" as used herein refers to any compound which increases the flow of cations through an ionotropic receptor such as NMDA, i.e., a channel opener, and includes agonists and partial agonists.

The term "antagonistic" as used herein refers to any compound which reduces the flow of cations through an ionotropic receptor such as NMDA, i.e., a channel closer, and includes antagonists and partial agonists.

The term "NMDA receptor" as used herein refers to a postsynaptic receptor which is stimulated, at a minimum, by the excitatory amino acids glutamate and glycine, and selectively stimulated by the synthetic compound NMDA. It is a ligand-gated receptor with a strychnine-insensitive glycine site.

The term "potency" as used herein refers to the molar concentration at which a specified effect on a receptor channel is observed. Specifically, potency for a compound exhibiting antagonistic effect is presented as the $IC_{50}$ value, which is the concentration at which inhibition of spermine-induced channel opening is 50% of the maximum inhibition achievable. Lower values indicate higher potency. Potency for a compound exhibiting agonistic effect is presented as the $EC_{50}$ value, which is the concentration at which enhancement of channel opening in the absence of spermine is 50% that of maximum enhancement achievable. Again, lower values indicate higher potency.

The term "efficacious" as used herein refers to a comparison of the maximum channel opening achieved by a particular compound with the maximum channel opening achieved by spermine. Efficacy refers to magnitude of a specified effect.

The term "Con-G site" as used herein refers to the novel complex site as defined by the binding of Con-G, or one of its derivatives, to the polyamine site and the novel Con site to be described below.

The term "polyamine site" as used herein refers to the site that binds spermine and spermidine, as well as a portion of Con-G.

The term "Con site" as used herein refers to the novel site which binds to a portion of Con-G not bound by the polyamine site.

The term "application" as used herein refers to the contacting of a compound or composition with the desired substrate either directly or indirectly, and includes in vitro, in vivo, and in situ contact. The term "administering" as used herein specifically refers to in vivo application.

The term "modulating" as used herein refers to increasing or decreasing the flow of cations through an ionotropic receptor, such as the NMDA receptor. "Modulators" are compounds capable of increasing and/or decreasing the flow of cations through such receptors and include agonists, partial agonists, and antagonists.

The term "regulating" as used herein refers to increasing or decreasing the flow of cations through an ionotropic receptor when said flow has been deviated from normal. "Regulators" are compounds capable of doing both and, therefore, include partial agonists.

The term "neuropsychopharmacological disorder" as used herein refers to a disorder resulting from, or associated with, a reduced or excessive flux of cations through the NMDA receptor ligand-gated cation channel and includes, but is not limited to, cognitive, learning, and memory deficits, chemical toxicity (including substance tolerance and addiction), excitotoxicity, neurodegenerative disorders (such as Huntington's disease, Parkinson's disease, and Alzheimer's disease), post-stroke sequelae, epilepsy, seizures, mood disorders (such as bipolar disorder, dysthymia, and seasonal effective disorder), and depression. Neurodegenerative disorders can result from dysfunction or malfunction of the receptor.

Design of Con G Derivatives Altering the Function of the NMDA Receptor

The discovery that Con-G modulates the response of the polyamines acting at a novel site, which includes the polyamine site and a separate Con site, and that derivatives of Con-G also modulate the effect of polyamines, affords an additional level of control to be exerted over the NMDA receptor. Clearly, Con-G and its derivatives represent new classes of antagonists, agonists, and partial agonists which modulate NMDA receptor function. Since Con-G and its derivatives modulate $Ca^{++}$ influx of specific NMDA receptor sub-types, Con-G and its derivatives are expected to be similarly useful in treating the broad spectrum of neuropsychopharmacological disorders and in enhancement of CNS function as compounds of the prior art, but with a different specificity and spectrum of treatment.

In fact, the range of modulation of the NMDA receptor presented by Con-G and its derivatives—from total antagonism through partial agonism to full agonism—represents far greater control of NMDA receptor function than is possible with the known modulators of the Glu and Gly sites of the same receptor. Thus, Con-G and its derivatives possess a broader range of efficacies for the treatment of CNS disorders and CNS function enhancement than is possible with compounds of the prior art. The compounds and methods of use are described in more detail below.

It has been postulated by others that the alignment of the charged Gla residues is achieved through the a helix and is necessary and sufficient for Con-G's activity at the NMDA receptor. By studying the comparative actions of the Con-G derivatives disclosed below, it was discovered that the chemical/structural requirements both for the antagonistic and agonistic activities of Con-G are complex. Through preparation of synthetic derivatives as disclosed herein, it was determined that the ability of Con-G to act as a strong, non-competitive NMDA antagonist at the newly identified Con-G site is abolished by certain modifications of the Con-G peptide. In fact, it has been discovered that either modification of the N-terminus or replacement of the Gla residues by Glu produces several derivatives which act as partial agonists/antagonists.

The derivatives presented in Table I below will be discussed for purposes of illustration. It should be understood, however, that these are representative compounds which are sufficient to teach the underlying principles relating to structure/activity relationships to persons skilled in the art and, therefore, are not limiting of this disclosure.

The compounds herein described may have asymmetric centers. Unless otherwise indicated, all chiral, diastereomeric and racemic forms are included. All stable isomers are contemplated. Two distinct isomers (cis and trans) of the peptide bond are known to occur; both can also be present in the compounds described herein. A stable isomer is one that is sufficiently robust to survive isolation to a useful degree of purity from a reaction mixture, and formulation into an useful therapeutic agent.

In Table I, the numbers above the sequences indicate each amino acid's position based on the parent Con-G molecule. γ-carboxyglutamate, Gla, is indicated by a lower-case "g." Where glutamate, Glu, was substituted for γ-carboxyglutamate, the single letter amino acid code for glutamate, or "E," is used. "B" refers to amino isobutyvic acid. The nomenclature/abbreviation used to identify each compound throughout the specification and in the claims is set out to the right beside the corresponding polypeptide structure. The numbers in the nomenclature refer to the amino acid residue positions in native Con-G. In the table, and in the claims below, amino acid residues are counted from the amino terminus to the carboxy terminus of native Con-G. Accordingly, the amino acid at the amino terminus is designated "1." The "SEQ ID NO:" for each peptide is indicated in the left-most column.

In Table I, the derivatives are divided into four classes, representing the different modifications effected. Class I represents amino terminal extensions or modifications of the native Con-G peptide. Class II represents internal substitutions within the 17-amino acid peptide. Class III represents carboxy terminal fragments and modifications. Class IV includes amino terminal fragments and modifications. The derivatives are further described below.

The experimental results obtained when testing Con-G and its derivatives for their effect on NMDA receptor function are summarized in Table II below. Select experiments are discussed in greater detail below. In Table II, the first four columns relate to determinations of $^3$[H]MK-801 binding in the presence of the test compound, in the absence of spermine, indicated as "% Sti," and in the presence of the test compound with spermine present at maximum stimulatory concentration, indicated as "% Inh." The concentrations at which stimulation or inhibition is 50% that of the maximum are indicated as EC (µM) and IC (µM), respectively. An "na" indicates that no activity was observed.

In Table II, those compounds exhibiting only inhibition values are full antagonists. Those compounds exhibiting only stimulation values are full agonists. Those compounds exhibiting inhibition and stimulation values are partial agonists.

As indicated in Table II, Con-G inhibits spermine-induced receptor activity, and has no stimulatory effect on receptor activity alone. Thus, Con-G is a full antagonist. However, the derivative Con-G-OH exhibits no activity, either inhibitory or stimulatory. The Con-G α-helix with its aligned charged Gla residues is present in Con-G-OH. Thus, an amidated carboxyl end is necessary to Con-G antagonist activity. Further modifications of the N-terminus of Con-G also change its behavior.

Either acylation (a mechanism known to occur naturally to stabilize polypeptides) or the addition of the amino acid Tyr to the N-terminal residue dramatically modifies Con-G's activity. Ac-Con-G displays no apparent activity, although the entire polypeptide sequence responsible for Con-G's α-helix is still present. The addition of Tyr changes Con-G from a strong non-competitive antagonist of the polyamine modulatory site to an essentially inactive compound, despite the fact that the Con-G α-helix with its aligned Gla residues remains. Thus, an unmodified N- terminus with a charged —NH$_3^+$ is also necessary to Con-G antagonist activity.

The substitution of Glu for Gla reduces the charges at each of the substituted sites along the side of the α-helix while preserving the helix. This substitution also changes Con-G from a strong NMDA antagonist to a partial agonist. Substitution of all 5 Gla residues with glutamate (Glu-Con-G) gives a partial agonist, whereas substitution with D-glutamate (D-Glu-Con-G) abolished NMDA antagonist actions of Conantokin-G.

To evaluate the significance of individual Gla residues of Conantokin-G in determining the potential contribution to biological and secondary structure, three amino acids—alanine (Ala), serine (Ser), and phosphoserine (Ser(p))—were substituted for Gla. Alanine can be easily inserted into γ-helices (Chou et al., "Prediction of the secondary structure of proteins from their amino acid sequence," *Adv. Enzymol.*, 47:145–148, 1978; Argos, et al., "The Chou-Fasman secondary structure prediction method with an extended data base," *FEBS Lett.*, 93:19–24, 1978) but, unlike Glu and Lys, does not carry a charge and, unlike Leu, is not extremely hydrophobic. Replacement of Gla individually with Ala would not interfere with the secondary structure. Serine occupies approximately the same space as Ala does, but is reported to be a helix breaker, and to help form β-turns (Chou et al., "β-turns in proteins," *J. Mol Bio.*, 115:135–175, 1978.) The strong, double negative charge of Gla was replaced by phosphoserine which carries a single negative charge, but this charge is stronger than that of Glu.

The results revealed that the Gla residue in position 4 appears to be required for the NMDA antagonist properties of the parent peptide because the replacement of this residue abolished NMDA antagonist actions. The substitutions of Gla in position 4 with Ala, Ser, and Ser(P) resulted in a complete loss of antagonistic activity.

The Gla residue at position 3 also appears to have some effect on antagonistic properties, although not to the same extent as the Gla residue at position 4. Ala3-Con-G inhibited 34% of binding of [$^3$H]MK-801 produced by maximally effective concentration of spermine (12.5 µM this measure) with IC$_{50}$ 1.8±0.1 µM (n=3). A transition from antagonist to partial agonist activity was observed by replacing Gla in position 3 in the order of Ala3-Con-G (antagonist) to Ser3Con-G and Ser(p)3-Con-G (partial agonists).

In contrast, a Gla residue in positions 7, 10, and 14 may not be necessary for the NMDA antagonist actions. With the exception of Ser(p)7-Con-G and Ser(p)14-Con-G, the 7, 10, and 14-modified peptides inhibited spermine-enhanced [$^3$H]MK-801 binding to baseline values. Indeed, Ala7-Con-G was found to be one of the most potent antagonists of spermine with an IC$_{50}$ value of 45±5 nM (n=b), approximately 4-fold (P<0.01) more potent than Con-G. Ser7-Con-G, Ser10-Con-G, Ser14-Con-G, and Ala14-Con-G displayed potencies similar to that of Con-G (Table II). Ala7-Con-G exerted its actions through a selective and noncompetitive inhibition of spermine action, with a neurochemical profile identical with the parent peptide Con-G.

Strong negative charges introduced by phosphorylated serine have no consistent effects on the biological activity of Con-G. Ser(p)7-Con-G and Ser(p)14-Con-G partially inhibited spermine-enhanced [$^3$H]MK-801 binding by 50 and 31% of the maximum stimulation produced by spermine, respectively, with IC$_{50}$ values of 1.04±0.3 (n=3) and 1.12±0.05 µM (n=3), respectively. As indicated above, Ser(p)3-Con-G exhibits partial agonist activity. Ser(p)10-Con-G, however, exhibits full antagonist activity with an IC$_{50}$ value of 0.56±0.2 µM. These observations, coupled with the findings that the replacement of Gla residues in position 7, 10, 14 have no major effects (although potency may be affected, as indicated by the IC$_{50}$ values) on the actions of Conantokin-G, suggested that these negative charges of Gla do not appear to be an essential element for biological activities of Conantokin-G.

Peptide length, however, did affect observed activity. Short derivatives possessing little or no structure, but having an intact amidated C-terminus, possess polyamine-like agonist activity. In contrast, intermediate carboxy terminal fragments and modifications exhibit no activity. However, as the derivative length approaches the length of the native polypeptide, an amidated C-terminus and longer structure produces partial agonist activity. The length of the structure, thus, appears to be more important for the partial agonist function than for full agonist function. The effect of length in combination with helicity is discussed in more detail below.

For Con-G antagonistic activity, it appears that an amidated carboxyl end, an intact charged (—NH$_3^+$) N-terminus, a properly charged and aligned N-terminal portion, and a linker are required. Even with an amidated carboxyl end, intact N-terminus, and α-helix, modifying the charge distribution along the whole length or the N-terminal portion (as in Glu-Con-G, Ser3-Con-G, and Ser(p)3-Con-G) changes the allosteric modulatory properties to that of a partial agomnst.

Finally, changing Con-G's N-terminus structure by lengthening Con-G, as in tBu-Tyr$^0$-Con-G and Phe$^0$-Con-G apparently interferes with the proper binding necessary for antagonism, again producing a partial agonist. Conversely, other extensions, like Tyr$^0$-Con-G, interfere with proper binding necessary for any activity. Depending on stevic interference of the N-terminal extension, antagonistic, agonistic, or no activity results.

An analysis of the range of activities exhibited by the Con-G derivatives shows that an intact amidated carboxyl terminus is required to achieve agonistic activity, while the N-terminus structure is crucial to achieving antagonistic or partial agonist, activities. No where is this dichotomy more evident than in Glu-Con-G(12–17) and Con-G(14–17). Con-G(14–17), which preserves the C-terminus, is the shortest polyamine-like agonist yet observed. It binds tightly with a potency of 1.3 $\mu$M, the highest potency ever observed for a polyamine site ligand.

From the foregoing results, the general structure Formula I was determined. This formula can be further divided into general structure formulas for full agonists, partial agonists, and full antagonists, respectively. For example, in one embodiment, for full agonists, $x^a$ and m are zero. In another embodiment for partial agonists, m and n both equal 1. For full antagonists m and n could either both equal 1, or n could be zero.

Whether the activity of the Con-G derivatives as partial agonists reflected modulation of the polyamine site directly was not clear initially. The fact that they exhibited polyamine-like agonistic properties suggested that they were acting at the polyamine site. Supporting this possibility is the fact that Con-G, which has been discovered to inhibit polyamine modulation of the polyamine site, also inhibits Glu-Con-G stimulated [$^3$H]MK-801 binding, thus suggesting that Glu Con-G also acts at the polyamine site.

The features of Con-G and its derivatives noted above are consistent with a physical structure of the NMDA receptor which places the polyamine modulatory site in close proximity to the novel Con site so that, together, they form the novel Con-G complex site (i.e., the "Con-G site"). As with all protein structures, although the sites may well be in close physical proximity, they may be separated by many intervening residues along the folded protein.

As depicted in FIG. 2, the N-terminus of Con-G binds to one part of the Con-G site (designated the "Con site") while the C-terminus binds to at least a portion of the polyamine site. A certain length appears necessary to bridge the distance between the two sites, as evidenced by the results obtained with the derivatives. At least some of the highly charged Gla residues, in particular at amino acid position four, apparently are responsible for binding to the correct and critical determinants of the NMDA receptor for antagonistic function.

The action of Con-G, thus, is similar to that of other known ligands which bind in such a manner as to effect a relative movement of adjoining protein segments towards or away from each other, to cause the opening and closing of an ion channel. Given this understanding of the structural requirements for Con-G activity, it is possible to design molecular analogs of Con-G and its derivatives which possess the required binding characteristics, and which are modified to increase or decrease the modulatory effects (activities) at these sites. Thus, not only has the mode of action of Con-G been elucidated, but also a new class of compounds has been discovered which allosterically modulate a polyamine associated site of the NMDA receptor over a very wide range of activities.

As indicated above, new classes of allosteric modulators of the Con-G site, acting at the polyamine site and/or the Con G site, have been discovered which exhibit a range of activities from full antagonism, to partial agonism, to full agonism. This class of compounds may be used to modulate the flow of ions through the NMDA receptor. The range of modulation of the compounds acting at the site goes from partially inhibitory (down modulatory) to partially stimulatory (up modulatory). Depending on the required activity, compounds from this class can be used as pharmaceutical neuroprotectants to treat acute cases of massive $Ca^{++}$ influx due to CNS injury and trauma, as well as to treat convulsions, mood disorders, and other neuropsychiatric and neurodegenerative diseases due to chronic disturbances in control of $Ca^{++}$ influx. Similarly, compounds of this class can be selected for the required activity to treat cognitive deficits and to enhance memory and learning.

The discovery that Con-G acts as a non-competitive antagonist of polyamine stimulation of the NMDA receptor suggests that it can be used pharmaceutically to modulate/regulate the NMDA receptor response both in those instances where the enhanced $Ca^{++}$ flux through the NMDA receptor is stimulated by polyamines and in those situations where excess stimulation by other allosteric modulators relies on an appropriate level of polyamines being present and active.

Pharmaceutical Compositions

The compounds can be administered parenterally, i.e. subcutaneously, intramuscularly, intracerebroventricularly, or intravenously and, alternatively, intrathecally. In appropriate carriers or in combination with agents enhancing passage of the blood brain barrier, they can be administered orally or nasally.

Suitable pharmaceutical carriers are known to those skilled in the art. For example, when the active ingredient is administered parenterally, in sterile liquid dosage forms, the carrier can be water, a suitable oil, saline or other buffered physiological solution, aqueous dextrose or related sugar solutions and glycols, such as propylene glycol or polyethylene glycol. Solutions for parenteral administration preferably contain a water soluble form of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propylparaben, and chlorobutanol. Suitable pharmaceutical carriers can be included and are described in *Remington's Pharmaceutical Sciences*, 17th ed., Mack Publishing Co., Easton, Pa, p.1418 (1985), a standard reference text in this field incorporated herein by reference).

The active ingredient can be administered orally in solid dosage forms, such as capsules, tablets and powders, or in liquid dosage forms, such as elixirs, syrups, and suspensions, if first encapsulated in an agent which is stable to passage through the gastrointestinal tract and which allow passage through the blood brain barrier, such as some of the stabilized or covalently crosslinked liposomes. Passage through the blood brain barrier can be enhanced using agents such as some of the phospholipids or lecithin derivatives described in the literature.

Other agents that can be used for delivery include liposomes, microparticles (including microspheres and microcapsules), and other release devices and forms that provide controlled, prolonged or pulsed, delivery or which enhance passage through the blood brain barrier, for example. These are most preferably implanted at or within the blood brain barrier to provide controlled release over an appropriate period of time.

Bioerodible microspheres can be prepared using any of the methods developed for making microspheres for drug delivery, for example, as described by Mathiowitz and Langer, *J. Controlled Release* 5,13–22 (1987); Mathiowitz, et al., *Reactive Polymers* 6, 275–283 (1987); and Mathiowitz, et al., *J. Appl. Polymer Sci.* 35, 755–774 (1988), the teachings of which are incorporated herein. The selection of the method depends on the polymer selection, the size, external morphology, and crystallinity that is desired, as described, for example, by Mathiowitz, et al., *Scanning Microscopy* 4,329–340 (1990); Mathiowitz, et al., *J. Appl. Polymer Sci.* 45, 125–134 (1992); and Benita, et al., *J. Pharm. Sci.* 73, 1721–1724 (1984), the teachings of which are incorporated herein. Methods routinely used by those skilled in the art include solvent evaporation, hot melt encapsulation, solvent removal, spray drying, phase separation and ionic crosslinking of gel-type polymers such as alginate or polyphosphazines or other dicarboxylic polymers to form hydrogels.

Other delivery systems including films, coatings, pellets, slabs, and devices can be fabricated using solvent or melt casting, and extrusion, as well as standard methods for making composites.

The microparticles can be suspended in any appropriate pharmaceutical carrier, such as saline, for administration to a patient. In the most preferred embodiment, the microparticles will be stored in dry or lyophilized form until immediately before administration. They will then be suspended in sufficient solution for administration. The polymeric microparticles can be administered by injection, infusion, implantation, orally, or administration to a mucosal surface, for example, the nasal-pharyngeal region and/or lungs using an aerosol. The other devices are preferably administered by implantation in the area where release is desired. Lower dosages are used with implantable controlled release devices than with other forms of administration other than direct administration to the brain.

The appropriate dosages will depend upon the route of administration and the treatment indicated, and can be readily determined by one skilled in the art. Dosages are generally initiated at lower levels and increased until desired effects are achieved. A dosage range of 1 to 40 mg/kg body weight is contemplated. These dosages are based on extrapolation from studies using compounds of similar size peptides, such as WO 93/10145, originally filed Nov. 12, 1991, which describes compositions for the delayed treatment of ischemia-related neuronal damage, including the omega conotoxin peptide OCT MVIIA, which is 25 amino acids long. Neuroprotective effects were reported with intravenous administration of OCT MVIIA at doses of 15 mg/kg and less. U.S. Pat. No. 5,051,403, issued Sep. 24, 1991, described intracerebroventricularly injection of omega conotoxin peptides to reduce anatomical damage resulting from global ischemia. Doses of 1 μg or less per 50–80 gram gerbil were used. Protective effects were observed at dosages of less than 0.1 μg.

Assays for Determining Functional Activity of Compounds

The following methods and materials were used to determine the activity of the peptides described herein. They can be used with only routine experimentation to test many other peptide embodiments derived from Con G for use as partial agonists, agonists, or antagonists, as described herein.

Peptide Synthesis

Con-G was synthesized and purified by a modification of the method of Rivier et al., *Biochemistry*, 26:8508–8512 (1987), incorporated herein by reference. Amino acid derivatives and solid-phase resins were obtained from Bachem Feinchemikalien AG (Bubendorf, Switzerland) and Novabiochem. In general, peptides were synthesized on a MilliGen 9050 automated peptide synthesizer by using a polystyrene-polyepoxy graft copolymer resin (Rapp et al., *Innovation and Perspectives in Solid Phase Synthesis*, R. Epton, ed., SPCC, Birmingham, pp 205–210, 1990, incorporated herein by reference). Standard Fmoc-chemistry (9-fluorenylmethyloxycarbonyl, Fields et al., "Solid-phase peptide synthesis utilizing 9-fluorenylmethoxycarbonyl amino acids," *Int. J. Peptide Protein Res.*, 35:161–214, 1990, incorporated herein by reference) was used throughout. The amino acids were coupled with a 4-fold molar excess of pentafluorophenyl esters, HBTU or TETU. Peptides were cleaved from the solid support with trifluoroacetic acid (TFA) containing 5% of thioanisole as scavenger. The peptides were precipitated with ether and purified with reversed-phase high performance liquid chromatography (RP-HPLC). A minor fragment of the peptides was purified in the absence of TFA, to exclude the presence of large amounts of counter ions that may interfere with the conformational analysis. The integrity of the peptides was verified by amino acid analysis and fast atom bombardment mass spectroscopy.

Fmoc-Gla (di-t-Bu-OH) was coupled with smaller molar excess (2 to 2.5) with a coupling time of 90 minutes. Synthesis of $Tyr^0$-Con-G was accomplished by an additional carbodiimide-mediated coupling step with Fmoc-Tyr (O-tBu-OH) to the final peptide resin. The $N^\alpha$-acetyl Con-G (Ac-Con-G) analog was prepared by treating the peptide resin with 20% piperidine in dimethylformamide (DMF) for 30 minutes to remove the Fmoc group. Following a series of washes with DMF, dichloromethane, and isopropyl alcohol, a positive Kaiser test (Kaiser et al., *Analyt. Biochem.*, 34:595, 1970, incorporated herein by reference) was obtained indicating complete removal of the Fmoc group. The peptide-resin was treated with 20% acetic anhydride in DMF for 30 minutes. A negative Kaiser test indicated complete blocking of the N-terminal amino group.

All analogs not containing Gla were synthesized using a BOC/Bzl (t-butyloxycarbonyl/benzyl) strategy incorporating the preprogranmmed protocols of an automated peptide synthesizer (Applied Biosystems 431-A, Foster City, Calif. Cleavage and deprotection of each of the analogs was accomplished by treatment with liquid hydrogen fluoride (HF) in the presence of m-cresol. Each analog was purified to homogeneity by reverse-phase HPLC on a Waters $C_{18}$ silicon column using a linear gradient from 10% to 30% acetonitrile into $H_2O$ containing 0.1 % TFA over 60 minutes. Highly pure fractions were combined and lyophilized. Amino acid analysis results were within 10% of theoretical for each peptide.

In the synthesis of phosphopeptides, the serine residue to be phosphorylated was incorporated with its side-chain hydroxyl group unprotected, and phosphorylation was carried out on the resin after the peptide assembly was completed by using dibenzyl phosphochloridate (Otvos et al., "Solid-phase synthesis of phosphopeptides," *Int. J. Peptide Protein Res.*, 34:129–133, 1989, incorporated herein by reference). The phosphopeptides were purified by RP-HPLC (Otvos et al., "Reversed phase high performance liquid chromatographic separation of phosphopeptide isomers," *J. Chromatography*, 512:265–272 (1990), incorporated herein by reference) and analyzed by phosphoamino acid-sensitive amino acid analysis (Gorbics et al., "Successful and rapid verification of the presence of a phosphate group in synthetic phosphopeptides using the conditions of standard dabs-Cl amino acid analysis," *J. Liquid Chromatogr.*, 17:175–189, 1994, incorporated herein by reference) and mass spectroscopy. This synthetic strategy provided serine and phosphoserine-containing peptides at the same time.

Binding Assays

Membrane Preparation:

Male Sprague-Dawley rats (175–300 grams, Taconic Farms, Germantown, N.Y.) were killed by decapitation. Forebrains minus cerebellum and brain stem were removed and homogenized with a Polytron homogenizer (setting 6, 30 seconds) using 10 volumes of 0.32 M sucrose in the assay buffer (5 mM Hepes/4.5 Mm Tris buffer, Ph 7.8). All procedures were carried out at 4° C., unless specified otherwise. The homogenate was diluted to 50 volumes with assay buffer and centrifuged at 1,000×g for 10 minutes. The supernatant was decanted and recentrifuged at 20,000×g for 20 minutes. The resulting pellet was resuspended in 50 volumes of assay buffer and centrifuged at 8,000×g for 20 minutes. The supernatant and outer "buffy" pellet coat were collected and centrifuged at 20,000×g for 20 minutes. The supernatant was discarded, and the pellet was resuspended in 50 volumes of assay buffer containing 1 mM EDTA prior to recentrifugation at 20,000×g for 20 minutes. This resuspension/centrifugation procedure was repeated 3–4 times. The last cycle(s) were performed using assay buffer without EDTA. The resulting pellet was resuspended in 5 volumes of assay buffer, frozen over solid $CO_2$, and stored at −70° C. On the day of assay the tissue was thawed, diluted with 10–50 volumes of assay buffer, and centrifuged at 20,000×g for 20 minutes. The supernatant was discarded, and the resulting pellet was resuspended in 50 volumes of assay buffer and centrifuged at 20,000×g for 20 minutes. The final pellet was resuspended in 30–50 volumes of assay buffer without further modification.

Radioligand Binding

Binding assays were performed in a total volume of 500 µl containing approximately 40–200 µl containing approximately 40–200 µg protein (membrane preparation), 50 µl [$^3$H]MK-801 (final concentration, 4–5 nM), and test compounds or buffer. [$^3$H]MK-801 (specific activity 28.8 Ci/mmol) was obtained from DuPont-NEN (Boston, Mass.). Assays were incubated for 2 hours at room temperature and terminated by rapid filtration under partial vacuum (Brandel Cell Harvester, Model M-24R) with two 5 ml washes of buffer over glass fiber filters that were presoaked in 0.03% polyethyleneimine. Nonspecific binding was determined using phencyclidine hydrochloride (PCP, 100 µM) and represented about 15–50% of the total binding in the absence of modulatory agents. Radioactivity retained in the filter was measured in Ultima Gold scintillation liquid using a Packard 1600TR liquid scintillation counter. Protein content was determined using the BCA Protein Assay Reagent (Pierce, Rockford, Ill.).

The following assays can be used to study in vivo activity.

Mongolian gerbil Forebrain Ischemia Assay

The Mongolian gerbil forebrain ischemia assay is used to determine the extent of protection afforded by a test compound on neural brain cells subjected to ischemic conditions as a model of neurodegeneration. Male Mongolian gerbils are injected ip, iv, and icv with the test compound prior to carotid occlusion. Carotid flow is then occluded for 5–20 minutes by clamps and then opened and inspected to confirm reflow. The gerbils are kept alive for 7 days following surgery and then anesthetized with pentobarbital and perfused transcardially with saline with heparin followed by buffered formalin. The brain is removed, trimmed, and prepared for histological processing. Brain sections are stained and damaged neurons in the CA1 region of the hippocampus are examined. The effects of the test compound are compared to untreated controls. Cell loss is reduced in the gerbils pretreated with test compounds exerting a protective effect against ischemia-induced neurodegeneration. The compounds are expected to be active in this test at a dose of about 1–40 mg/kg, iv or ip.

Forced Swim Test

Compounds with antidepressant activity reduce the time of mouse immobility as measured by the "forced swim test" described by Trullos et al., "Functional antagonists at the NMDA receptor complex exhibit antidepressant actions," *Eur. J. Phann.*, 185:1–10 (1990) and references therein (incorporated herein by reference). Mice are placed individually in a cylinder (i.e., having a diameter of 10 cm and height of 25 cm) filled with water (6 cm) at 22–25° C. The duration of immobility is scored during the last four minutes of a six minute test. The compounds are expected to be active in this test at a dose of about 1–40 mg/kg ip.

Elevated Plus Maze

Compounds with antidepressant activity increase both the percentage of time and percentage of entries into the open arms of an elevated plus-maze as described by Trullos et al., "1-Aminocyclopropanecarboxylates exhibit antidepressant and anxiolytic actions in animal models," *Eur. J. Pharm.*, 203:379–385 (1991), incorporated herein by reference. A mouse is placed at the intersection of the maze arms so that its head is in the center of the platform. The mouse is then scored as being in the open or enclosed arms. Arm entries are recorded and the percentage of time in each arm, as well as the percentage of entries, are calculated. The compounds are expected to be active in this test at a dose of about 1–40 mg/kg ip.

NMDA Induced Seizures

Compounds which have anticonvulsant activity for convulsions involving the NMDA receptor are active in a test described by Koek et al., *Mechanisms for Neuromodulation and Neuroprotection*, pp 665–671, Kamenka et al., eds., NPP Books, Ann Arbor, Mich., 1992, incorporated herein by reference. Test compounds are injected into mice at 15 minutes or 30 minutes before an ip injection of NMDA, icv or ip, respectively. $ED^{50}$ is determined by comparing the percentage of mice that die after 30 minutes to a group of mice that receive NMDA alone. The compounds are expected to be active in this test at a dose of about 1–40 µg/kg icv, or 1–40 mg/kg ip.

Cocaine Induced Convulsions

Compounds with anticonvulsant activity for cocaine induced convulsions are active in tests described by Witkin et al., *Life Sciences*, 48:51–56, 1991, incorporated herein by reference. Male Swiss Webster mice, 10–12 weeks old, are injected with the test compound ip 30 minutes prior to an ip injection of 75 mg/kg cocaine. The occurrence of convulsions is recorded for 15 minutes following the cocaine injection and are defined as loss of righting responses for at least 5 seconds and the occurrence of clonic limb movement. The $ED_{50}$ dose can then be calculated. The compounds are expected to be active in this test at doses of about 1–40 mg/mg ip.

EXAMPLE 1

Characterization of Con G Activity

Figure 3B:
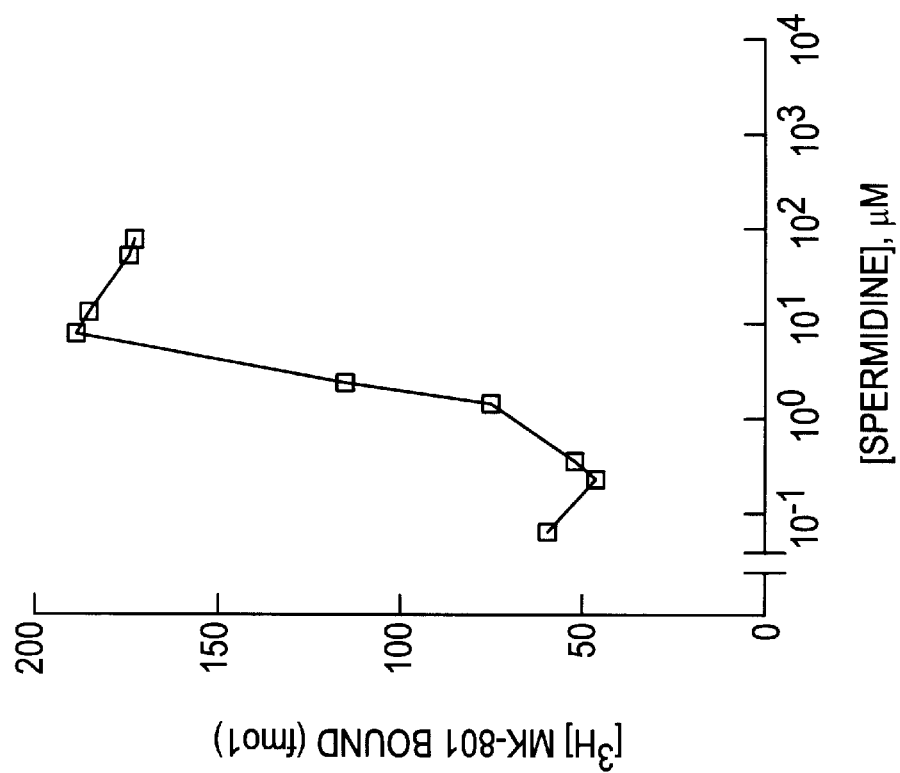
FIGS. 3a and b plot the stimulation of the NMDA receptor in well-washed forebrain membranes by polyamines as indicated by increased [$^3$H]MK-801 binding to the receptor in the nominal absence of endogenous Glu and Gly.
Figure 3A:
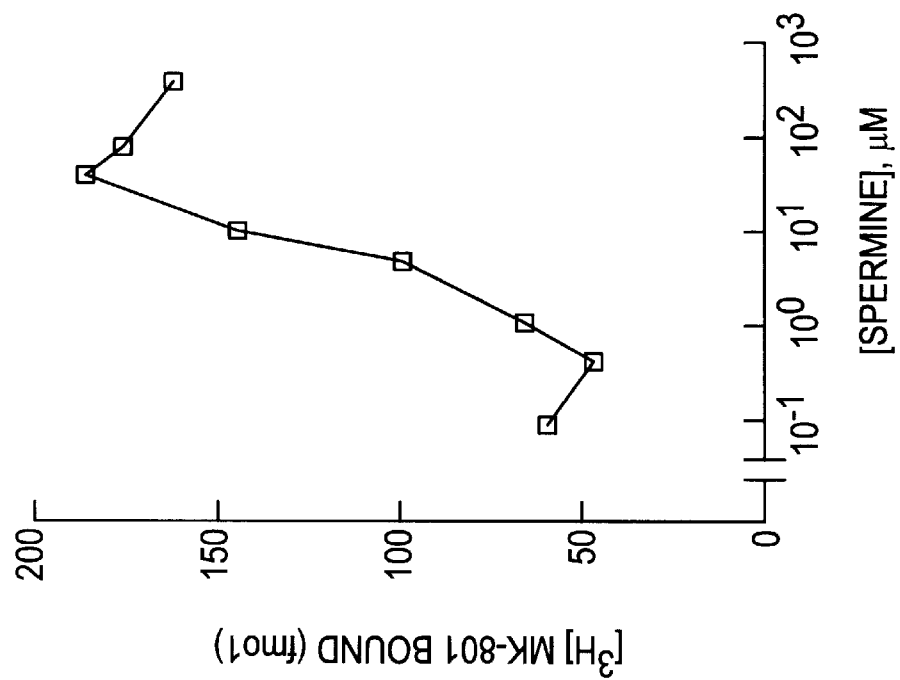

FIGS. 3a and 3b are plots of the binding of [$^3$H]MK-801 as a function of increasing concentrations of spermine and spermidine, respectively, in the nominal absence of endogenous Glu and Gly. While the forebrain membrane preparations were washed very well, as noted in the methods section above, it is believed that it is not entirely possible to totally remove these amino acids from the membrane preparations, as indicated by the high non-specific binding in such assays. As can be seen from the figures, both of these polyamines stimulate the binding of [$^3$H]MK-801 in a concentration dependent fashion, confirming that they allosterically modulate the opening of the ligand-gated NMDA channel.

Figure 4B:
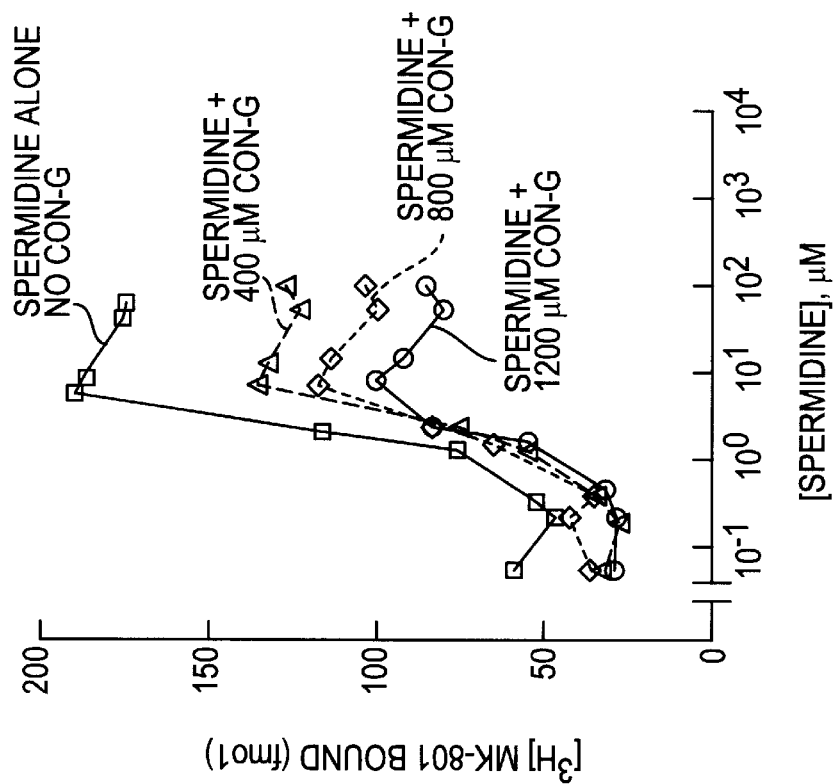
FIGS. 4a and b depict the antagonistic effect of Con-G on spermine (4a) and spermidine (4b) induced [$^3$H]MK-801 binding at varying concentrations of Con-G.
Figure 4A:
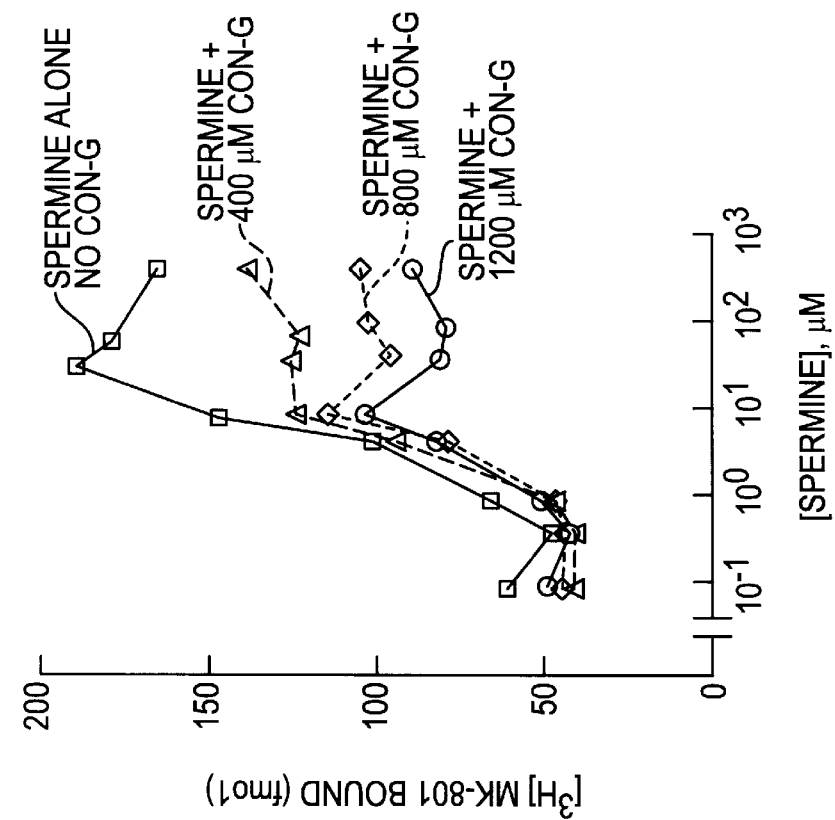

FIGS. 4a and 4b depict the effect on spennine- and spermidine-stimulated binding of [$^3$H]MK-801, as depicted in FIGS. 3a and 3b, when varying amounts of Con-G are added to the membrane preparation. In the figures, squares represent no added Con-G; triangles represent Con-G at 400 μM; diamonds represent Con-G at 800 μM; and circles represent Con-G at 1200 μM.

As can be seen from the figures, as the concentration of Con-G increases from 400 μM to 1200 μM, the degree of polyamine stimulated [$^3$H]MK-801 binding concomitantly decreases, thereby reflecting a more and more closed state of the channel. Con-G does not decrease the polyamine stimulated binding in a concentration dependent manner which would be consistent with competitive inhibition, but does decrease the stimulation in a manner consistent with non-competitive inhibition of the polyamines.

Figure 5:
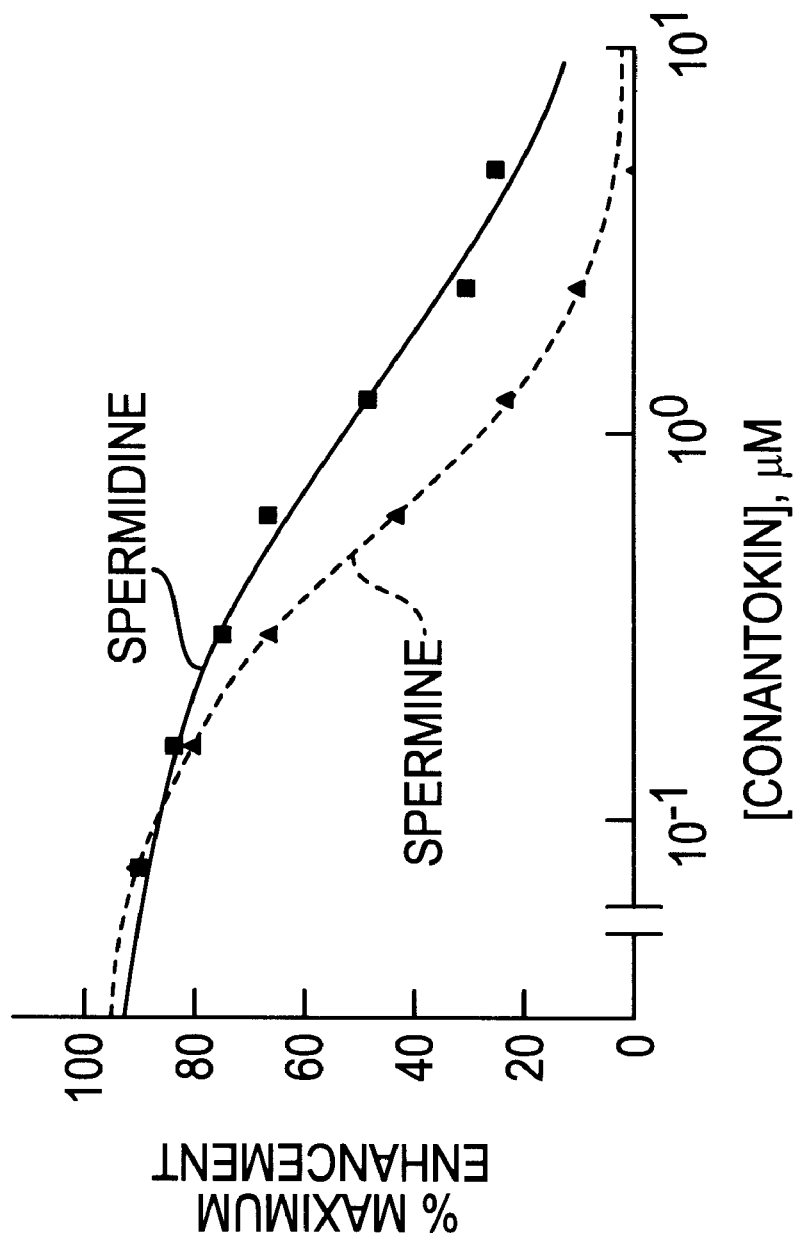
FIG. 5 depicts concentration dependent inhibition of the maximum stimulation of [$^3$H]MK-801 binding to brain membranes produced by spermine and spermidine as the concentration of Con-G increases.

FIG. 5 is a plot of the reduction in maximum stimulation of [$^3$H]MK-801 binding achieved by spermine (squares) and spermidine (triangles), at 50 μM concentration each, as the concentration of Con-G increases. There is no consistent relationship between the degree of inhibition of the polyamine stimulation and the concentration of Con-G such as is found with the polyamines diethylenetriamine and arcaine, both of which inhibit spermine and spermidine enhanced [$^3$H]MK-801 binding through a competitive antagonism at the polyamine site, further indicating that Con-G is not acting as a competitive inhibitor of the polyamines at the polyamine site.

Figure 13:
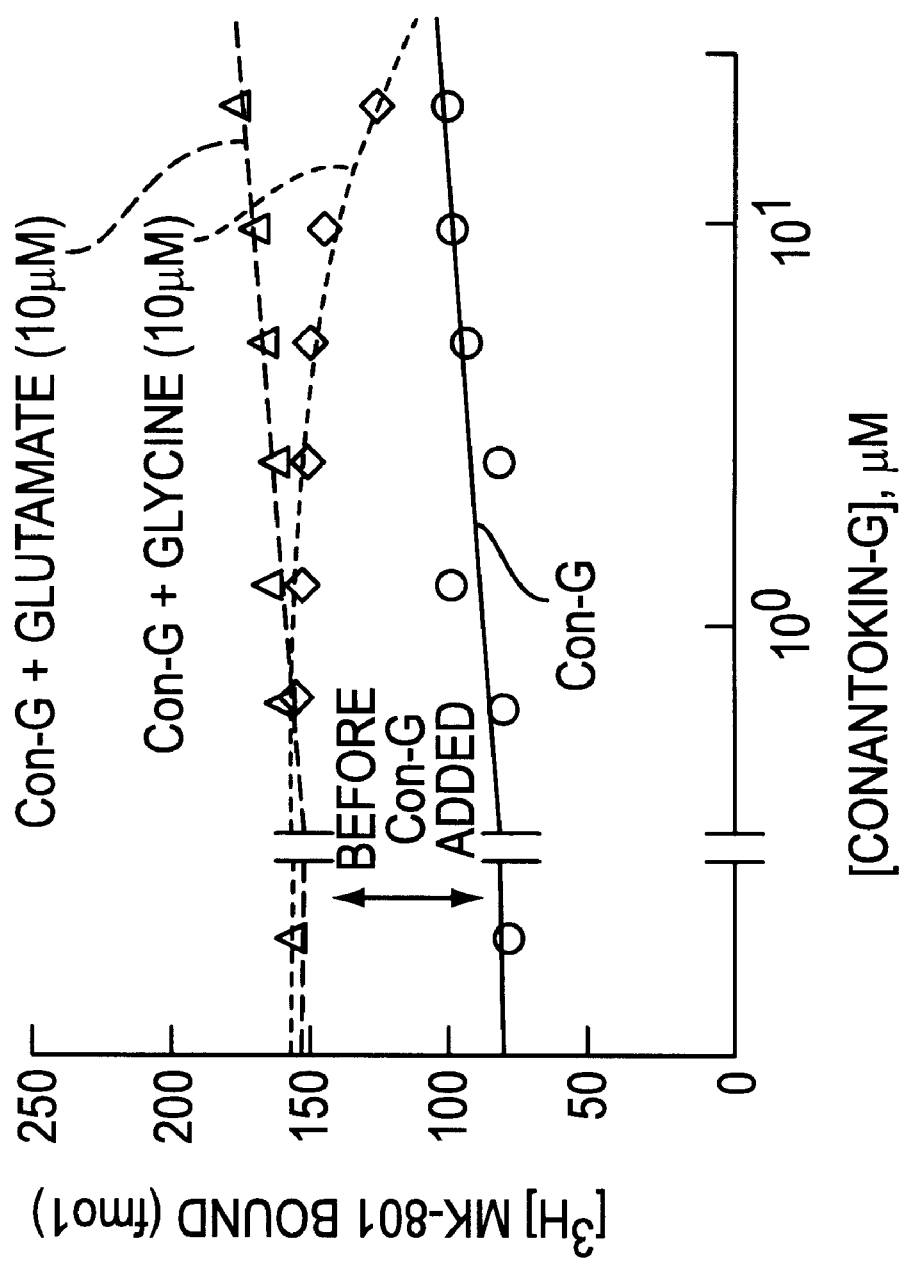
FIG. 13 shows the effect of increasing concentrations of Con-G upon basal [$^3$H]MK-801 binding and Gly (10 $\mu$M) and Glu (10 $\mu$M) stimulated [$^3$H]MK-801 binding to brain membranes.
Figure 14:
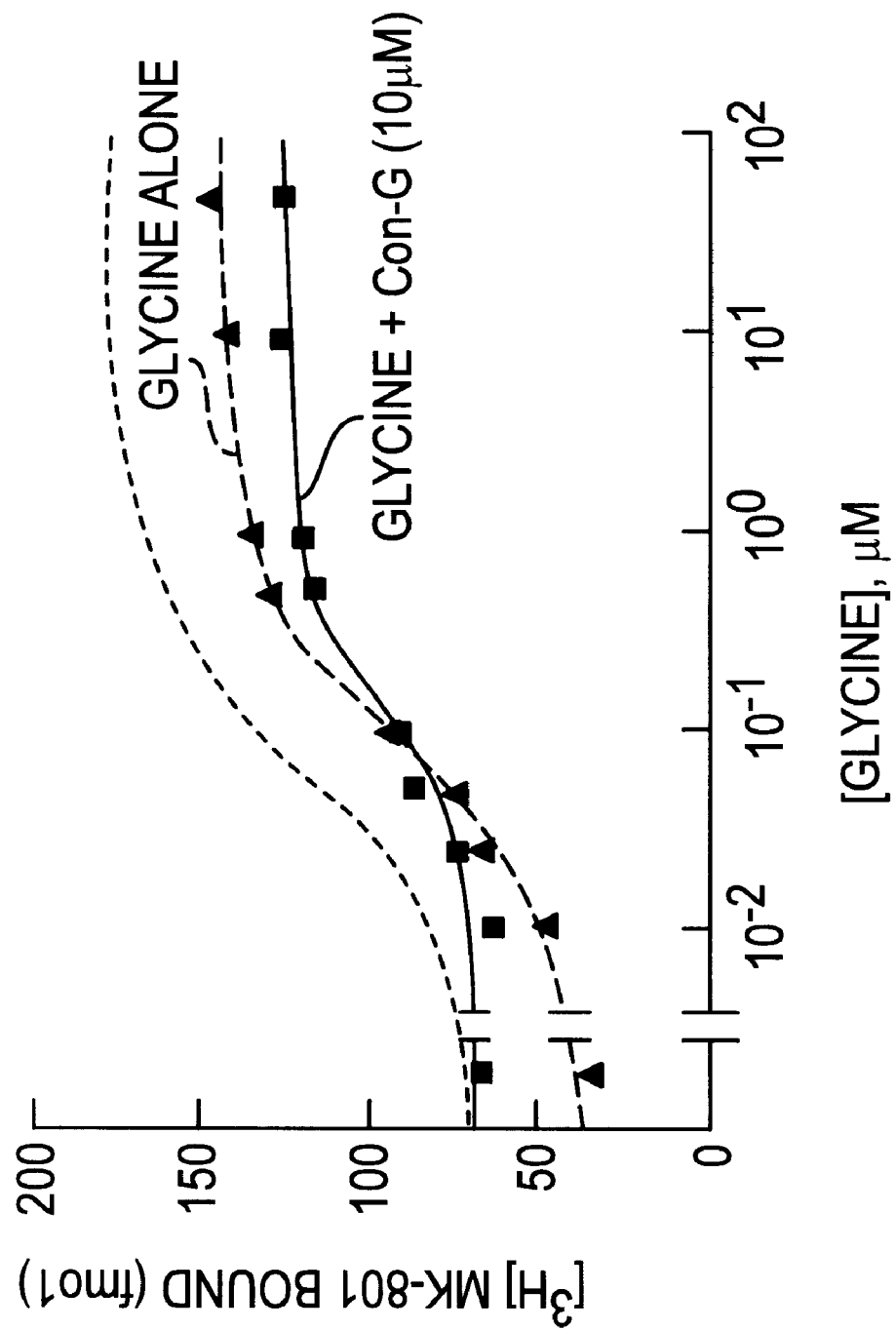
FIG. 14 depicts the effect of 10 $\mu$M Con-G on Gly stimulated [$^3$H]MK-801 binding to brain membranes as a function of increasing Gly concentration.
Figure 15:
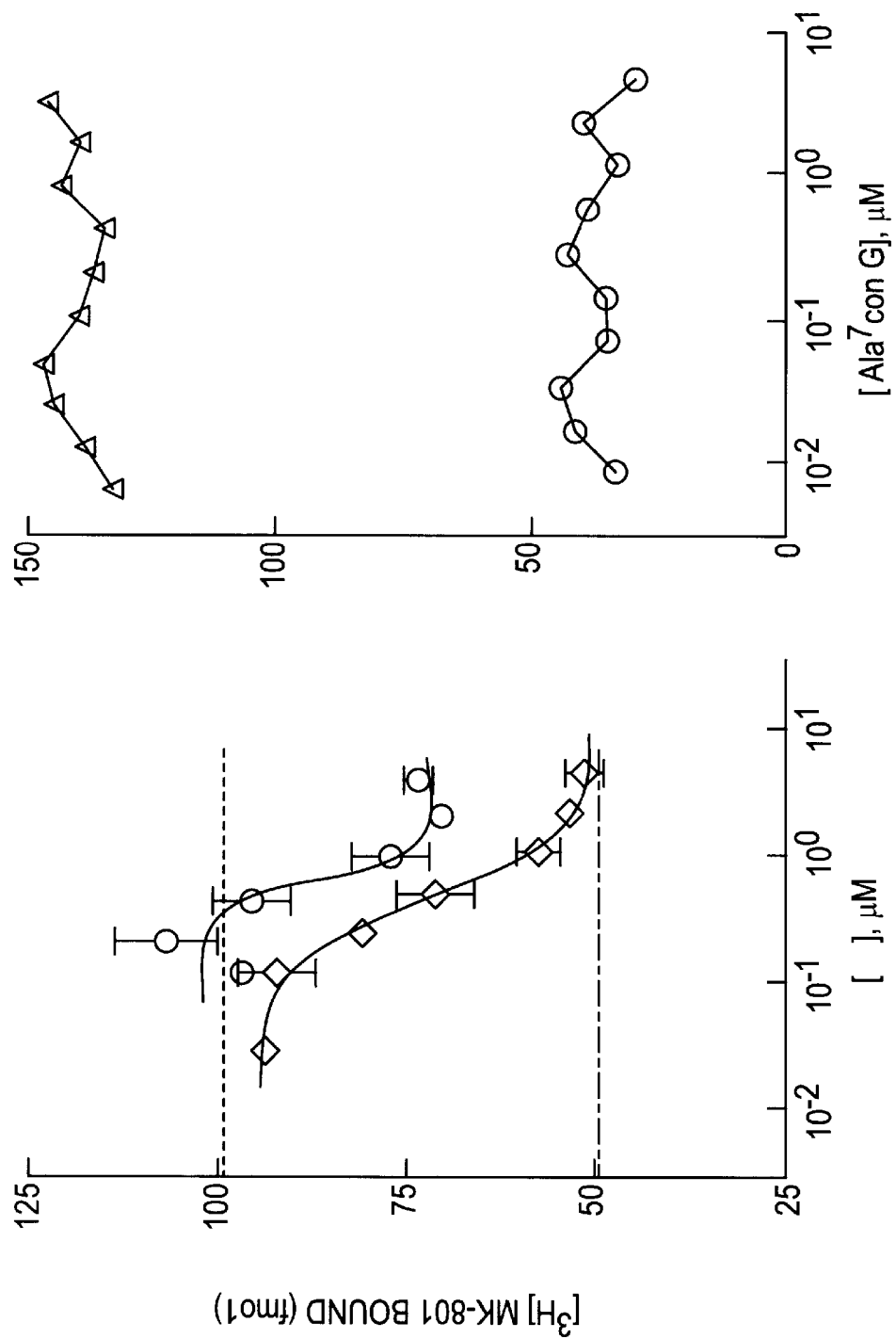
FIGS. 15 a and b depict the effects of Ala7-Con-G on basal, Gly-, and Glu-enhanced [$^3$H]MK-801 binding.

In FIG. 13, the effect of increasing concentrations of Con-G upon basal [$^3$H]MK-801 binding is depicted. The curves preceding the break (•) represent [$^3$H]MK-801 binding in the absence of Con-G. As can be seen from FIG. 13, Con-G produces a small increase in basal [$^3$H]MK-801 binding. This increase is very modest compared to the enhanced binding produced by Glu, Gly, and the polyamines.

EXAMPLE 2

Con G Derivatives Exhibiting Full Antagonist Activity.

The peptides disclosed in Table I were tested for their effect on spermine-induced binding of [$^3$H]MK-801 in the radioligand binding assay described previously. All the compounds with antagonistic activities are active in this assay.

As shown in FIG. 4, Con-G acts as a very strong antagonist. Like native peptide Con-G, Ala7-Con-G inhibited spermine-induced binding, and in a non-competitive manner. This was manifested by analysis of concentration—response data of spermine generated in the presence of various concentrations of Ala7-Con-G. There was a progressive downshifting of concentration-response curves of spermine as the concentrations of Ala7 increased. Results are depicted in FIG. 6.

Figure 6:
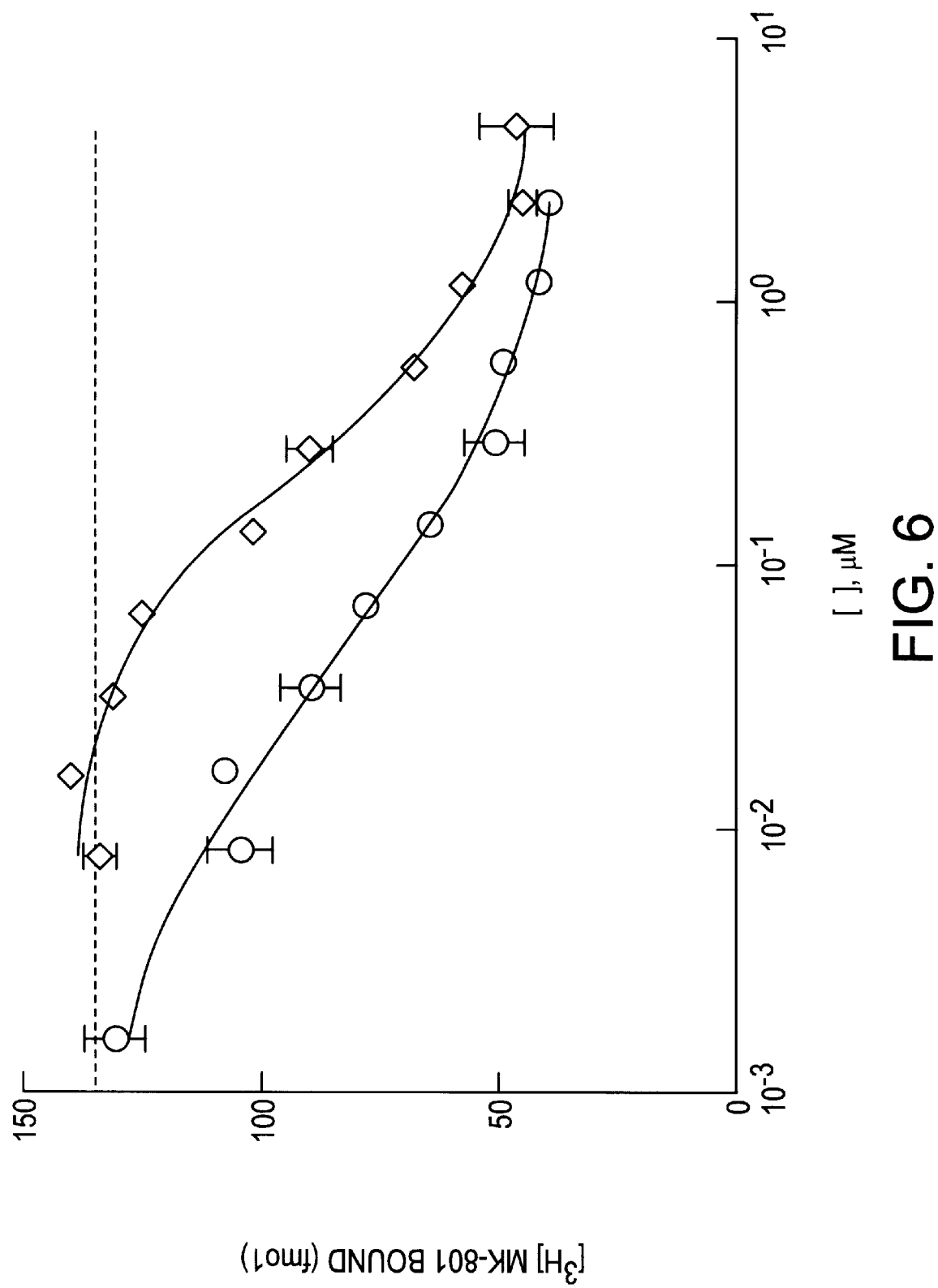
FIG. 6 depicts the inhibition of spermine-enhanced [$^3$H] MK-801 binding by Ala7-Con-G and Con-G.

In FIG. 6, concentration-response curves were obtained in the presence of 12.5 (opened symbols) and 25 (filled symbols) μM spermine, respectively. The symbols in FIG. 6 are as follows: open circles, Ala7-Con-G; open diamonds, Con-G; and dotted line, spermine alone. The results shown are from a typical experiment performed in duplicate, in which IC$_{50}$ values of Ala7-Con- G and Con-G were 50 and 275 nM, respectively. Moreover, the apparent IC$_{50}$. of Ala7-Con-G was unaffected by spermine concentrations. Both features were consistent with non-competitive antagonism.

Figure 7:
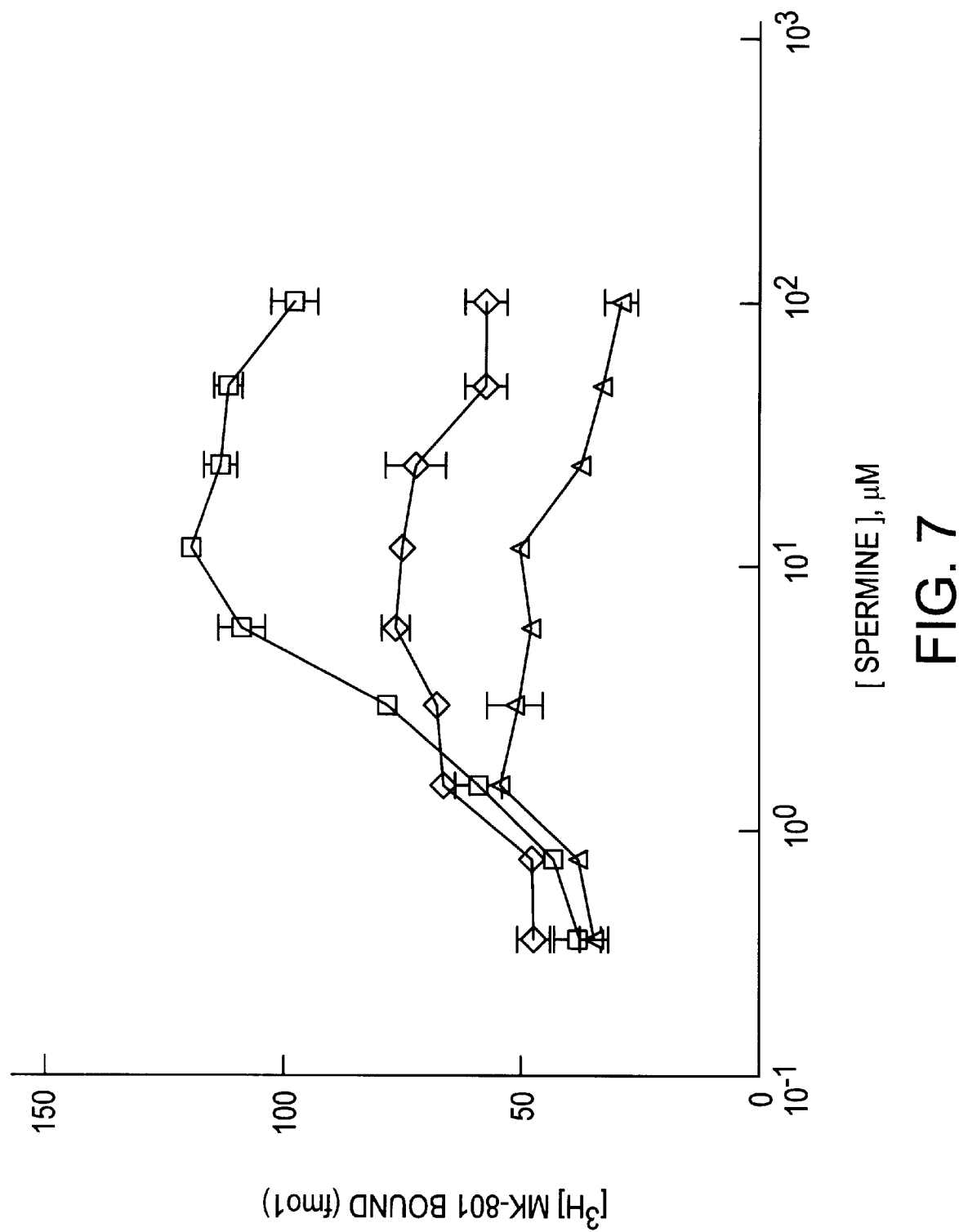
FIG. 7 depicts the non-competitive, concentration dependent, inhibition of spermine enhanced binding of [$^3$H]MK-801 by Ala7-Con-G.

At 10 nM, Ala7-Con-G inhibited about 50% of the maximum stimulation produced by spermine, and the concentration-response curve of spermine was reduced almost to baseline values by a concentration of 30 nM Ala7-Con-G. Results are depicted in FIG. 7. Non-competitive inhibition of polyamine-enhanced [$^3$H]MK-801 binding by Ala7 is shown. Spermine-enhanced [$^3$H]MK-801 binding was determined in the presence of 0 (squares), 10 (diamonds), and 30 nM Ala7-Con-G (triangles), respectively. The results shown were from a typical experiment in duplicate and were repeated with similar results.

TABLE I

Con G Peptides

| SEQ ID NO.: | SEQUENCE | DESIGNATION | |
|---|---|---|---|
| SEQ ID NO: 1 | GEggLQgNQgLIRgKSN | ConantokinG | |
| Class I - Amino Terminal Extensions/Modifications | | | |
| SEQ ID No: 4 | Ac-GEggLQgNQgLIRgKSN | Ac-Con-G | |
| SEQ ID No: 13 | AcY-GEggLQgNQgLIRgKSN | Ac-Tyr°-Con-G | |
| SEQ ID No: 14 | N-GEggLQgNQgLIRgKSN | Asn°-Con-G | |
| SEQ ID No: 15 | N(GIc0c)-GEggLQgNQgLIRgKSN | Asn(GlcN Ac)°-Con-G | |
| SEQ ID No: 16 | F-GEggLQgNQgLIRgKSN | Phe°-Con-G | |
| SEQ ID No: 17 | F(pCl)-GEggLQgNQgLIRgKSN | Phe(pCl)°-Con-G | |
| SEQ ID No: 18 | Y(p)-GEggLQgNQgLIRgKSN | Tyr(p)°-Con-G | |
| SEQ ID No: 19 | Y(oMe)-GEggLQgNQgLIRgKSN | Tyr(oMe)°-Con-G | |
| SEQ ID No: 3 | Y-GEggLQgNQgLIRgKSN | Tyr°-Con-G | |
| SEQ ID No: 20 | tBu-Y-GEggLQgNQgLIRgKSN | tBu-Tyr°-Con-G | |
| SEQ ID No: 21 | S-GEggLQgNQgLIRgKSN | Ser°-Con-G | |
| Class II - Internal Substitutions | | | |
| SEQ ID No: 5 | GEEELQENQELIREKSN | Glu3,4,7,10,14-Con-G | (Glu-Con-G) |
| SEQ ID No: 11 | GdEdEdELQdENQdELIRdEKSN | D-Glu3,4,7,10,14-Con-G | (D-Glu-Con-G) |

TABLE I-continued

Con G Peptides

| SEQ ID NO.: | SEQUENCE | DESIGNATION |
|---|---|---|
| SEQ ID No: 6 | Y-GEEELQENQELIREKSN | Tyr°-Glu3,4,7,10,14-Con-G |
| SEQ ID No: 22 | GEAgLQgNQgLIRgKSN | Ala3-Con-G |
| SEQ ID No: 23 | GESgLQgNQgLIRgKSN | Ser3-Con-G |
| SEQ ID No: 24 | GES(p)gLQgNQgLIRgKSN | Ser(p)3-Con-G |
| SEQ ID No: 25 | GEYgLQgNQgLIRgKSN | Tyr3-Con-G |
| SEQ ID No: 26 | GEgELQgNQgLIRgKSN | Glu4-Con-G |
| SEQ ID No: 27 | GEgALQgNQgLIRgKSN | Ala4-Con-G |
| SEQ ID No: 28 | GEgSLQgNQgLIRgKSN | Ser4-Con-G |
| SEQ ID No: 29 | GEgS(p)LQgNQgLIRgKSN | Ser(p)4-Con-G |
| SEQ ID No: 30 | GEggYQgNQgLIRgKSN | Tyr5-Con-G |
| SEQ ID No: 31 | GEggLQYNQgLIRgKSN | Tyr7-Con-G |
| SEQ ID No: 53 | GEggLQY(I)NQgLIRgKSN | iodo-Tyr7-Con-G |
| SEQ ID No: 54 | GEggLQY(II)NQgLIRgKSN | di-iodo-Tyr7-Con-G |
| SEQ ID No: 32 | GEggLQANQgLIRgKSN | Ala7-Con-G |
| SEQ ID No: 33 | GEggLQSNQgLIRgKSN | Ser7-Con-G |
| SEQ ID No: 34 | GEggLQS(p)NQgLIRgKSN | Ser(p)7-Con-G |
| SEQ ID No: 35 | GEggLQgNQALIRgKSN | Ala10-Con-G |
| SEQ ID No: 36 | GEggLQgNQSLIRgKSN | Ser10-Con-G |
| SEQ ID No: 37 | GEggLQgNQS(p)LIRgKSN | Ser(p)10-Con-G |
| SEQ ID No: 38 | GEggLQgNQgLIRAKSN | Ala 14-Con-G |
| SEQ ID No: 39 | GEggLQgNQgLIRSKSN | Ser14-Con-G |
| SEQ ID No: 40 | GEggLQgNQgLIRS(p)KSN | Ser(p) 14-Con-G |
| SEQ ID No: 41 | GEggLQENQELIREKSN | Glu,7,10,14-Con-G |
| SEQ ID No: 42 | GEggLQANQALIRAKSN | Ala 7,10,14-Con-G |
| SEQ ID No: 55 | GEggLQSNVSQIRAKSN | 3$_{10}$ helix ConG |
| SEQ ID No: 56 | GEggLQAALALIRAKSN | alpha helix ConG |
| SEQ ID No: 65: | GEggL-cyclic | cyclic ConG(1–5) |
| SEQ ID No: 57 | GEggL-gKSN | ConG(1–5)(14–17) |
| SEQ ID No: 58 | GEggL-GG-gKSN | ConG(1–5)GG(14–17) |
| SEQ ID No: 59 | GEggL-GGGG-gKSN | ConG(1–5)GGGG(14–17) |
| SEQ ID No: 60 | GEggL-AA-gKSN | ConG(1–5)AA(14–17) |
| SEQ ID No: 61 | GEggL-AAA-gKSN | ConG(1–5)AAAA(14–17) |
| SEQ ID No: 62 | GEggLQ-AAAAA-gKSN | ConG(1–6)A5(14–17) |
| SEQ ID No: 63 | GEggLQ-AAAAAAA-gKSN | ConG(1–6)A7(14–17) |
| SEQ ID No: 64 | GEggL-BB-gKSN | ConG(1–5)BB(14–17) |

Class III - Carboxy Terminal Fragments/Modifications

| SEQ ID No: 7 | IREKSN | Glu 14-Con-G(12–17) |
|---|---|---|
| SEQ ID No: 43 | IREASN | Glu 14-Ala 15-Con-G(12–17) |
| SEQ ID No: 44 | IAEKSN | Ala 13, Glu 14-Con-G(12–17) |
| SEQ ID No: 45 | IAEASN | Ala 13, 15, Glu 14-Con-G(12–17) |
| SEQ ID No: 8 | QELIREKSN | Glu 10,14-Con-G(9–17) |
| SEQ ID No: 9 | QENQELIREKSN | Glu 7,10,14-Con-G(6–17) |
| SEQ ID No: 10 | EEELQENQELIREKSN | Glu 3,4,7,10,14-Con-G(2–17) |
| SEQ ID No: 46 | IRgKSN | Con-G(12–17) |
| SEQ ID No: 47 | RSgNK | scrambled Con-G(13–17) |
| SEQ ID No: 48 | RgKSN | Con-G(13–17) |
| SEQ ID No: 49 | gKSN | Con-G(14–17) |
| SEQ ID No: 50 | IRgK | Con-G(12–15) |
| SEQ ID No: 51 | KSN | Con-G(15–17) |

Class IV - Amino Terminal Fragments/Modifications

| SEQ ID No: 2 | GEggLQgNQgLIRgKSN-OH | Con-G-OH |
|---|---|---|
| SEQ ID No: 52 | GEggL | Con-G(1–5) |

TABLE II

| Structure | EC (µM) | Spermine % Sti | IC (µM) | % Inh |
|---|---|---|---|---|
| Spermine | 4.5 | 100 | 0 | 0 |
| Spermidine | 10.8 | 97 | 0 | 0 |
| Mg$^{2+}$ | 20.6 | 52 | 0 | 0 |
| ConantokinG | 0 | 0 | 0.16 | 100 |
| SEQ ID No: 1 | | | | |
| Class I - Amino Terminal Extensions/Modifications | | | | |
| SEQ ID NO: 4 Ac-Con-G | 0 | 0 | 0 | 0 |
| SEQ ID NO: 13 Ac-Tyr°-Con-G | 0 | 0 | 18.3 | 73 |
| SEQ ID NO: 14 Asn°-Con-G | 0 | 0 | 8.7 | 83 |
| SEQ ID NO: 15 Asn(GlcNAc)°-Con-G | 0 | 0 | 8.8 | 38 |
| SEQ ID NO: 16 Phe°-Con-G | 6.8 ± 1.6 | 53 ± 17 | 6.1 | 51 |

TABLE II-continued

| Structure | | EC ($\mu$M) | Spermine % Sti | IC ($\mu$M) | % Inh | |
|---|---|---|---|---|---|---|
| SEQ ID NO: 17 | Phe(pCl)°-Con-G | 0 | 0 | 0 | 0 | |
| SEQ ID NO: 18 | Tyr(p)°-Con-G | 0 | 0 | 0 | 0 | |
| SEQ ID NO: 19 | Tyr(oMe)°-Con-G | 0 | 0 | 0 | 0 | |
| SEQ ID NO: 3 | Tyr°-Con-G | 0 | 0 | 0 | 0 | |
| SEQ ID NO: 20 | tBu-Tyr°-Con-G | 1.0 | 69 | 1.5 | 29 | |
| SEQ ID NO: 21 | Ser°-Con-G | 0 | 0 | 6.8 | 41 | |
| Class II- Internal Substitutions | | | | | | |
| SEQ ID NO: 5 | Glu3,4,7,10,14-Con-G (Glu-Con-G) | 6.7 | 79 | 8.5 | 22 | |
| SEQ ID NO: 11 | D-Glu3,4,7,10,14-Con-G (D-Glu-Con-G) | 5.8 | 30 | 0 | 0 | |
| SEQ ID NO: 6 | Tyr°-Glu3,4,7,10,14-Con-G | 2.7 | 31 | 0 | 0 | |
| SEQ ID NO: 22 | Ala3-Con-G | 0 | 0 | 1.8 ± 0.1 | 34 ± 9 | |
| SEQ ID NO: 23 | Ser3-Con-G | 8.4 ± 1.6 | 62 ± 4.9 | 3.6 ± 0.7 | 23 ± 3.6 | |
| SEQ ID NO: 24 | Ser(p)3-Con-G | 3.5 ± 1.9 | 68 ± 8.4 | 0.9 ± 0.09 | 34 ± 2.3 | |
| SEQ ID NO: 25 | Tyr3-Con-G | 0 | 0 | 0 | 0 | |
| SEQ ID NO: 26 | Glu4-Con-G | 0 | 0 | 0 | 0 | |
| SEQ ID NO: 27 | Ala4-Con-G | 0 | 0 | 0 | 0 | |
| SEQ ID NO: 28 | Ser4-Con-G | 0 | 0 | 0 | 0 | |
| SEQ ID NO: 29 | Ser(p)4-Con-G | 0 | 0 | 0 | 0 | |
| SEQ ID NO: 31 | Tyr7-Con-G | 0 | 0 | 0.5 | 100 | |
| SEQ ID NO: 53 | iodo-Tyr7-Con-G | 0 | 0 | 0.5 | 100 | |
| SEQ ID NO: 54 | di-iodo-Tyr7-Con-G | 0 | 0 | 0.5 | 100 | |
| SEQ ID NO: 32 | Ala7-Con-G | 0 | 0 | 0.046 | 100 | |
| SEQ ID NO: 33 | Ser7-Con-G | 0 | 0 | 0.25 ± 0.04 | 100 | |
| SEQ ID NO: 34 | Ser(p)7-Con-G | 0 | 0 | 1.04 ± 0.3 | 50 ± 3.8 | |
| SEQ ID NO: 35 | Ala10-Con-G | 0 | 0 | 1.10 ± 0.3 | 100 | |
| SEQ ID NO: 36 | Ser10-Con-G | 0 | 0 | 1.80 ± 0.2 | 100 | |
| SEQ ID NO: 37 | Ser(p)10-Con-G | 0 | 0 | 0.56 ± 0.2 | 100 | |
| SEQ ID NO: 38 | Ala14-Con-G | 0 | 0 | 0.16 ± 0.03 | 100 | |
| SEQ ID NO: 39 | Ser14-Con-G | 0 | 0 | 0.16 ± 0.04 | 100 | |
| SEQ ID NO: 40 | Ser(p)14-Con-G | 0 | 0 | 1.12 ± 0.05 | 31 ± 0.5 | |
| SEQ ID NO: 41 | Glu7,10,14-Con-G | 0 | 0 | >5 | 70 | 4 |
| SEQ ID NO: 42 | Ala7,10,14-Con-G | 0 | 0 | 0.5 | 100 | 4 |
| SEQ ID No: 55 | $3_{10}$ helix ConG | 0 | 0 | 20 | 25 | 3 |
| SEQ ID No: 56 | alpha helix ConG | 0 | 0 | 1.5 | 100 | 5 |
| SEQ ID No: 57 | ConG(1–5)(14–17) | 0 | 0 | 100 | 15 | 2 |
| SEQ ID No: 58 | ConG(1–5)GG(14–17) | 0 | 0 | | | 1 |
| SEQ ID No: 59 | ConG(1–5)GGGG(14–17) | 0 | 0 | | | 1 |
| SEQ ID No: 60 | ConG(1–5)AA(14–17) | 0 | 0 | | | 3 |
| SEQ ID No: 61 | ConG(1–5)AAAA(14–17) | 0 | 0 | | | 3 |
| SEQ ID No: 62 | ConG(1–6)A5(14–17) | 0 | 0 | | | 3–4 |
| SEQ ID No: 63 | ConG(1–6)A7(14–17) | 0 | 0 | | | 4–5 |
| SEQ ID No: 64 | ConG(1–5)BB(14–17) | 0 | 0 | 15 | 25 | 2–3 |
| Class III - Carboxy Terminal Fragments/Modifications | | | | | | |
| SEQ ID NO: 7 | Glu14-Con-G(12–17) | 47 | 30 | 0 | 0 | |
| SEQ ID NO: 43 | Glu 14, Ala15-Con-G(12–17) | | | inactive | | |
| SEQ ID NO: 44 | Ala13, Glu14-Con-G(12–17) | | | inactive | | |
| SEQ ID NO: 45 | Ala13,15, Glu14-Con-G(12–17) | | | inactive | | |
| SEQ ID NO: 8 | Glu10,14-Con-G(9–17) | 0 | 0 | 0 | 0 | |
| SEQ ID NO: 9 | Glu 7,10,14-Con-G (6–17) | 0 | 0 | 0 | 0 | |
| SEQ ID NO: 10 | Glu3,4,7,10-Con-G(2–17) | 0.9 | 33 | 5.4 | 70 | |
| SEQ ID NO: 46 | Con-G(12–17) | 58 | 20 | 0 | 0 | |
| SEQ ID NO: 47 | scrambled Con-G | | | inactive | | |
| SEQ ID NO: 48 | Con-G(13–17) | | | inactive | | |
| SEQ ID NO: 49 | Con-G(14–17) | 1.3 ± 0.6 | 61 ± 1.3 | 0 | 0 | |
| SEQ ID NO: 50 | Con-G(12–15) | 69.75 | ~20 | 0 | 0 | |
| SEQ ID NO: 51 | Con-G(15–17) | 61.72 | ~20 | 0 | 0 | |
| Class IV - Amino Terminal Fragments/Modifications | | | | | | |
| SEQ ID NO: 2 | Con-G-OH | 0 | 0 | 0 | 0 | |
| SEQ ID NO: 52 | Con-G(1–5) | 0 | 0 | 7.43 | 50 | |
| SEQ ID NO: 65 | Cyclic ConG(1–5) | | | inactive | | |

EXAMPLE 3

Con G Derivatives Exhibiting Partial Agonist Activity.

Figure 8:
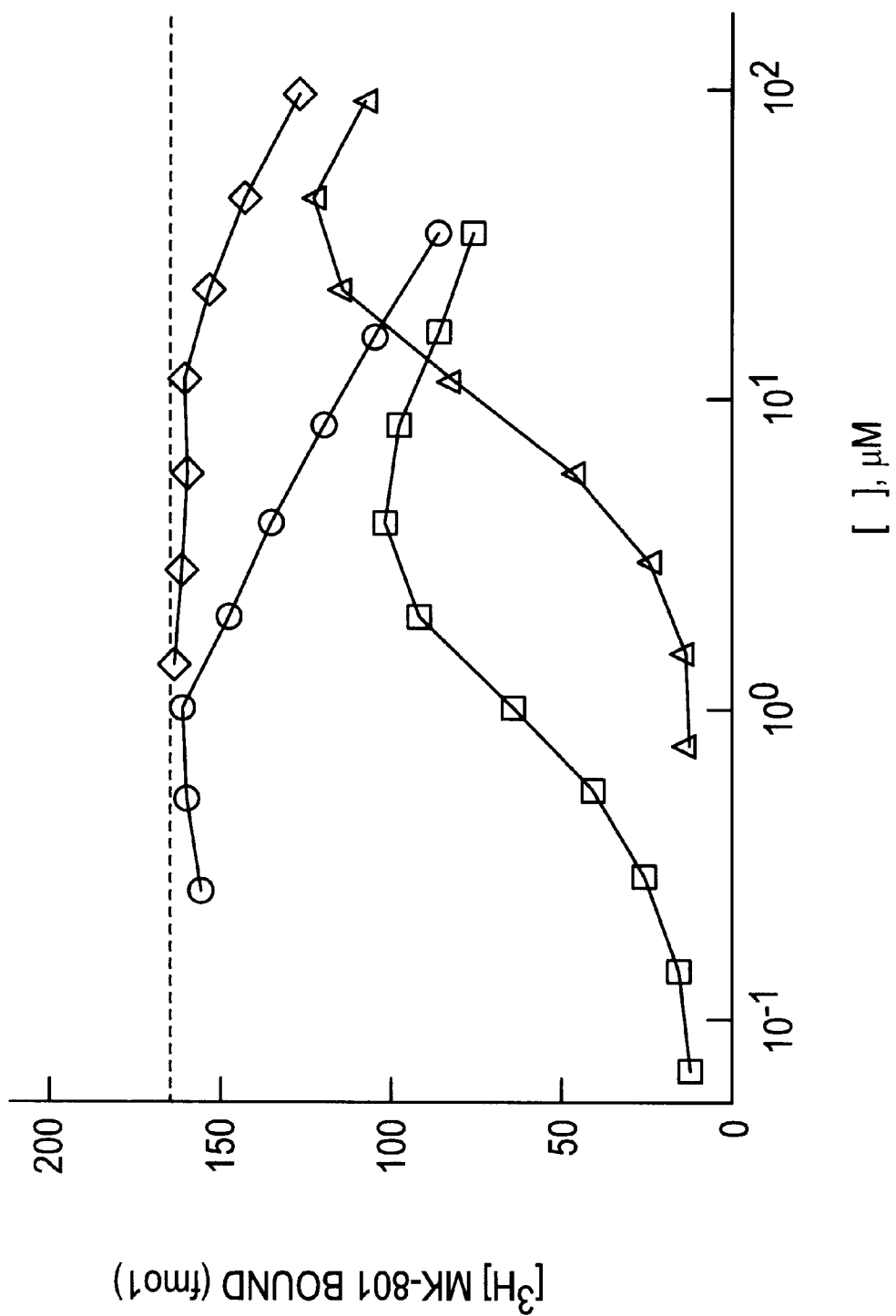
FIG. 8 depicts the partial agonist properties of Glu-Con-G and tBu-Tyr$^0$ -Con-G.

As indicated in Table II, several of the derivatives exhibited partial agonist activity. The results for two of these, tBu-Tyr°-Con-G and Glu-Con-G, are depicted in FIG. 8. In FIG. 8, the dotted line represents the level of binding achieved with a maximally effective concentration of spermine, i.e., 25 $\mu$M. The top two curves depict that, at higher concentrations, Glu-Con-G (diamonds) and tBu-Tyr$^0$-Con-G (circles) are antagonistic to spermine induced enhancement of [$^3$H]MK-801 binding. Although Glu-Con-G and tBu-Tyr$^0$-Con-G exhibit antagonism (top curves) to polyamine enhanced [$^3$H]MK-801 binding at higher concentrations, the levels of such antagonism are nowhere near those characteristic of the native Con-G. In fact, a concentration of tBu-$Tyr^0$-Con-G one order of magnitude greater than that of Con-G is required to obtain the same decrease as Con-G. The concentration of Glu-Con-G required is one order of magnitude greater than that of tBu-$Tyr^0$-Con-G. The bottom two curves of FIG. 8 depict that, in the absence of spermine, both Glu-Con-G (triangles) and tBu-$Tyr^0$-Con-G (squares) are agonists which enhance [$^3$H]MK-801 binding in a concentration-dependent manner.

Figure 9:
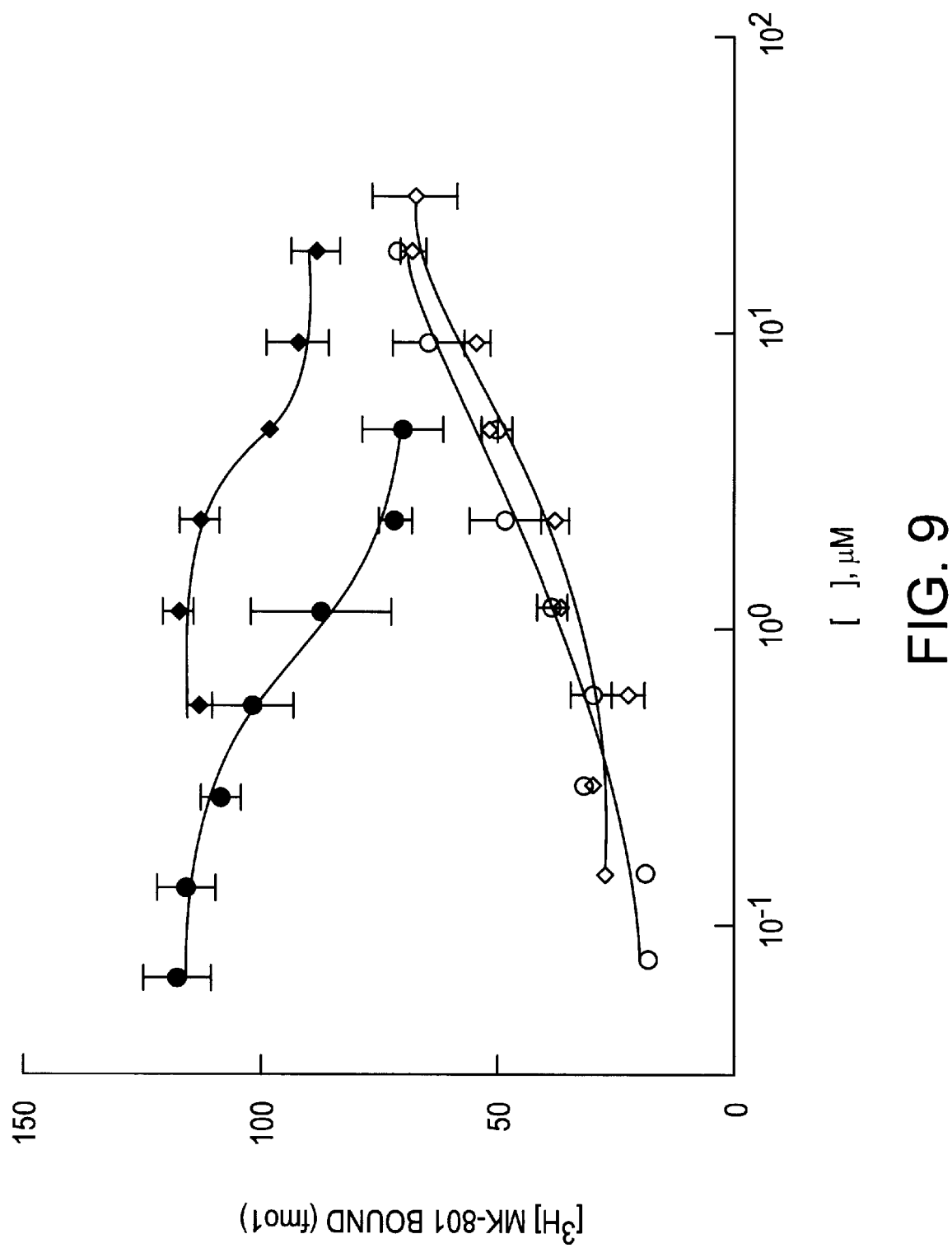
FIG. 9 depicts the partial agonist properties of Ser3-Con-G and Ser(p)3-Con-G.
Figure 10:
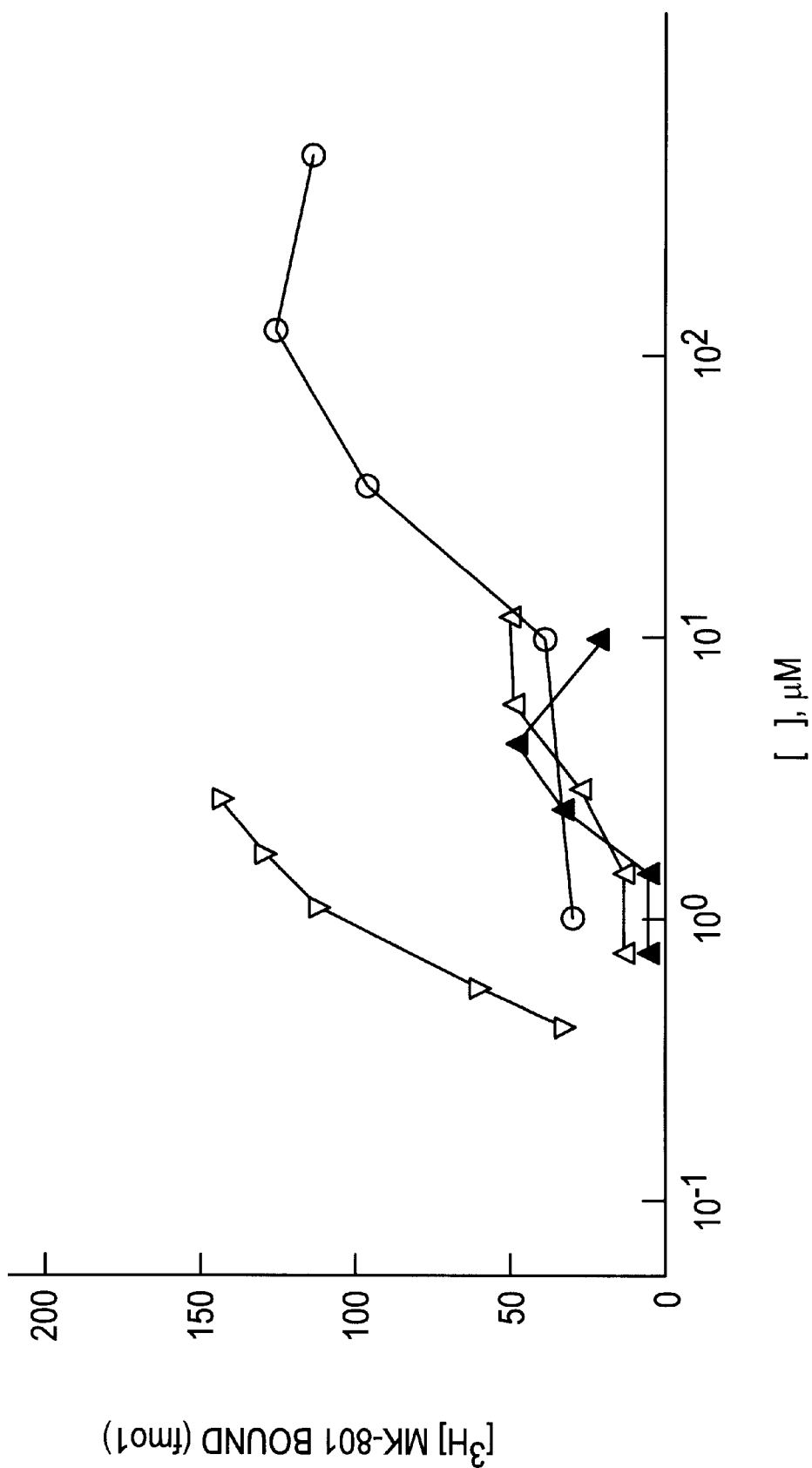
FIG. 10 depicts the agonistic effects of Con-G(14–17), Tyr$^0$ -Glu-Con-G, and Glu 14(12–17)-Con-G.
Figure 11:
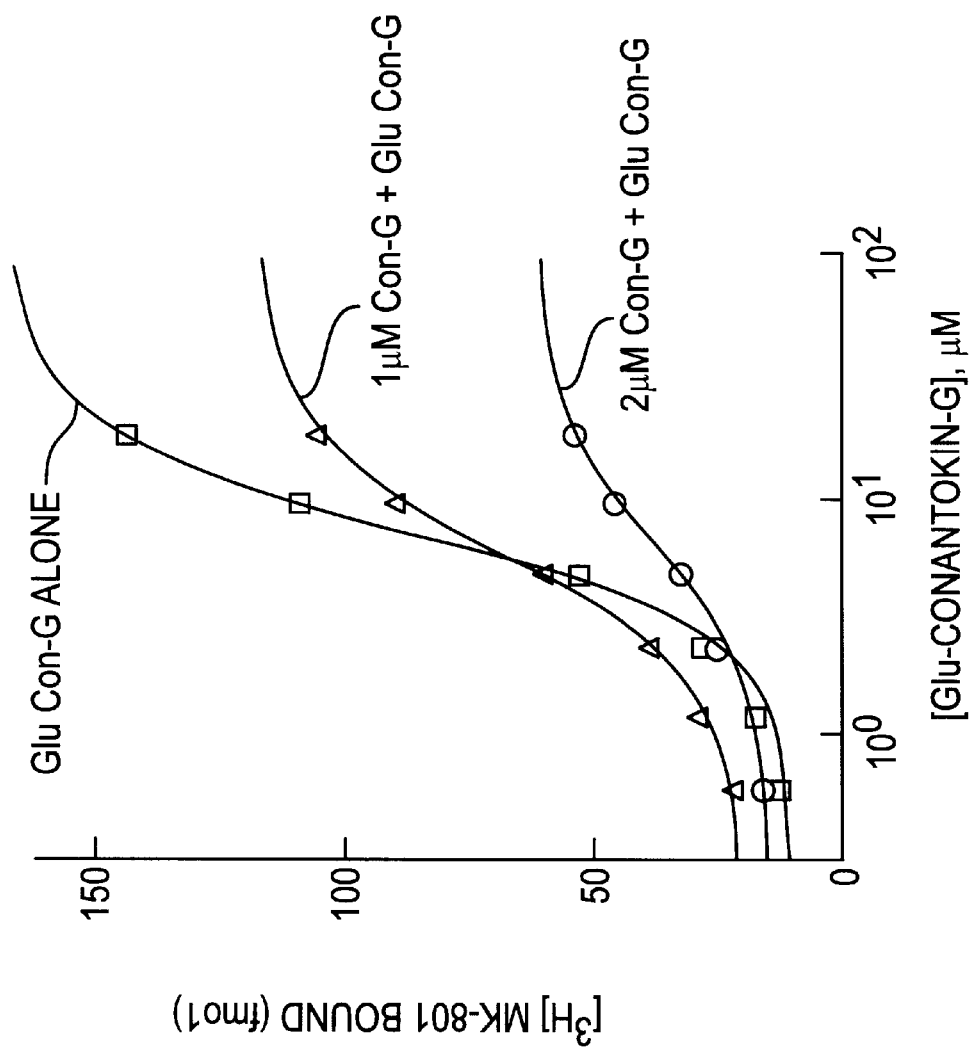
FIG. 11 depicts the noncompetitive inhibition of Glu Con-G enhanced [$^3$H]MK-801 binding to well-washed brain membranes by increasing concentrations of Con-G.
Figure 12:
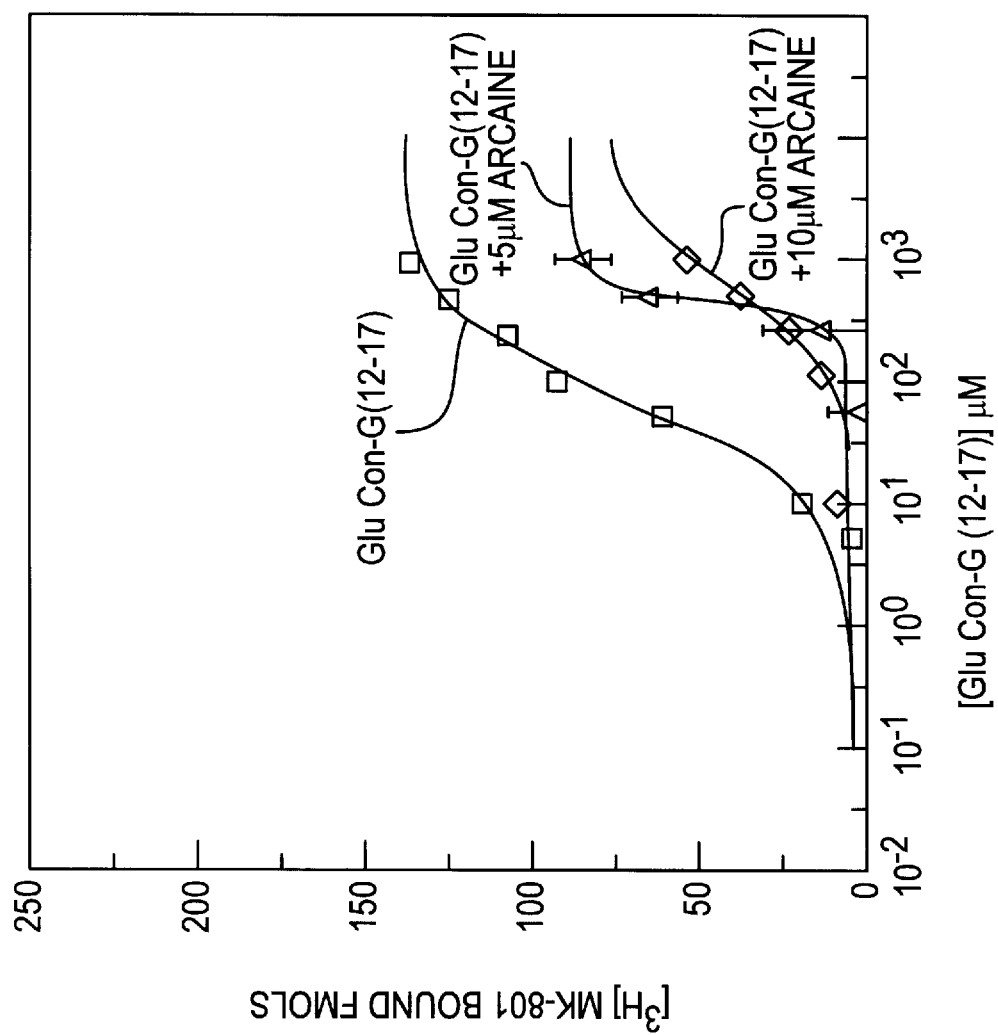
FIG. 12 depicts the interaction between Glu-Con-G (12–17) and arcaine.

In addition to Glu-Con-G and tBu-$Tyr^0$-Con-G, several other derivatives of Con-G show similar concentration dependent enhancements of [$^3$H]MK-801 binding in the absence of polyamines. Ser3-Con-G and Ser(p)3-Con-G inhibited spermine-enhanced (12.5 $\mu$M) [$^3$H]MK-801 binding to 73 and 65% of the maximum values, with $IC_{50}$ values of 3.6±0.7 (n=3) and 0.9±0.09 $\mu$M (n=3), respectively. This is depicted in FIG. 9: Ser3-Con-G, filled diamonds; Ser(p) 3-Con-G, filled circles. In the absence of spermine, Ser3-Con-G and Ser(p)3-Con-G stimulation of [$^3$H]MK-801 binding (open diamonds and open circles, respectively). Ser3-Con-G and Ser(p)3-Con-G increased [$^3$H]MK-801 binding with potencies similar to that of spermine, but significantly less efficacious. Glu-Con-G(2–17) and $Phe^0$-Con-G also exhibited partial agonist activity. The partial agonists, as presently ascertained, are summarized in Table III below. $EC_{50}$ and $IC_{50}$. values are reported in micromolar concentrations. Standard errors of the mean are provided when available.

TABLE III

| Structure | $EC_{50}$ | % STI | $IC_{50}$ | % INH |
|---|---|---|---|---|
| $Phe^0$-Con-G | 6.8 ± 1.6 | 53 ± 17 | 6.1 | 51 |
| tBu-$Tyr^0$-Con-G | 1.0 | 69 | 1.5 | 29 |
| Ser3-Con-G | 8.4 ± 1.6 | 62 ± 4.90 | 3.6 ± 0.7 | 23 ± 3.6 |
| Ser(p) 3-Con-G | 3,5 ± 1.9 | 68 ± 8.4 | 0.9 ± 0.09 | 34 ± 2.3 |
| Glu-Con-G | 6.7 | 79 | 8.5 | 22 |
| Glu3,4,7,10,14- | 0.9 | 33 | 5.4 | 70 |

EXAMPLE 4

Con G Derivatives Exhibiting Full Agonist Activity

Figure 16:
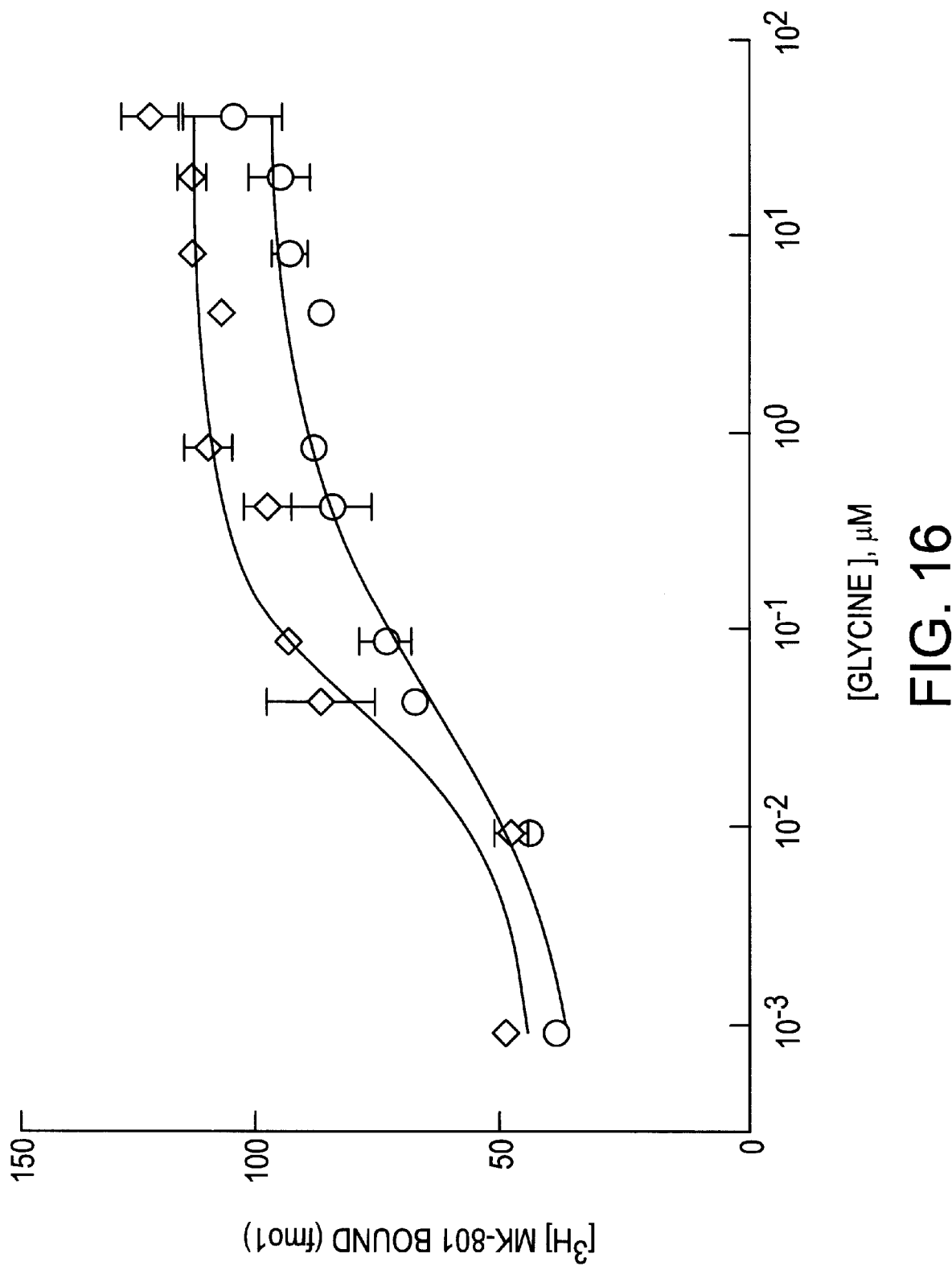
FIG. 16 depicts the effects of Ala7-Con-G on Gly-enhanced [$^3$ H]MK-801 binding.

The derivatives were tested for their effect on [$^3$H]MK-801 in the absence of spermine to determine whether any of the compounds exhibited agonistic properties for the NMDA receptor. All the compounds with agonistic activities are active in this assay.

As depicted in FIG. 10, Con-G(14–17) (inverted triangles), $Tyr^0$-Glu-Con-G (filled triangles), D-Glu-Con-G (open triangles), and Glu-Con-G(12–17) (circles) stimulated [$^3$H]MK-801 binding in the absence of spermine. These derivatives exhibited no inhibition of spermine-induced [$^3$H] MK-801 binding.

EXAMPLE 5

Binding Site Studies.

As Con-G, ifenprodil also inhibits polyamine binding in a non-competitive manner. It does not appear, however, that Con-G acts at the same site as ifenprodil since Con-G slightly increases, while ifenprodil decreases (Reynolds et al., supra ), [$^3$H]MK-801 binding in the nominal absence of Gly and Glu. Further, ifenprodil inhibits Glu enhanced [$^3$H]MK-801 binding, while as shown in FIG. 1, and discussed below, even at very high concentrations, Con-G does not appear to affect Glu stimulation.

Spermine (at a concentration of up to 1000 $\mu$M) lacks the ability to reverse the antagonistic effects of both Con-G and Ala7-Con-G on NMDA-stimulated cyclic GMP formation. This observation is in agreement with non-competitive inhibition seen in radioligand binding assays, indicating that the polyamines and Con-G do not compete at the same binding site on the NMDA receptor complex.

Con-G does, however, inhibit Glu-Con-G stimulated [$^3$H] MK-801 binding. This suggests that derivatives of Con-G exhibiting agonist activity are binding at the polyamine site. The results are depicted in FIG. 11. In FIG. 11, squares represent Glu-Con-G alone; triangles represent Glu-Con-G with 1 $\mu$M Con-G; and circles represent Glu-Con-G with 2 $\mu$M Con-G.

Further evidence that the Con-G derivatives exhibiting agonist activity act at the polyamine site is given by their interactions with arcaine, a competitive inhibitor of the polyamine site. The results with Glu-Con-G(12–17) are depicted in FIG. 12. In FIG. 12, squares represent Glu-Con-G(12–17) stimulation of [$^3$H]MK-801 binding; triangles represent the effect of 5 $\mu$M arcaine on Glu-Con-G(12–17) stimulated [$^3$H]MK-801 binding; and diamonds represent the effect of 10 $\mu$M arcaine on Glu-Con-G(12–17) stimulated [$^3$H]MK-801 binding.

FIG. 13 depicts the effect of increasing concentrations of Con-G upon Gly- and Glu-stimulated [$^3$H]MK-801 binding to the brain membrane preparation (triangles represent Con-G plus 10 $\mu$M Glu; diamonds represent Con-G plus 10 $\mu$M Gly; and circles represent Con-G alone). As can be seen, Con-G has no affect upon Glu stimulation and, in fact, the Glu stimulation is additive with that produced by Con-G alone. Con-G does slightly inhibit Gly stimulation at concentrations greater than 5 $\mu$M. Radioligand binding studies with [$^3$H]CGP39653 confirmed that Con-G and its derivative Ala7 had no actions at Glu binding site. To ascertain whether Con-G acts as a competitive inhibitor at the Gly site, the effect of 10 $\mu$M Con-G on Gly stimulated [$^3$H]MK-801 binding to the membrane preparation was determined. The results are depicted in FIG. 14. In FIG. 14, triangles represent Gly alone; squares represent Gly with 10 $\mu$M Con-G. Con-G modestly inhibits Gly enhanced [$^3$H]MK-801 binding by about 15% with no remarkable effect on its potency. The dotted line represents a theoretical binding curve if the combination of Con-G and Gly was additive. As can be seen in FIG. 14, Con-G does not inhibit the Gly stimulation in a manner consistent with competitive inhibition. Therefore, Con-G does not appear to be a competitive inhibitor of the Gly site.

Similar results were obtained with the derivative Ala7-Con-G. Ala7-Con-G did not affect Glu-mediated increases in [$^3$H]MK-801 binding, but did antagonize Gly-mediated increases in [$^3$H]MK-801 binding. The results with Ala7-Con-G were obtained in the presence (triangles) or absence (circles) of Gluate and .are presented in FIG. 15*b*. However, at high concentrations, Con-G partially (~65%) and Ala7-Con-G fully antagonized the binding of [$^3$H]MK-801 produced by Gly (10 $\mu$M) with $IC_{50}$ values of 513±72 (n=3) and 858±133 nM (n=3), respectively. These results are depicted in FIG. 15*a*. In FIG. 15*a*, circles represent Con-G; diamonds represent Ala7-Con-G; the dotted line represents maximum Gly stimulated [$^3$H]MK-801 binding; and dashed line represents baseline Gly stimulated [$^3$H]MK-801 binding. In this representative experiment, the $IC_{50}$ values of Ala7-Con-G and Con-G are 625 and 835 nM, respectively.

At a concentration of 30 nM, Ala7-Con-G reduced the concentration-response curve of spermine to baseline values, whereas Gly-stimulated [$^3$H]MK-801 binding was only reduced by about 20% (FIG. 16: diamonds, Gly without Ala7-Con-G; circles, Gly with 30 nM Ala7-Con-G). The $EC_{50}$. values of Gly in this experiment were 56 and 58 nM in the presence and absence of Ala7, respectively. This experiment was repeated with similar results. The $IC_{50}$ value of Ala7 (~500 nM) required to reduce Gly stimulated [$^3$H]MK-801 binding was 10 times more than that required to reduce spermine stimulated [$^3$H]MK-801 binding (~45 nM).

Neither Con-G nor Ala7-Con-G affected the binding of [$^3$H]5, 7-dichlorokynurenic acid (DCK), which is a specific radioligand for the strychnine-insensitive Gly site on the NMDA receptor complex, [$^3$H] CGS39753, a radioligand specific for the Gluate site, or [$^3$H] Ifrenprodil, an NMDA antagonist acting at a polyamine-sensitive site. These results are summarized in Table IV below. $IC_{50}$ values are reported in $\mu$M concentration.

TABLE IV

| Example | [$^3$H]-CGS39753 | [$^3$H]DCK | [$^3$H]IFENPRODIL |
|---|---|---|---|
| Con-G | $\mu$5 pM | >5 $\mu$M | >5 $\mu$M |
| Ala7-Con-G | >2.5 $\mu$M | >2.5 $\mu$M | 2.5 $\mu$M |

In contrast, the inhibitory effects of Con-G (up to 2.5 $\mu$M) and Ala7-ConG (up to 2.5 $\mu$M) on spermine-, Gly-, and spermine-Gly-enhanced increases in [$^3$H]MK-801 binding were abolished in the presence of 10 $\mu$M Gluate.

The inhibition of Gly effects by Ala7-Con-G and Con-G might be produced through the allosteric interaction of spermine associated site and Gly site on the NMDA receptor complex. Consistent with these conclusions, there is some evidence that has been reported suggesting that the polyamines increase receptor response by increasing the apparent affinity of Gly at the strychnine-insensitive Gly site. It is, therefore, possible that the modest reduction of Gly stimulation is attributable to Con-G inhibition of some remaining endogenous polyamines in the washed brain membranes.

EXAMPLE 6

Con G Derivatives with Modified Helical Cores

Figure 17:
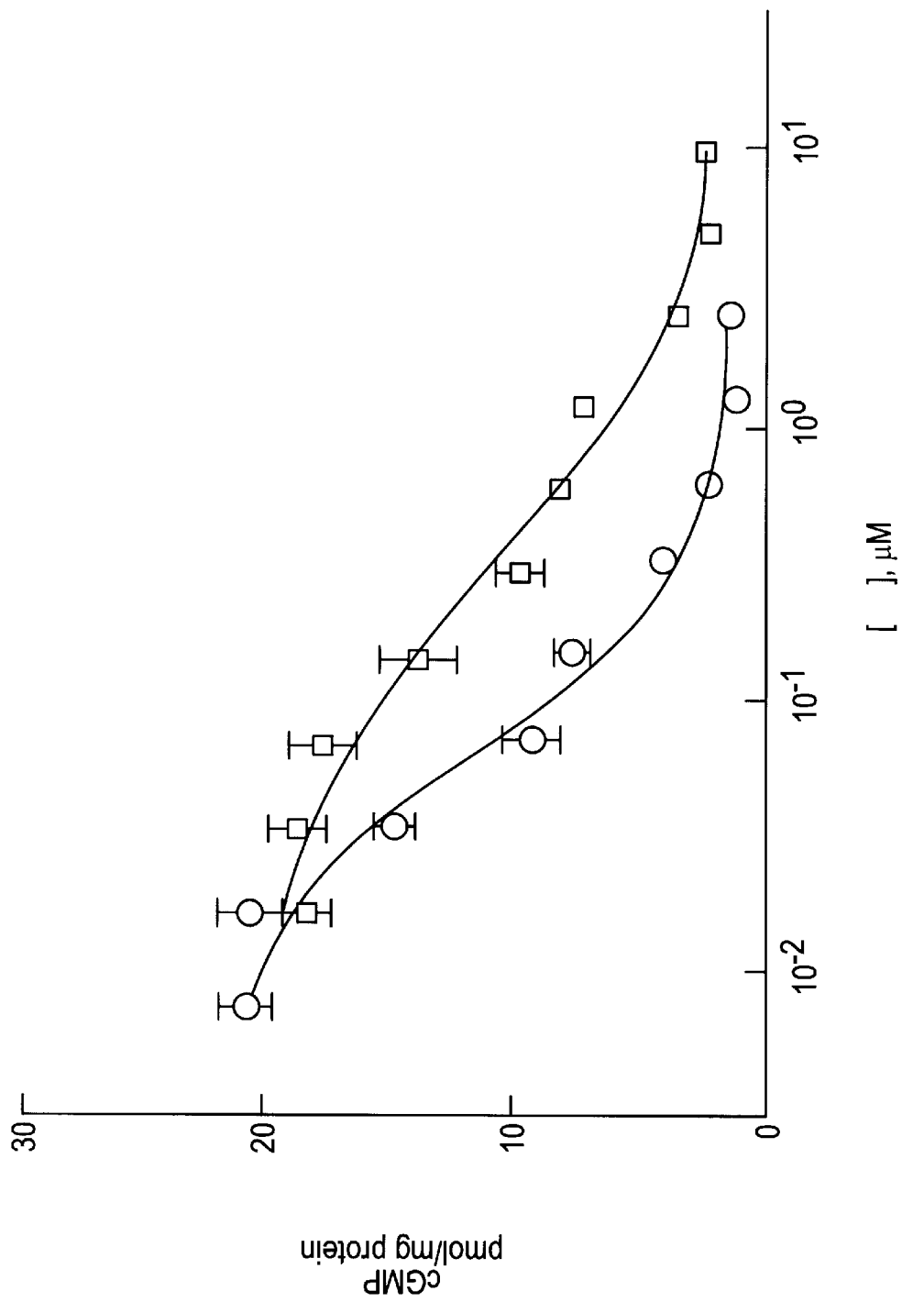
FIG. 17 depicts the effects of Con-G and Ala7-Con-G on NMDA-stimulated cyclic GMP level in primary cultures of cerebellar granule cells.

The structure of the 17 amino acid Con-G isolated from snail was determined by NMR, CD and IR to have a stiff helical core spanning amino acid residues 7 to 13. This helical core is flanked by two flexible end pieces, a 6 amino acid long amino terminal piece and a 4 amino acid long carboxy terminal piece. Extensive structure activity data on Con-G analogues which have a full spectrum of activities ranging from antagonism through partial agonism/ antagonism to full Results Ala7-Con-G inhibited NMDA-stimulated increases in cyclic GMP formation in primary cultures of granule cells with an $IC_{50}$ value of 77±7.5 nM (n=4), 4-fold (p<0.01) greater than that of Con-G ($IC_{50}$ 300±30 nM, n=5) under the same conditions, without altering kainate (50 $\mu$M)- mediated effects (up to 2.5 $\mu$M). The results are depicted in FIG. 17. In this representative experiment, Con-G (squares) and Ala7-Con-G (circles) inhibited NMDA (100 $\mu$M) stimulated increases in cyclic GMP with $IC_{50}$ values of 332 and 78 nM, respectively (data represent the means ± SEM of triplicate values).

EXAMPLE 8

Protection Against Neurotoxicity

Evaluation of Neurotoxicity

Preparation of Cerebellar Granule Cells

Primary cultures of cerebellar granule cells were prepared from 6–8 day old Sprague-Dawley rats by the method of Gallo et al., "Selective release of glutamate from cerebellar granule cells differentiating in culture," Proc. Nat'l Acad. Sci. USA, 29:7010–7023, 1982, incorporated herein by reference. Dissociated cells were resuspended in Eagle's Basal Medium (Gibco, Grand Island, N.Y.) with 10% fetal calf serum (Quality Biological, Inc., Gaithersburg, MD), 2 mM 1-glutamine, 0.1 mg/ml gentamicin, and 25 mM KCl. (All remaining cell culture reagents were obtained from Sigma, Co., St. Louis, Mo.) The cells were seeded in 22–35 mm poly-L-lysine (10 $\mu$ml) coated dishes at a density of 1.8–3.8×10$^5$ cells/cm$^2$. Cytosine arabinoside (10 $\mu$M) was added 18 to 24 hours after plating to inhibit the growth of non-neuronal cells. Cultures generated by this method contained ≧90% granule cell neurons. The medium was not changed during the culture period. Cells were incubated at 37° C. in humidified 95% air/5% $CO_2$ atmosphere.

Determination of Neurotoxicity

Experiments were performed using cells cultured for 9 days. The culture medium was removed and the granule cells were washed twice with 1.5 ml of incubation buffer (160.6 mM NaCl, 5.6 mM KCl, 2.3 mM $CaCl_2$, and 8.6 mM HEPES, Ph 7.4-Locke buffer without magnesium or glucose). The cells were preincubated in 1 ml of buffer for 25 minutes at 37° C. Following a change of buffer, test compounds were added to the appropriate cultures and incubated for an additional 15 minutes (37° C.). The buffer was changed again, and Glu (100 $\mu$M) was added together with Con-G (0.1–5 $\mu$M), MK-801 (10 $\mu$M), or vehicle. Thirty minutes later, the buffer was removed, the cells washed twice with 1.5 ml of complete Locke buffer (154 mM NaCl, 5.6 mM KCl, 2.3 mM $CaCl_2$, 5.6 mM glucose, 8.6 mM HEPES, 1–0 Mm $MgCl_2$, pH 7.4), and the cells incubated for 18–24 hours in 1 ml of culture medium. Cell death was determined using trypan blue. Cell death and neuroprotection were calculated by the following equations:

% cytotoxicity=D/(D+L)×100;

% protection=100−(% cytotoxicity)

where "D" equals the number of dead cells counted in three different random fields using 400× bright field microscopy, and "L" equals the number of live cells counted in the same three fields.

Figure 18:
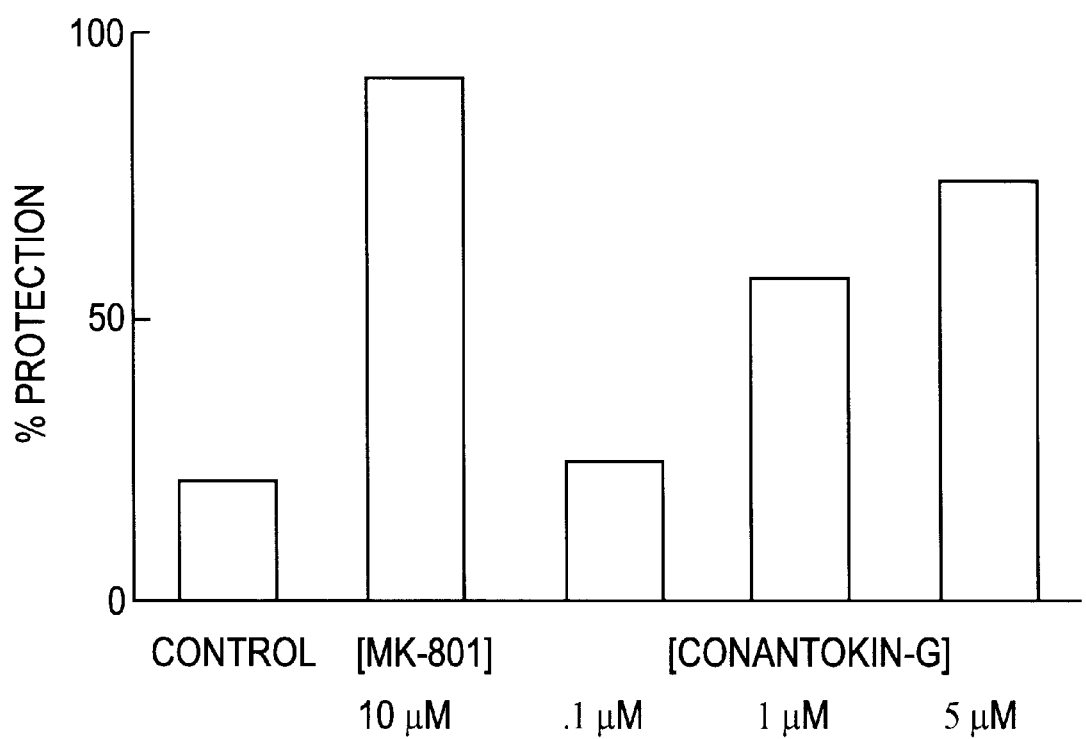
FIG. 18 depicts the neuroprotective effect, as percentage protection, of MK-801 and Con-G on glutamate induced cell death (neurotoxicity) in cerebellar granule cell cultures.

FIG. 18 documents that Con-G may be used to protect cells from excitotoxic death (resulting from excess $Ca^{++}$ influx) induced by Glu over-stimulation of the NMDA receptor. In FIG. 18, the protective effect of Con-G and MK-801 on cerebellar granule cell cultures was measured in response to a neurotoxicity induced with a 100 $\mu$M concentration of Glu. Con-G's action at the Con-G site is sufficient to reduce the flow of $Ca^{++}$ to substantially protect the cells from excitotoxic death. In fact, the protection achieved with 5 $\mu$M Con-G is comparable to that obtained with 10 $\mu$M MK-801. Since Con-G does not actually block the channel, it is not expected to produce the dramatic long term effects seen with the channel blocking compounds. Thus, Con-G's action in allosterically modulating the response of the polyamine site acts to modulate the overall response of the NMDA receptor.

EXAMPLE 9

Determination of Subtype Specific Binding.

The various compounds can be utilized in assays for determining compounds which bind the novel Con-G site, or portions thereof. For example, some of the derivatives prepared bind at the Con site alone, whereas others bind to the polyamine site alone. Still others, like Con-G, bind to both. Labelled compounds representative of each group—full antagonists, partial agonists, and full agonists—can be used to ascertain other compounds with similar binding characteristics.

Inhibition of Polyamine Stimulation of the NR1/NR2b Subtype

Con-G was found to be specific for one subtype of the NMDA receptor, the NR1/NR2b subtype. As described in Kutsuwada et al., Nature, 358:36–41 (1992), the disclosure of which is incorporated herein by reference, NR2a, NR2b and NR2c subunit-specific mRNAs were synthesized in vitro from cloned cDNA and injected in Xenopus oocytes together with the NR1 subunit-specific MnRNA. The peak inward currents obtained in normal frog Ringer's solution at −70mV membrane potential were 300 nA in response to 10 $\mu$M L-Glu plus 10 $\mu$M Gly and 100 $\mu$M NMDA plus 10 $\mu$M Gly. They were about the same for oocytes injected with all three subunit combinations. The current amplitudes were much larger than those for oocytes implanted with the NR1 subunit alone. Also oocytes injected with the NR2 subunit-specific mRNAs alone exhibited no detectable response (<1 nA).

Neither 100 $\mu$M kainate nor 100 $\mu$M AMPA evoked a measurable response of oocytes injected with the NR1 and NR2 subunits. Addition of polyamines had no effect on inward current in the NR1/NR2a and NR1/NR2c subunit injected oocytes, but increased the amplitude in the NR1/NR2b transformed oocytes by about 30%. This data is consistent with the finding that polyamines act on the NR1/NR2b subtype of the NMDA receptor. Igarashi et al., J. Pharm. Exp. Ther., 272:1101–1109 (1995).

Figure 19:
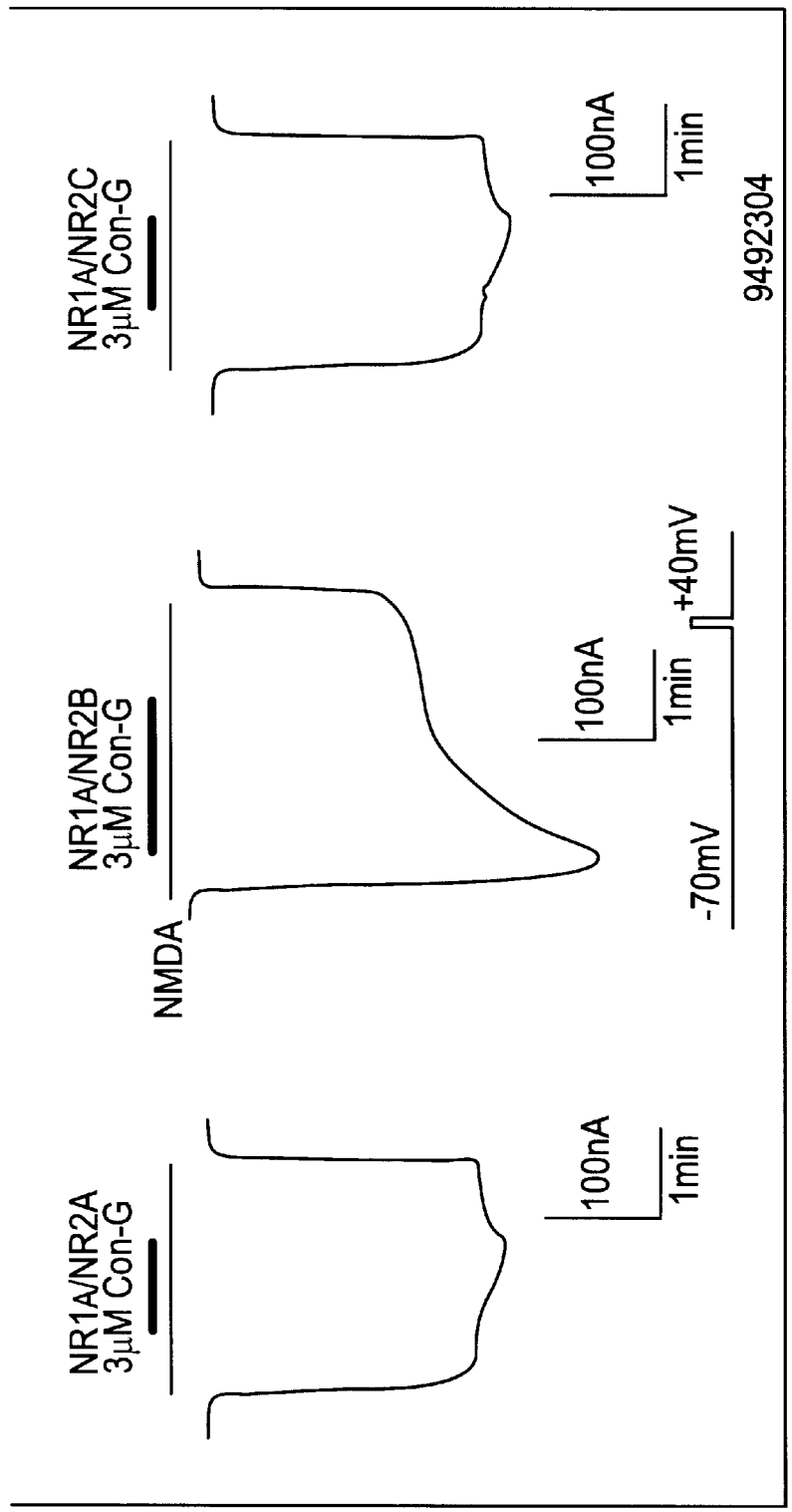
FIG. 19 depicts the specific inhibitory effect of ConG (3 $\mu$M) on polyamine stimulation of the NR1/NR2a, NR1/NR2b, and NR1/NR2c subtypes of the NMDA receptor, measured as, the change in potential.
Figure 20:
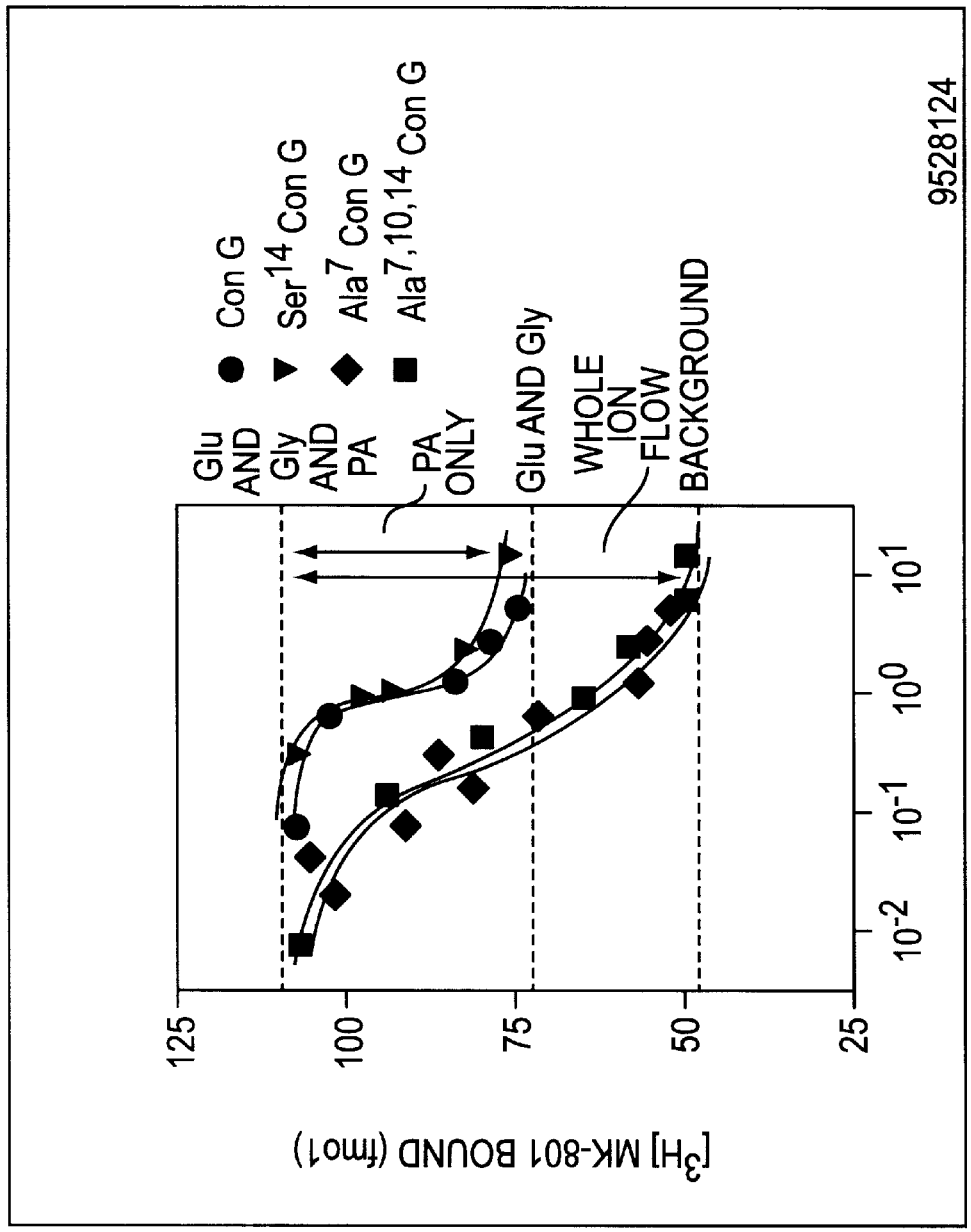
FIG. 20 depicts the relative antagonism of ConG and analogs, represented as concentration of [$^3$H]MK-801 bound (fmol) for Con G (circle), Ser$^{14}$ Con G (inverted triangle), Ala$^7$ Con G (diamond), and Ala$^{7,10,14}$ Con G (square).

Current responses of polyamine stimulated Xenopus oocytes injected with the heteromeric NRl1/NR2a, NR1/NR2b, NR1/NR2c NMDA receptor subunits to ConG were examined. As illustrated in FIG. 19, subunit-specific effects of spermine and ConG were measured by inducing currents with L-Glu and Gly (10 $\mu$M each) in oocytes voltage-clamped at −70 $\mu$M and expressing the NR1/NR2a, NR1/NR2b and the NR1/NR2c receptors in the presence of 10 $\mu$M spermine. 3 $\mu$M ConG was applied during the times shown by the horizontal bar in FIG. 19. Addition of ConG at 3 $\mu$M had no effect on currents through the NR1/NR2a and NR1/NR2c receptor, but inhibited the polyamine stimulation on the NR1/NR2b receptor subtype. This shows that ConG is the first and only polyamine specific inhibitor in as far as its capability to inhibit polyamine stimulated ion flow.

ConG and analogs and mimetics thereof thus can be used as probes for examining the physiology and role of polyamines on the NR1/NR2b subtype of the NMDA receptor in neuropsychoparmacological disorders, and for the development of clinically effective drugs. Modified peptides and mimetic molecules can be designed which have a preselected affinity and activity as well as which have enhanced stability and bioavailability.

Although the invention has been described with reference to Con-G and specific Con-G derivatives, the details should not be construed as limitations on the invention. Rather, various equivalents, modifications, and other derivatives as would be obvious to one skilled in the art upon learning of the invention and without departing from the spirit and scope of the invention as presented in the appended claims are included. All references cited herein are hereby incorporated herein by reference.

What is claimed is:

1. A method for treating excitotoxicity resulting from over-stimulation of the NMDA receptor which comprises administering to a patient in need thereof a therapeutically effective amount of Conantokin-G or a pharmaceutically acceptable salt thereof.

2. The method of claim 1, wherein said excitotoxicity is associated with epilepsy or epileptic seizure.

* * * * *

```
                          SEQUENCE LISTING (1) GENERAL INFORMATION:

(iii) NUMBER OF SEQUENCES: 65

(2) INFORMATION FOR SEQ ID NO:1:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 7
        (D) OTHER INFORMATION: /note= "Amino acid 7 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:1:

Gly Glu Xaa Xaa Leu Gln Xaa Asn Gln Xaa Leu Ile Arg Xaa Lys
1               5                   10                  15

Ser Asn (2) INFORMATION FOR SEQ ID NO:2:
```

```
        (i) SEQUENCE CHARACTERISTICS:
             (A) LENGTH: 17 amino acids
             (B) TYPE: amino acid
             (D) TOPOLOGY: linear (ii) MOLECULE TYPE: protein (iii) HYPOTHETICAL: NO (ix) FEATURE:
             (A) NAME/KEY: Modified-site
             (B) LOCATION: 3
             (D) OTHER INFORMATION: /note= "Amino acid 3 is
                 gamma-carboxyglutamate (Gla)"

(ix) FEATURE:
             (A) NAME/KEY: Modified-site
             (B) LOCATION: 4
             (D) OTHER INFORMATION: /note= "Amino acid 4 is
                 gamma-carboxyglutamate (Gla)"

(ix) FEATURE:
             (A) NAME/KEY: Modified-site
             (B) LOCATION: 7
             (D) OTHER INFORMATION: /note= "Amino acid 7 is
                 gamma-carboxyglutamate (Gla)"

(ix) FEATURE:
             (A) NAME/KEY: Modified-site
             (B) LOCATION: 10
             (D) OTHER INFORMATION: /note= "Amino acid 10 is
                 gamma-carboxyglutamate (Gla)"

(ix) FEATURE:
             (A) NAME/KEY: Modified-site
             (B) LOCATION: 14
             (D) OTHER INFORMATION: /note= "Amino acid 14 is
                 gamma-carboxyglutamate (Gla)"

(xi) SEQUENCE DESCRIPTION: SEQ ID NO:2:

Gly Glu Xaa Xaa Leu Gln Xaa Asn Gln Xaa Leu Ile Arg Xaa Lys
1               5                   10                  15

Ser Asn (2) INFORMATION FOR SEQ ID NO:3:

(i) SEQUENCE CHARACTERISTICS:
             (A) LENGTH: 18 amino acids
             (B) TYPE: amino acid
             (D) TOPOLOGY: linear (ii) MOLECULE TYPE: protein (iii) HYPOTHETICAL: NO (ix) FEATURE:
             (A) NAME/KEY: Modified-site
             (B) LOCATION: 4
             (D) OTHER INFORMATION: /note= "Amino acid 4 is
                 gamma-carboxyglutamate (Gla)"

(ix) FEATURE:
             (A) NAME/KEY: Modified-site
             (B) LOCATION: 5
             (D) OTHER INFORMATION: /note= "Amino acid 5 is
                 gamma-carboxyglutamate (Gla)"

(ix) FEATURE:
             (A) NAME/KEY: Modified-site
             (B) LOCATION: 8
             (D) OTHER INFORMATION: /note= "Amino acid 8 is
                 gamma-carboxyglutamate (Gla)"

(ix) FEATURE:
             (A) NAME/KEY: Modified-site
```

```
            (B) LOCATION: 11
            (D) OTHER INFORMATION: /note= "Amino acid 11 is
                gamma-carboxyglutamate (Gla)"

(ix) FEATURE:
            (A) NAME/KEY: Modified-site
            (B) LOCATION: 15
            (D) OTHER INFORMATION: /note= "Amino acid 15 is
                gamma-carboxyglutamate (Gla)"

(ix) FEATURE:
            (A) NAME/KEY: Modified-site
            (B) LOCATION: 18
            (D) OTHER INFORMATION: /note= "Amino acid 18 has an
                amidated terminus"

(xi) SEQUENCE DESCRIPTION: SEQ ID NO:3:

Tyr Gly Glu Xaa Xaa Leu Gln Xaa Asn Gln Xaa Leu Ile Arg Xaa
1               5                   10                  15

Lys Ser Asn (2) INFORMATION FOR SEQ ID NO:4:

(i) SEQUENCE CHARACTERISTICS:
            (A) LENGTH: 17 amino acids
            (B) TYPE: amino acid
            (D) TOPOLOGY: linear (ii) MOLECULE TYPE: protein (iii) HYPOTHETICAL: NO (ix) FEATURE:
            (A) NAME/KEY: Modified-site
            (B) LOCATION: 1
            (D) OTHER INFORMATION: /note= "Amino acid 1 is
                acetylated"

(ix) FEATURE:
            (A) NAME/KEY: Modified-site
            (B) LOCATION: 3
            (D) OTHER INFORMATION: /note= "Amino acid 3 is
                gamma-carboxyglutamate (Gla)"

(ix) FEATURE:
            (A) NAME/KEY: Modified-site
            (B) LOCATION: 4
            (D) OTHER INFORMATION: /note= "Amino acid 4 is
                gamma-carboxyglutamate (Gla)"

(ix) FEATURE:
            (A) NAME/KEY: Modified-site
            (B) LOCATION: 7
            (D) OTHER INFORMATION: /note= "Amino acid 7 is
                gamma-carboxyglutamate (Gla)"

(ix) FEATURE:
            (A) NAME/KEY: Modified-site
            (B) LOCATION: 10
            (D) OTHER INFORMATION: /note= "Amino acid 10 is
                gamma-carboxyglutamate (Gla)"

(ix) FEATURE:
            (A) NAME/KEY: Modified-site
            (B) LOCATION: 14
            (D) OTHER INFORMATION: /note= "Amino acid 14 is
                gamma-carboxyglutamate (Gla)"

(ix) FEATURE:
            (A) NAME/KEY: Modified-site
            (B) LOCATION: 17
            (D) OTHER INFORMATION: /note= "Amino acid 17 has an
                amidated terminus"

(xi) SEQUENCE DESCRIPTION: SEQ ID NO:4:
```

```
Gly Glu Xaa Xaa Leu Gln Xaa Asn Gln Xaa Leu Ile Arg Xaa Lys
1               5                   10                  15

Ser Asn
```

(2) INFORMATION FOR SEQ ID NO:5:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:5:

```
Gly Glu Glu Glu Leu Gln Glu Asn Gln Glu Leu Ile Arg Glu Lys
1               5                   10                  15

Ser Asn
```

(2) INFORMATION FOR SEQ ID NO:6:

(i) SEQUENCE CHARACTERISTICS:
        (A) LENGTH: 18 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 18
        (D) OTHER INFORMATION: /note= "Amino acid 18 has an
            amidated terminus"

(xi) SEQUENCE DESCRIPTION: SEQ ID NO:6:

```
Tyr Gly Glu Glu Glu Leu Gln Glu Asn Gln Glu Leu Ile Arg Glu
1               5                   10                  15

Lys Ser Asn
```

(2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 6
        (D) OTHER INFORMATION: /note= "Amino acid 6 has an
            amidated terminus"

(xi) SEQUENCE DESCRIPTION: SEQ ID NO:7:

```
Ile Arg Glu Lys Ser Asn
1               5
```

```
(2) INFORMATION FOR SEQ ID NO:8:

(i) SEQUENCE CHARACTERISTICS:
        (A) LENGTH: 9 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 9
        (D) OTHER INFORMATION: /note= "Amino acid 9 has an
             amidated terminus"

(xi) SEQUENCE DESCRIPTION: SEQ ID NO:8:

Gln Glu Leu Ile Arg Glu Lys Ser Asn
1               5

(2) INFORMATION FOR SEQ ID NO:9:

(i) SEQUENCE CHARACTERISTICS:
        (A) LENGTH: 12 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 12
        (D) OTHER INFORMATION: /note= "Amino acid 12 has an
             amidated terminus"

(xi) SEQUENCE DESCRIPTION: SEQ ID NO:9:

Gln Glu Asn Gln Glu Leu Ile Arg Glu Lys Ser Asn
1               5                  10

(2) INFORMATION FOR SEQ ID NO:10:

(i) SEQUENCE CHARACTERISTICS:
        (A) LENGTH: 16 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 16
        (D) OTHER INFORMATION: /note= "Amino acid 16 has an
             amidated terminus"

(xi) SEQUENCE DESCRIPTION: SEQ ID NO:10:

Glu Glu Glu Leu Gln Glu Asn Gln Glu Leu Ile Arg Glu Lys Ser
1               5                  10                  15
Asn (2) INFORMATION FOR SEQ ID NO:11:

(i) SEQUENCE CHARACTERISTICS:
        (A) LENGTH: 17 amino acids
        (B) TYPE: amino acid
        (D) TOPOLOGY: linear (ii) MOLECULE TYPE: protein
```

(iii) HYPOTHETICAL: NO (ix) FEATURE:
              (A) NAME/KEY: Modified-site
              (B) LOCATION: 2
              (D) OTHER INFORMATION: /note= "Amino acid 2 is
                  D-glutamate (D-Glu)"

(ix) FEATURE:
              (A) NAME/KEY: Modified-site
              (B) LOCATION: 3
              (D) OTHER INFORMATION: /note= "Amino acid 3 is
                  D-glutamate (D-Glu)"

(ix) FEATURE:
              (A) NAME/KEY: Modified-site
              (B) LOCATION: 4
              (D) OTHER INFORMATION: /note= "Amino acid 4 is
                  D-glutamate (D-Glu)"

(ix) FEATURE:
              (A) NAME/KEY: Modified-site
              (B) LOCATION: 7
              (D) OTHER INFORMATION: /note= "Amino acid 7 is
                  D-glutamate (D-Glu)"

(ix) FEATURE:
              (A) NAME/KEY: Modified-site
              (B) LOCATION: 10
              (D) OTHER INFORMATION: /note= "Amino acid 10 is
                  D-glutamate (D-Glu)"

(ix) FEATURE:
              (A) NAME/KEY: Modified-site
              (B) LOCATION: 14
              (D) OTHER INFORMATION: /note= "Amino acid 14 is
                  D-glutamate (D-Glu)"

(ix) FEATURE:
              (A) NAME/KEY: Modified-site
              (B) LOCATION: 17
              (D) OTHER INFORMATION: /note= "Amino acid 17 has an
                  amidated terminus"

(xi) SEQUENCE DESCRIPTION: SEQ ID NO:11:

Gly Xaa Xaa Xaa Leu Gln Xaa Asn Gln Xaa Leu Ile Arg Xaa Lys
1               5                  10                  15

Ser Asn (2) INFORMATION FOR SEQ ID NO:12:

(i) SEQUENCE CHARACTERISTICS:
              (A) LENGTH: 21 amino acids
              (B) TYPE: amino acid
              (D) TOPOLOGY: linear (ii) MOLECULE TYPE: protein (iii) HYPOTHETICAL: NO (ix) FEATURE:
              (A) NAME/KEY: Modified-site
              (B) LOCATION: 3
              (D) OTHER INFORMATION: /note= "Amino acid 3 is
                  gamma-carboxyglutamate (Gla)"

(ix) FEATURE:
              (A) NAME/KEY: Modified-site
              (B) LOCATION: 4
              (D) OTHER INFORMATION: /note= "Amino acid 4 is
                  gamma-carboxyglutamate (Gla)"

(ix) FEATURE:
              (A) NAME/KEY: Modified-site
              (B) LOCATION: 10

(D) OTHER INFORMATION: /note= "Amino acid 10 is
                gamma-carboxyglutamate (Gla)"

(ix) FEATURE:
            (A) NAME/KEY: Modified-site
            (B) LOCATION: 14
            (D) OTHER INFORMATION: /note= "Amino acid 14 is
                gamma-carboxyglutamate (Gla)"

(ix) FEATURE:
            (A) NAME/KEY: Modified-site
            (B) LOCATION: 21
            (D) OTHER INFORMATION: /note= "Amino acid 21 has an
                amidated terminus"

(xi) SEQUENCE DESCRIPTION: SEQ ID NO:12:

Gly Glu Xaa Xaa Tyr Gln Lys Met Leu Xaa Asn Leu Arg Xaa Ala
1               5                   10                  15

Glu Val Lys Lys Asn Ala
                20

(2) INFORMATION FOR SEQ ID NO:13:

(i) SEQUENCE CHARACTERISTICS:
        (A) LENGTH: 18 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 1
        (D) OTHER INFORMATION: /note= "Amino acid 1 is
            acetylated"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 5
        (D) OTHER INFORMATION: /note= "Amino acid 5 is
            gamma-carboxyglutamate (Gla)"

(ix) FEATURE:
        (A) NAME/KEY: Modified-site
        (B) LOCATION: 8
        (D) OTHER INFORMATION: /note= "Amino acid 8 is
            gamma-carboxyglutamate (Gla)"

(ix) FEATURE:
        (A) NAME/KEY: Modified-site
        (B) LOCATION: 11
        (D) OTHER INFORMATION: /note= "Amino acid 11 is
            gamma-carboxyglutamate (Gla)"

(ix) FEATURE:
        (A) NAME/KEY: Modified-site
        (B) LOCATION: 15
        (D) OTHER INFORMATION: /note= "Amino acid 15 is
            gamma-carboxyglutamate (Gla)"

(ix) FEATURE:
        (A) NAME/KEY: Modified-site
        (B) LOCATION: 18
        (D) OTHER INFORMATION: /note= "Amino acid 18 has an
            amidated terminus"

(xi) SEQUENCE DESCRIPTION: SEQ ID NO:13:

-continued

```
Tyr Gly Glu Xaa Xaa Leu Gln Xaa Asn Gln Xaa Leu Ile Arg Xaa
1               5                   10                  15

Lys Ser Asn
```

(2) INFORMATION FOR SEQ ID NO:14:

(i) SEQUENCE CHARACTERISTICS:
        (A) LENGTH: 18 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 5
        (D) OTHER INFORMATION: /note= "Amino acid 5 is
            gamma-carboxyglutamate (Gla)"

(ix) FEATURE:
        (A) NAME/KEY: Modified-site
        (B) LOCATION: 8
        (D) OTHER INFORMATION: /note= "Amino acid 8 is
            gamma-carboxyglutamate (Gla)"

(ix) FEATURE:
        (A) NAME/KEY: Modified-site
        (B) LOCATION: 11
        (D) OTHER INFORMATION: /note= "Amino acid 11 is
            gamma-carboxyglutamate (Gla)"

(ix) FEATURE:
        (A) NAME/KEY: Modified-site
        (B) LOCATION: 15
        (D) OTHER INFORMATION: /note= "Amino acid 15 is
            gamma-carboxyglutamate (Gla)"

(ix) FEATURE:
        (A) NAME/KEY: Modified-site
        (B) LOCATION: 18
        (D) OTHER INFORMATION: /note= "Amino acid 18 has an
            amidated terminus"

(xi) SEQUENCE DESCRIPTION: SEQ ID NO:14:

```
Asn Gly Glu Xaa Xaa Leu Gln Xaa Asn Gln Xaa Leu Ile Arg Xaa
1               5                   10                  15

Lys Ser Asn
```

(2) INFORMATION FOR SEQ ID NO:15:

(i) SEQUENCE CHARACTERISTICS:
        (A) LENGTH: 18 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 1
        (D) OTHER INFORMATION: /note= "Amino acid 1 has
            N-acetylglucosamine"

(ix) FEATURE:

```
          (A) NAME/KEY: Modified-site
          (B) LOCATION: 4
          (D) OTHER INFORMATION: /note= "Amino acid 4 is
              gamma-carboxyglutamate (Gla)"

(ix) FEATURE:
          (A) NAME/KEY: Modified-site
          (B) LOCATION: 5
          (D) OTHER INFORMATION: /note= "Amino acid 5 is
              gamma-carboxyglutamate (Gla)"

(ix) FEATURE:
          (A) NAME/KEY: Modified-site
          (B) LOCATION: 8
          (D) OTHER INFORMATION: /note= "Amino acid 8 is
              gamma-carboxyglutamate (Gla)"

(ix) FEATURE:
          (A) NAME/KEY: Modified-site
          (B) LOCATION: 11
          (D) OTHER INFORMATION: /note= "Amino acid 11 is
              gamma-carboxyglutamate (Gla)"

(ix) FEATURE:
          (A) NAME/KEY: Modified-site
          (B) LOCATION: 14
          (D) OTHER INFORMATION: /note= "Amino acid 14 is
              gamma-carboxyglutamate (Gla)"

(ix) FEATURE:
          (A) NAME/KEY: Modified-site
          (B) LOCATION: 18
          (D) OTHER INFORMATION: /note= "Amino acid 18 has an
              amidated terminus"

(xi) SEQUENCE DESCRIPTION: SEQ ID NO:15:

Asn Gly Glu Xaa Xaa Leu Gln Xaa Asn Gln Xaa Leu Ile Arg Xaa
1               5                   10                  15

Lys Ser Asn (2) INFORMATION FOR SEQ ID NO:16:

(i) SEQUENCE CHARACTERISTICS:
          (A) LENGTH: 18 amino acids
          (B) TYPE: amino acid
          (D) TOPOLOGY: linear (ii) MOLECULE TYPE: protein (iii) HYPOTHETICAL: NO (ix) FEATURE:
          (A) NAME/KEY: Modified-site
          (B) LOCATION: 4
          (D) OTHER INFORMATION: /note= "Amino acid 4 is
              gamma-carboxyglutamate (Gla)"

(ix) FEATURE:
          (A) NAME/KEY: Modified-site
          (B) LOCATION: 5
          (D) OTHER INFORMATION: /note= "Amino acid 5 is
              gamma-carboxyglutamate (Gla)"

(ix) FEATURE:
          (A) NAME/KEY: Modified-site
          (B) LOCATION: 8
          (D) OTHER INFORMATION: /note= "Amino acid 8 is
              gamma-carboxyglutamate (Gla)"

(ix) FEATURE:
          (A) NAME/KEY: Modified-site
          (B) LOCATION: 11
          (D) OTHER INFORMATION: /note= "Amino acid 11 is
              gamma-carboxyglutamate (Gla)"

(ix) FEATURE:
```

(A) NAME/KEY: Modified-site
          (B) LOCATION: 14
          (D) OTHER INFORMATION: /note= "Amino acid 14 is
              gamma-carboxyglutamate (Gla)"

(ix) FEATURE:
          (A) NAME/KEY: Modified-site
          (B) LOCATION: 18
          (D) OTHER INFORMATION: /note= "Amino acid 18 has an
              amidated terminus"

(xi) SEQUENCE DESCRIPTION: SEQ ID NO:16:

Phe Gly Glu Xaa Xaa Leu Gln Xaa Asn Gln Xaa Leu Ile Arg Xaa
1               5                  10                  15

Lys Ser Asn (2) INFORMATION FOR SEQ ID NO:17:

(i) SEQUENCE CHARACTERISTICS:
          (A) LENGTH: 18 amino acids
          (B) TYPE: amino acid
          (D) TOPOLOGY: linear (ii) MOLECULE TYPE: protein (iii) HYPOTHETICAL: NO (ix) FEATURE:
          (A) NAME/KEY: Modified-site
          (B) LOCATION: 1
          (D) OTHER INFORMATION: /note= "Amino acid 1 is
              phosphochlorinated"

(ix) FEATURE:
          (A) NAME/KEY: Modified-site
          (B) LOCATION: 4
          (D) OTHER INFORMATION: /note= "Amino acid 4 is
              gamma-carboxyglutamate (Gla)"

(ix) FEATURE:
          (A) NAME/KEY: Modified-site
          (B) LOCATION: 5
          (D) OTHER INFORMATION: /note= "Amino acid 5 is
              gamma-carboxyglutamate (Gla)"

(ix) FEATURE:
          (A) NAME/KEY: Modified-site
          (B) LOCATION: 8
          (D) OTHER INFORMATION: /note= "Amino acid 8 is
              gamma-carboxyglutamate (Gla)"

(ix) FEATURE:
          (A) NAME/KEY: Modified-site
          (B) LOCATION: 11
          (D) OTHER INFORMATION: /note= "Amino acid 11 is
              gamma-carboxyglutamate (Gla)"

(ix) FEATURE:
          (A) NAME/KEY: Modified-site
          (B) LOCATION: 14
          (D) OTHER INFORMATION: /note= "Amino acid 14 is
              gamma-carboxyglutamate (Gla)"

(ix) FEATURE:
          (A) NAME/KEY: Modified-site
          (B) LOCATION: 18
          (D) OTHER INFORMATION: /note= "Amino acid 18 has an
              amidated terminus"

(xi) SEQUENCE DESCRIPTION: SEQ ID NO:17:

Phe Gly Glu Xaa Xaa Leu Gln Xaa Asn Gln Xaa Leu Ile Arg Xaa
1               5                  10                  15

Lys Ser Asn (2) INFORMATION FOR SEQ ID NO:18:

(i) SEQUENCE CHARACTERISTICS:
        (A) LENGTH: 18 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 1
        (D) OTHER INFORMATION: /note= "Amino acid 1 is
            phosphorylated"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 5
        (D) OTHER INFORMATION: /note= "Amino acid 5 is
            gamma-carboxyglutamate (Gla)"

(ix) FEATURE:
        (A) NAME/KEY: Modified-site
        (B) LOCATION: 8
        (D) OTHER INFORMATION: /note= "Amino acid 8 is
            gamma-carboxyglutamate (Gla)"

(ix) FEATURE:
        (A) NAME/KEY: Modified-site
        (B) LOCATION: 11
        (D) OTHER INFORMATION: /note= "Amino acid 11 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 18
        (D) OTHER INFORMATION: /note= "Amino acid 18 has an
            amidated terminus"

(xi) SEQUENCE DESCRIPTION: SEQ ID NO:18:

```
Tyr Gly Glu Xaa Xaa Leu Gln Xaa Asn Gln Xaa Leu Ile Arg Xaa
1               5                   10                  15

Lys Ser Asn
```

(2) INFORMATION FOR SEQ ID NO:19:

(i) SEQUENCE CHARACTERISTICS:
        (A) LENGTH: 18 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 1
        (D) OTHER INFORMATION: /note= "Amino acid 1 is
            methylated"

```
    (ix) FEATURE:
         (A) NAME/KEY: Modified-site
         (B) LOCATION: 4
         (D) OTHER INFORMATION: /note= "Amino acid 4 is
             gamma-carboxyglutamate (Gla)"

(ix) FEATURE:
         (A) NAME/KEY: Modified-site
         (B) LOCATION: 5
         (D) OTHER INFORMATION: /note= "Amino acid 5 is
             gamma-carboxyglutamate (Gla)"

(ix) FEATURE:
         (A) NAME/KEY: Modified-site
         (B) LOCATION: 8
         (D) OTHER INFORMATION: /note= "Amino acid 8 is
             gamma-carboxyglutamate (Gla)"

(ix) FEATURE:
         (A) NAME/KEY: Modified-site
         (B) LOCATION: 11
         (D) OTHER INFORMATION: /note= "Amino acid 11 is
             gamma-carboxyglutamate (Gla)"

(ix) FEATURE:
         (A) NAME/KEY: Modified-site
         (B) LOCATION: 14
         (D) OTHER INFORMATION: /note= "Amino acid 14 is
             gamma-carboxyglutamate (Gla)"

(ix) FEATURE:
         (A) NAME/KEY: Modified-site
         (B) LOCATION: 18
         (D) OTHER INFORMATION: /note= "Amino acid 18 has an
             amidated terminus"

(xi) SEQUENCE DESCRIPTION: SEQ ID NO:19:

Tyr Gly Glu Xaa Xaa Leu Gln Xaa Asn Gln Xaa Leu Ile Arg Xaa
1               5                   10                  15

Lys Ser Asn (2) INFORMATION FOR SEQ ID NO:20:

(i) SEQUENCE CHARACTERISTICS:
         (A) LENGTH: 18 amino acids
         (B) TYPE: amino acid
         (D) TOPOLOGY: linear (ii) MOLECULE TYPE: protein (iii) HYPOTHETICAL: NO (ix) FEATURE:
         (A) NAME/KEY: Modified-site
         (B) LOCATION: 1
         (D) OTHER INFORMATION: /note= "Amino acid 1 is
             t-butylated"

(ix) FEATURE:
         (A) NAME/KEY: Modified-site
         (B) LOCATION: 4
         (D) OTHER INFORMATION: /note= "Amino acid 4 is
             gamma-carboxyglutamate (Gla)"

(ix) FEATURE:
         (A) NAME/KEY: Modified-site
         (B) LOCATION: 5
         (D) OTHER INFORMATION: /note= "Amino acid 5 is
             gamma-carboxyglutamate (Gla)"

(ix) FEATURE:
         (A) NAME/KEY: Modified-site
         (B) LOCATION: 8
         (D) OTHER INFORMATION: /note= "Amino acid 8 is
             gamma-carboxyglutamate (Gla)"
```

```
    (ix) FEATURE:
         (A) NAME/KEY: Modified-site
         (B) LOCATION: 11
         (D) OTHER INFORMATION: /note= "Amino acid 11 is
             gamma-carboxyglutamate (Gla)"

(ix) FEATURE:
         (A) NAME/KEY: Modified-site
         (B) LOCATION: 14
         (D) OTHER INFORMATION: /note= "Amino acid 14 is
             gamma-carboxyglutamate (Gla)"

(ix) FEATURE:
         (A) NAME/KEY: Modified-site
         (B) LOCATION: 18
         (D) OTHER INFORMATION: /note= "Amino acid 18 has an
             amidated terminus"

(xi) SEQUENCE DESCRIPTION: SEQ ID NO:20:

Tyr Gly Glu Xaa Xaa Leu Gln Xaa Asn Gln Xaa Leu Ile Arg Xaa
1               5                  10                  15

Lys Ser Asn (2) INFORMATION FOR SEQ ID NO:21:

(i) SEQUENCE CHARACTERISTICS:
         (A) LENGTH: 18 amino acids
         (B) TYPE: amino acid
         (D) TOPOLOGY: linear (ii) MOLECULE TYPE: protein (iii) HYPOTHETICAL: NO (ix) FEATURE:
         (A) NAME/KEY: Modified-site
         (B) LOCATION: 4
         (D) OTHER INFORMATION: /note= "Amino acid 4 is
             gamma-carboxyglutamate (Gla)"

(ix) FEATURE:
         (A) NAME/KEY: Modified-site
         (B) LOCATION: 5
         (D) OTHER INFORMATION: /note= "Amino acid 5 is
             gamma-carboxyglutamate (Gla)"

(ix) FEATURE:
         (A) NAME/KEY: Modified-site
         (B) LOCATION: 8
         (D) OTHER INFORMATION: /note= "Amino acid 8 is
             gamma-carboxyglutamate (Gla)"

(ix) FEATURE:
         (A) NAME/KEY: Modified-site
         (B) LOCATION: 11
         (D) OTHER INFORMATION: /note= "Amino acid 11 is
             gamma-carboxyglutamate (Gla)"

(ix) FEATURE:
         (A) NAME/KEY: Modified-site
         (B) LOCATION: 14
         (D) OTHER INFORMATION: /note= "Amino acid 14 is
             gamma-carboxyglutamate (Gla)"

(ix) FEATURE:
         (A) NAME/KEY: Modified-site
         (B) LOCATION: 18
         (D) OTHER INFORMATION: /note= "Amino acid 18 has an
             amidated terminus"

(xi) SEQUENCE DESCRIPTION: SEQ ID NO:21:

Ser Gly Glu Xaa Xaa Leu Gln Xaa Asn Gln Xaa Leu Ile Arg Xaa
1               5                  10                  15

Lys Ser Asn
```

(2) INFORMATION FOR SEQ ID NO:22:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 7
        (D) OTHER INFORMATION: /note= "Amino acid 7 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:22:

```
Gly Glu Ala Xaa Leu Gln Xaa Asn Gln Xaa Leu Ile Arg Xaa Lys
1               5                   10                  15
Ser Asn
```

(2) INFORMATION FOR SEQ ID NO:23:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 7
        (D) OTHER INFORMATION: /note= "Amino acid 7 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
            (A) NAME/KEY: Modified-site
            (B) LOCATION: 14
            (D) OTHER INFORMATION: /note= "Amino acid 14 is
                gamma-carboxyglutamate (Gla)"

(ix) FEATURE:
            (A) NAME/KEY: Modified-site
            (B) LOCATION: 17
            (D) OTHER INFORMATION: /note= "Amino acid 17 has an
                amidated terminus"

(xi) SEQUENCE DESCRIPTION: SEQ ID NO:23:

Gly Glu Ser Xaa Leu Gln Xaa Asn Gln Xaa Leu Ile Arg Xaa Lys
1               5                   10                  15

Ser Asn (2) INFORMATION FOR SEQ ID NO:24:

(i) SEQUENCE CHARACTERISTICS:
            (A) LENGTH: 17 amino acids
            (B) TYPE: amino acid
            (D) TOPOLOGY: linear (ii) MOLECULE TYPE: protein (iii) HYPOTHETICAL: NO (ix) FEATURE:
            (A) NAME/KEY: Modified-site
            (B) LOCATION: 3
            (D) OTHER INFORMATION: /note= "Amino acid 3 is
                phosphorylated"

(ix) FEATURE:
            (A) NAME/KEY: Modified-site
            (B) LOCATION: 4
            (D) OTHER INFORMATION: /note= "Amino acid 4 is
                gamma-carboxyglutamate (Gla)"

(ix) FEATURE:
            (A) NAME/KEY: Modified-site
            (B) LOCATION: 7
            (D) OTHER INFORMATION: /note= "Amino acid 7 is
                gamma-carboxyglutamate (Gla)"

(ix) FEATURE:
            (A) NAME/KEY: Modified-site
            (B) LOCATION: 10
            (D) OTHER INFORMATION: /note= "Amino acid 10 is
                gamma-carboxyglutamate (Gla)"

(ix) FEATURE:
            (A) NAME/KEY: Modified-site
            (B) LOCATION: 14
            (D) OTHER INFORMATION: /note= "Amino acid 14 is
                gamma-carboxyglutamate (Gla)"

(ix) FEATURE:
            (A) NAME/KEY: Modified-site
            (B) LOCATION: 17
            (D) OTHER INFORMATION: /note= "Amino acid 17 has an
                amidated terminus"

(xi) SEQUENCE DESCRIPTION: SEQ ID NO:24:

Gly Glu Ser Xaa Leu Gln Xaa Asn Gln Xaa Leu Ile Arg Xaa Lys
1               5                   10                  15

Ser Asn (2) INFORMATION FOR SEQ ID NO:25:

(i) SEQUENCE CHARACTERISTICS:

(A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 7
        (D) OTHER INFORMATION: /note= "Amino acid 7 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:25:

Gly Glu Tyr Xaa Leu Gln Xaa Asn Gln Xaa Leu Ile Arg Xaa Lys
1               5                   10                  15

Ser Asn (2) INFORMATION FOR SEQ ID NO:26:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 7
        (D) OTHER INFORMATION: /note= "Amino acid 7 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is

```
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:26:

Gly Glu Xaa Glu Leu Gln Xaa Asn Gln Xaa Leu Ile Arg Xaa Lys
 1               5                  10                  15

Ser Asn (2) INFORMATION FOR SEQ ID NO:27:

(i) SEQUENCE CHARACTERISTICS:
         (A) LENGTH: 17 amino acids
         (B) TYPE: amino acid
         (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 7
        (D) OTHER INFORMATION: /note= "Amino acid 7 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:27:

Gly Glu Xaa Ala Leu Gln Xaa Asn Gln Xaa Leu Ile Arg Xaa Lys
 1               5                  10                  15

Ser Asn (2) INFORMATION FOR SEQ ID NO:28:

(i) SEQUENCE CHARACTERISTICS:
         (A) LENGTH: 17 amino acids
         (B) TYPE: amino acid
         (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
```

```
              (D) OTHER INFORMATION: /note= "Amino acid 3 is
                   gamma-carboxyglutamate (Gla)"

(ix) FEATURE:
              (A) NAME/KEY: Modified-site
              (B) LOCATION: 7
              (D) OTHER INFORMATION: /note= "Amino acid 7 is
                   gamma-carboxyglutamate (Gla)"

(ix) FEATURE:
              (A) NAME/KEY: Modified-site
              (B) LOCATION: 10
              (D) OTHER INFORMATION: /note= "Amino acid 10 is
                   gamma-carboxyglutamate (Gla)"

(ix) FEATURE:
              (A) NAME/KEY: Modified-site
              (B) LOCATION: 14
              (D) OTHER INFORMATION: /note= "Amino acid 14 is
                   gamma-carboxyglutamate (Gla)"

(ix) FEATURE:
              (A) NAME/KEY: Modified-site
              (B) LOCATION: 17
              (D) OTHER INFORMATION: /note= "Amino acid 17 has an
                   amidated terminus"

(xi) SEQUENCE DESCRIPTION: SEQ ID NO:28:

Gly Glu Xaa Ser Leu Gln Xaa Asn Gln Xaa Leu Ile Arg Xaa Lys
 1               5                  10                  15

Ser Asn (2) INFORMATION FOR SEQ ID NO:29:

(i) SEQUENCE CHARACTERISTICS:
              (A) LENGTH: 17 amino acids
              (B) TYPE: amino acid
              (D) TOPOLOGY: linear (ii) MOLECULE TYPE: protein (iii) HYPOTHETICAL: NO (ix) FEATURE:
              (A) NAME/KEY: Modified-site
              (B) LOCATION: 3
              (D) OTHER INFORMATION: /note= "Amino acid 3 is
                   gamma-carboxyglutamate (Gla)"

(ix) FEATURE:
              (A) NAME/KEY: Modified-site
              (B) LOCATION: 4
              (D) OTHER INFORMATION: /note= "Amino acid 4 is
                   phosphorylated"

(ix) FEATURE:
              (A) NAME/KEY: Modified-site
              (B) LOCATION: 7
              (D) OTHER INFORMATION: /note= "Amino acid 7 is
                   gamma-carboxyglutamte (Gla)"

(ix) FEATURE:
              (A) NAME/KEY: Modified-site
              (B) LOCATION: 10
              (D) OTHER INFORMATION: /note= "Amino acid 10 is
                   gamma-carboxyglutamate (Gla)"

(ix) FEATURE:
              (A) NAME/KEY: Modified-site
              (B) LOCATION: 14
              (D) OTHER INFORMATION: /note= "Amino acid 14 is
                   gamma-carboxyglutamate (Gla)"

(ix) FEATURE:
              (A) NAME/KEY: Modified-site
              (B) LOCATION: 17
```

(D) OTHER INFORMATION: /note= "Amino acid 17 has an
                amidated terminus"

(xi) SEQUENCE DESCRIPTION: SEQ ID NO:29:

Gly Glu Xaa Ser Leu Gln Xaa Asn Gln Xaa Leu Ile Arg Xaa Lys
1               5                   10                  15

Ser Asn (2) INFORMATION FOR SEQ ID NO:30:

(i) SEQUENCE CHARACTERISTICS:
           (A) LENGTH: 17 amino acids
           (B) TYPE: amino acid
           (D) TOPOLOGY: linear (ii) MOLECULE TYPE: protein (iii) HYPOTHETICAL: NO (ix) FEATURE:
           (A) NAME/KEY: Modified-site
           (B) LOCATION: 3
           (D) OTHER INFORMATION: /note= "Amino acid 3 is
                gamma-carboxyglutamate (Gla)"

(ix) FEATURE:
           (A) NAME/KEY: Modified-site
           (B) LOCATION: 4
           (D) OTHER INFORMATION: /note= "Amino acid 4 is
                gamma-carboxyglutamate (Gla)"

(ix) FEATURE:
           (A) NAME/KEY: Modified-site
           (B) LOCATION: 7
           (D) OTHER INFORMATION: /note= "Amino acid 7 is
                gamma-carboxyglutamate (Gla)"

(ix) FEATURE:
           (A) NAME/KEY: Modified-site
           (B) LOCATION: 10
           (D) OTHER INFORMATION: /note= "Amino acid 10 is
                gamma-carboxyglutamate (Gla)"

(ix) FEATURE:
           (A) NAME/KEY: Modified-site
           (B) LOCATION: 14
           (D) OTHER INFORMATION: /note= "Amino acid 14 is
                gamma-carboxyglutamate (Gla)"

(ix) FEATURE:
           (A) NAME/KEY: Modified-site
           (B) LOCATION: 17
           (D) OTHER INFORMATION: /note= "Amino acid 17 has an
                amidated terminus"

(xi) SEQUENCE DESCRIPTION: SEQ ID NO:30:

Gly Glu Xaa Xaa Tyr Gln Xaa Asn Gln Xaa Leu Ile Arg Xaa Lys
1               5                   10                  15

Ser Asn (2) INFORMATION FOR SEQ ID NO:31:

(i) SEQUENCE CHARACTERISTICS:
           (A) LENGTH: 17 amino acids
           (B) TYPE: amino acid
           (D) TOPOLOGY: linear (ii) MOLECULE TYPE: protein (iii) HYPOTHETICAL: NO (ix) FEATURE:
           (A) NAME/KEY: Modified-site (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:31:

Gly Glu Xaa Xaa Leu Gln Tyr Asn Gln Xaa Leu Ile Arg Xaa Lys
1               5                   10                  15

Ser Asn (2) INFORMATION FOR SEQ ID NO:32:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:32:

```
Gly Glu Xaa Xaa Leu Gln Ala Asn Gln Xaa Leu Ile Arg Xaa Lys
1               5                   10                  15

Ser Asn
```

(2) INFORMATION FOR SEQ ID NO:33:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:33:

```
Gly Glu Xaa Xaa Leu Gln Ser Asn Gln Xaa Leu Ile Arg Xaa Lys
1               5                   10                  15

Ser Asn
```

(2) INFORMATION FOR SEQ ID NO:34:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:

```
          (A) NAME/KEY: Modified-site
          (B) LOCATION: 7
          (D) OTHER INFORMATION: /note= "Amino acid 7 is
              phosphorylated"

(ix) FEATURE:
          (A) NAME/KEY: Modified-site
          (B) LOCATION: 10
          (D) OTHER INFORMATION: /note= "Amino acid 10 is
              gamma-carboxyglutamate (Gla)"

(ix) FEATURE:
          (A) NAME/KEY: Modified-site
          (B) LOCATION: 14
          (D) OTHER INFORMATION: /note= "Amino acid 14 is
              gamma-carboxyglutamate (Gla)"

(ix) FEATURE:
          (A) NAME/KEY: Modified-site
          (B) LOCATION: 17
          (D) OTHER INFORMATION: /note= "Amino acid 17 has an
              amidated terminus"

(xi) SEQUENCE DESCRIPTION: SEQ ID NO:34:

Gly Glu Xaa Xaa Leu Gln Ser Asn Gln Xaa Leu Ile Arg Xaa Lys
1               5                   10                  15

Ser Asn (2) INFORMATION FOR SEQ ID NO:35:

(i) SEQUENCE CHARACTERISTICS:
          (A) LENGTH: 17 amino acids
          (B) TYPE: amino acid
          (D) TOPOLOGY: linear (ii) MOLECULE TYPE: protein (iii) HYPOTHETICAL: NO (ix) FEATURE:
          (A) NAME/KEY: Modified-site
          (B) LOCATION: 3
          (D) OTHER INFORMATION: /note= "Amino acid 3 is
              gamma-carboxyglutamate (Gla)"

(ix) FEATURE:
          (A) NAME/KEY: Modified-site
          (B) LOCATION: 4
          (D) OTHER INFORMATION: /note= "Amino acid 4 is
              gamma-carboxyglutamate (Gla)"

(ix) FEATURE:
          (A) NAME/KEY: Modified-site
          (B) LOCATION: 7
          (D) OTHER INFORMATION: /note= "Amino acid 7 is
              gamma-carboxyglutamate (Gla)"

(ix) FEATURE:
          (A) NAME/KEY: Modified-site
          (B) LOCATION: 14
          (D) OTHER INFORMATION: /note= "Amino acid 14 is
              gamma-carboxyglutamate (Gla)"

(ix) FEATURE:
          (A) NAME/KEY: Modified-site
          (B) LOCATION: 17
          (D) OTHER INFORMATION: /note= "Amino acid 17 has an
              amidated terminus"

(xi) SEQUENCE DESCRIPTION: SEQ ID NO:35:

Gly Glu Xaa Xaa Leu Gln Xaa Asn Gln Ala Leu Ile Arg Xaa Lys
1               5                   10                  15

Ser Asn
```

(2) INFORMATION FOR SEQ ID NO:36:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 7
        (D) OTHER INFORMATION: /note= "Amino acid 7 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:36:

```
Gly Glu Xaa Xaa Leu Gln Xaa Asn Gln Ser Leu Ile Arg Xaa Lys
1               5                   10                  15

Ser Asn
```

(2) INFORMATION FOR SEQ ID NO:37:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 7
        (D) OTHER INFORMATION: /note= "Amino acid 7 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            phosphorylated"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:37:

Gly Glu Xaa Xaa Leu Gln Xaa Asn Gln Ser Leu Ile Arg Xaa Lys
1               5                   10                  15

Ser Asn (2) INFORMATION FOR SEQ ID NO:38:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 7
        (D) OTHER INFORMATION: /note= "Amino acid 7 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:38:

Gly Glu Xaa Xaa Leu Gln Xaa Asn Gln Xaa Leu Ile Arg Ala Lys
1               5                   10                  15

Ser Asn (2) INFORMATION FOR SEQ ID NO:39:

(i) SEQUENCE CHARACTERISTICS:
        (A) LENGTH: 17 amino acids (B) TYPE: amino acid
            (D) TOPOLOGY: linear (ii) MOLECULE TYPE: protein (iii) HYPOTHETICAL: NO (ix) FEATURE:
            (A) NAME/KEY: Modified-site
            (B) LOCATION: 3
            (D) OTHER INFORMATION: /note= "Amino acid 3 is
                gamma-carboxyglutamate (Gla)"

(ix) FEATURE:
            (A) NAME/KEY: Modified-site
            (B) LOCATION: 4
            (D) OTHER INFORMATION: /note= "Amino acid 4 is
                gamma-carboxyglutamate (Gla)"

(ix) FEATURE:
            (A) NAME/KEY: Modified-site
            (B) LOCATION: 7
            (D) OTHER INFORMATION: /note= "Amino acid 7 is
                gamma-carboxyglutamate (Gla)"

(ix) FEATURE:
            (A) NAME/KEY: Modified-site
            (B) LOCATION: 10
            (D) OTHER INFORMATION: /note= "Amino acid 10 is
                gamma-carboxyglutamate (Gla)"

(ix) FEATURE:
            (A) NAME/KEY: Modified-site
            (B) LOCATION: 17
            (D) OTHER INFORMATION: /note= "Amino acid 17 has an
                amidated terminus"

(xi) SEQUENCE DESCRIPTION: SEQ ID NO:39:

Gly Glu Xaa Xaa Leu Gln Xaa Asn Gln Xaa Leu Ile Arg Ser Lys
1               5                   10                  15

Ser Asn (2) INFORMATION FOR SEQ ID NO:40:

(i) SEQUENCE CHARACTERISTICS:
            (A) LENGTH: 17 amino acids
            (B) TYPE: amino acid
            (D) TOPOLOGY: linear (ii) MOLECULE TYPE: protein (iii) HYPOTHETICAL: NO (ix) FEATURE:
            (A) NAME/KEY: Modified-site
            (B) LOCATION: 3
            (D) OTHER INFORMATION: /note= "Amino acid 3 is
                gamma-carboxyglutamate (Gla)"

(ix) FEATURE:
            (A) NAME/KEY: Modified-site
            (B) LOCATION: 4
            (D) OTHER INFORMATION: /note= "Amino acid 4 is
                gamma-carboxyglutamate (Gla)"

(ix) FEATURE:
            (A) NAME/KEY: Modified-site
            (B) LOCATION: 7
            (D) OTHER INFORMATION: /note= "Amino acid 7 is
                gamma-carboxyglutamate (Gla)"

(ix) FEATURE:
            (A) NAME/KEY: Modified-site
            (B) LOCATION: 10
            (D) OTHER INFORMATION: /note= "Amino acid 10 is
                gamma-carboxyglutamate (Gla)"

(ix) FEATURE:
            (A) NAME/KEY: Modified-site
            (B) LOCATION: 14
            (D) OTHER INFORMATION: /note= "Amino acid 14 is
                phosphorylated"

(ix) FEATURE:
            (A) NAME/KEY: Modified-site
            (B) LOCATION: 17
            (D) OTHER INFORMATION: /note= "Amino acid 17 has an
                amidated terminus"

(xi) SEQUENCE DESCRIPTION: SEQ ID NO:40:

Gly Glu Xaa Xaa Leu Gln Xaa Asn Gln Xaa Leu Ile Arg Ser Lys
1               5                  10                  15

Ser Asn (2) INFORMATION FOR SEQ ID NO:41:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:41:

Gly Glu Xaa Xaa Leu Gln Glu Asn Gln Glu Leu Ile Arg Glu Lys
1               5                  10                  15

Ser Asn (2) INFORMATION FOR SEQ ID NO:42:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:42:

Gly Glu Xaa Xaa Leu Gln Ala Asn Gln Ala Leu Ile Arg Ala Lys
1               5                  10                  15

Ser Asn (2) INFORMATION FOR SEQ ID NO:43:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 6
        (D) OTHER INFORMATION: /note= "Amino acid 6 has an
            amidated terminus"

(xi) SEQUENCE DESCRIPTION: SEQ ID NO:43:

Ile Arg Glu Ala Ser Asn
1               5

(2) INFORMATION FOR SEQ ID NO:44:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 6
        (D) OTHER INFORMATION: /note= "Amino acid 6 has an
            amidated terminus"

(xi) SEQUENCE DESCRIPTION: SEQ ID NO:44:

Ile Ala Glu Lys Ser Asn
1               5

(2) INFORMATION FOR SEQ ID NO:45:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 6
        (D) OTHER INFORMATION: /note= "Amino acid 6 has an
            amidated terminus"

(xi) SEQUENCE DESCRIPTION: SEQ ID NO:45:

Ile Ala Glu Ala Ser Asn
1               5

(2) INFORMATION FOR SEQ ID NO:46:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 6
        (D) OTHER INFORMATION: /note= "Amino acid 6 has an
            amidated terminus"

(xi) SEQUENCE DESCRIPTION: SEQ ID NO:46:

Ile Arg Xaa Lys Ser Asn
1               5

(2) INFORMATION FOR SEQ ID NO:47:

(i) SEQUENCE CHARACTERISTICS:
        (A) LENGTH: 5 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 5
        (D) OTHER INFORMATION: /note= "Amino acid 5 has an
            amidated terminus"

(xi) SEQUENCE DESCRIPTION: SEQ ID NO:47:

Arg Ser Xaa Asn Lys
1               5

(2) INFORMATION FOR SEQ ID NO:48:

(i) SEQUENCE CHARACTERISTICS:
        (A) LENGTH: 5 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is

```
               gamma-carboxyglutamate (Gla)"

(ix) FEATURE:
         (A) NAME/KEY: Modified-site
         (B) LOCATION: 5
         (D) OTHER INFORMATION: /note= "Amino acid 5 has an
             amidated terminus"

(xi) SEQUENCE DESCRIPTION: SEQ ID NO:48:

Arg Xaa Lys Ser Asn
1               5

(2) INFORMATION FOR SEQ ID NO:49:

(i) SEQUENCE CHARACTERISTICS:
        (A) LENGTH: 4 amino acids
        (B) TYPE: amino acid
        (D) TOPOLOGY: linear (ii) MOLECULE TYPE: protein (iii) HYPOTHETICAL: NO (ix) FEATURE:
         (A) NAME/KEY: Modified-site
         (B) LOCATION: 1
         (D) OTHER INFORMATION: /note= "Amino acid 1 is
             gamma-carboxyglutamate (Gla)"

(ix) FEATURE:
         (A) NAME/KEY: Modified-site
         (B) LOCATION: 4
         (D) OTHER INFORMATION: /note= "Amino acid 4 has an
             amidated terminus"

(xi) SEQUENCE DESCRIPTION: SEQ ID NO:49:

Xaa Lys Ser Asn
1

(2) INFORMATION FOR SEQ ID NO:50:

(i) SEQUENCE CHARACTERISTICS:
        (A) LENGTH: 4 amino acids
        (B) TYPE: amino acid
        (D) TOPOLOGY: linear (ii) MOLECULE TYPE: protein (iii) HYPOTHETICAL: NO (ix) FEATURE:
         (A) NAME/KEY: Modified-site
         (B) LOCATION: 3
         (D) OTHER INFORMATION: /note= "Amino acid 3 is
             gamma-carboxyglutamate (Gla)"

(ix) FEATURE:
         (A) NAME/KEY: Modified-site
         (B) LOCATION: 4
         (D) OTHER INFORMATION: /note= "Amino acid 4 has an
             amidated terminus"

(xi) SEQUENCE DESCRIPTION: SEQ ID NO:50:

Ile Arg Xaa Lys
1

(2) INFORMATION FOR SEQ ID NO:51:

(i) SEQUENCE CHARACTERISTICS:
        (A) LENGTH: 3 amino acids
        (B) TYPE: amino acid
        (D) TOPOLOGY: linear
```

```
        (ii) MOLECULE TYPE: protein (iii) HYPOTHETICAL: NO (ix) FEATURE:
             (A) NAME/KEY: Modified-site
             (B) LOCATION: 3
             (D) OTHER INFORMATION: /note= "Amino acid 3 has an
                 amidated terminus"

(xi) SEQUENCE DESCRIPTION: SEQ ID NO:51:

Lys Ser Asn
1

(2) INFORMATION FOR SEQ ID NO:52:

(i) SEQUENCE CHARACTERISTICS:
             (A) LENGTH: 5 amino acids
             (B) TYPE: amino acid
             (D) TOPOLOGY: linear (ii) MOLECULE TYPE: protein (iii) HYPOTHETICAL: NO (ix) FEATURE:
             (A) NAME/KEY: Modified-site
             (B) LOCATION: 3
             (D) OTHER INFORMATION: /note= "Amino acid 3 is
                 gamma-carboxyglutamate (Gla)"

(ix) FEATURE:
             (A) NAME/KEY: Modified-site
             (B) LOCATION: 4
             (D) OTHER INFORMATION: /note= "Amino acid 4 is
                 gamma-carboxyglutamate (Gla)"

(ix) FEATURE:
             (A) NAME/KEY: Modified-site
             (B) LOCATION: 5
             (D) OTHER INFORMATION: /note= "Amino acid 5 has an
                 amidated terminus"

(xi) SEQUENCE DESCRIPTION: SEQ ID NO:52:

Gly Glu Xaa Xaa Leu
1               5

(2) INFORMATION FOR SEQ ID NO:53:

(i) SEQUENCE CHARACTERISTICS:
             (A) LENGTH: 17 amino acids
             (B) TYPE: amino acid
             (D) TOPOLOGY: linear (ii) MOLECULE TYPE: protein (iii) HYPOTHETICAL: NO (ix) FEATURE:
             (A) NAME/KEY: Modified-site
             (B) LOCATION: 3
             (D) OTHER INFORMATION: /note= "Amino acid 3 is
                 gamma-carboxyglutamate (Gla)"

(ix) FEATURE:
             (A) NAME/KEY: Modified-site
             (B) LOCATION: 4
             (D) OTHER INFORMATION: /note= "Amino acid 4 is
                 gamma-carboxyglutamate (Gla)"

(ix) FEATURE:
             (A) NAME/KEY: Modified-site
             (B) LOCATION: 7
             (D) OTHER INFORMATION: /note= "Amino acid 7 is
                 iodinated (cold)"
```

```
    (ix) FEATURE:
          (A) NAME/KEY: Modified-site
          (B) LOCATION: 10
          (D) OTHER INFORMATION: /note= "Amino acid 10 is
              gamma-carboxyglutamate (Gla)"

(ix) FEATURE:
          (A) NAME/KEY: Modified-site
          (B) LOCATION: 14
          (D) OTHER INFORMATION: /note= "Amino acid 14 is
              gamma-carboxyglutamate (Gla)"

(ix) FEATURE:
          (A) NAME/KEY: Modified-site
          (B) LOCATION: 17
          (D) OTHER INFORMATION: /note= "Amino acid 17 has an
              amidated terminus"

(xi) SEQUENCE DESCRIPTION: SEQ ID NO:53:

Gly Glu Xaa Xaa Leu Gln Tyr Asn Gln Xaa Leu Ile Arg Xaa Lys
1               5                  10                  15

Ser Asn (2) INFORMATION FOR SEQ ID NO:54:

(i) SEQUENCE CHARACTERISTICS:
          (A) LENGTH: 17 amino acids
          (B) TYPE: amino acid
          (D) TOPOLOGY: linear (ii) MOLECULE TYPE: protein (iii) HYPOTHETICAL: NO (ix) FEATURE:
          (A) NAME/KEY: Modified-site
          (B) LOCATION: 3
          (D) OTHER INFORMATION: /note= "Amino acid 3 is
              gamma-carboxyglutamate (Gla)"

(ix) FEATURE:
          (A) NAME/KEY: Modified-site
          (B) LOCATION: 4
          (D) OTHER INFORMATION: /note= "Amino acid 4 is
              gamma-carboxyglutamate (Gla)"

(ix) FEATURE:
          (A) NAME/KEY: Modified-site
          (B) LOCATION: 7
          (D) OTHER INFORMATION: /note= "Amino acid 7 is
              di-iodinated (cold)"

(ix) FEATURE:
          (A) NAME/KEY: Modified-site
          (B) LOCATION: 10
          (D) OTHER INFORMATION: /note= "Amino acid 10 is
              gamma-carboxyglutamate (Gla)"

(ix) FEATURE:
          (A) NAME/KEY: Modified-site
          (B) LOCATION: 14
          (D) OTHER INFORMATION: /note= "Amino acid 14 is
              gamma-carboxyglutamate (Gla)"

(ix) FEATURE:
          (A) NAME/KEY: Modified-site
          (B) LOCATION: 17
          (D) OTHER INFORMATION: /note= "Amino acid 17 has an
              amidated terminus"

(xi) SEQUENCE DESCRIPTION: SEQ ID NO:54:

Gly Glu Xaa Xaa Leu Gln Tyr Asn Gln Xaa Leu Ile Arg Xaa Lys
1               5                  10                  15
```

Ser Asn (2) INFORMATION FOR SEQ ID NO:55:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:55:

Gly Glu Xaa Xaa Leu Gln Ser Asn Val Ser Gln Ile Arg Ala Lys
1               5                   10                  15

Ser Asn (2) INFORMATION FOR SEQ ID NO:56:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:56:

Gly Glu Xaa Xaa Leu Gln Ala Ala Leu Ala Leu Ile Arg Ala Lys
1               5                   10                  15

Ser Asn (2) INFORMATION FOR SEQ ID NO:57:

```
    (i) SEQUENCE CHARACTERISTICS:
        (A) LENGTH: 9 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 6
        (D) OTHER INFORMATION: /note= "Amino acid 6 is
            gamma-carboxyglutamate (Gla)"

(ix) FEATURE:
        (A) NAME/KEY: Modified-site
        (B) LOCATION: 9
        (D) OTHER INFORMATION: /note= "Amino acid 9 has an
            amidated terminus"

(xi) SEQUENCE DESCRIPTION: SEQ ID NO:57:

Gly Glu Xaa Xaa Leu Xaa Lys Ser Asn
1               5

(2) INFORMATION FOR SEQ ID NO:58:

(i) SEQUENCE CHARACTERISTICS:
        (A) LENGTH: 11 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 8
        (D) OTHER INFORMATION: /note= "Amino acid 8 is
            gamma-carboxyglutamate (Gla)"

(ix) FEATURE:
        (A) NAME/KEY: Modified-site
        (B) LOCATION: 11
        (D) OTHER INFORMATION: /note= "Amino acid 11 has an
            amidated terminus"

(xi) SEQUENCE DESCRIPTION: SEQ ID NO:58:

Gly Glu Xaa Xaa Leu Gly Gly Xaa Lys Ser Asn
1               5                   10
```

(2) INFORMATION FOR SEQ ID NO:59:

(i) SEQUENCE CHARACTERISTICS:
        (A) LENGTH: 13 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 10
        (D) OTHER INFORMATION: /note= "Amino acid 10 is
            gamma-carboxyglutamate (Gla)"

(ix) FEATURE:
        (A) NAME/KEY: Modified-site
        (B) LOCATION: 13
        (D) OTHER INFORMATION: /note= "Amino acid 13 has an
            amidated terminus"

(xi) SEQUENCE DESCRIPTION: SEQ ID NO:59:

```
Gly Glu Xaa Xaa Leu Gly Gly Gly Gly Xaa Lys Ser Asn
1               5                   10
```

(2) INFORMATION FOR SEQ ID NO:60:

(i) SEQUENCE CHARACTERISTICS:
        (A) LENGTH: 11 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 8
        (D) OTHER INFORMATION: /note= "Amino acid 8 is
            gamma-carboxyglutamate (Gla)"

(ix) FEATURE:
        (A) NAME/KEY: Modified-site
        (B) LOCATION: 11
        (D) OTHER INFORMATION: /note= "Amino acid 11 has an
            amidated terminus"

(xi) SEQUENCE DESCRIPTION: SEQ ID NO:60:

```
Gly Glu Xaa Xaa Leu Ala Ala Xaa Lys Ser Asn
1               5                   10
```

(2) INFORMATION FOR SEQ ID NO:61:

(i) SEQUENCE CHARACTERISTICS:
        (A) LENGTH: 12 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 9
        (D) OTHER INFORMATION: /note= "Amino acid 9 is
            gamma-carboxyglutamate (Gla)"

(ix) FEATURE:
        (A) NAME/KEY: Modified-site
        (B) LOCATION: 12
        (D) OTHER INFORMATION: /note= "Amino acid 12 has an
            amidated terminus"

(xi) SEQUENCE DESCRIPTION: SEQ ID NO:61:

```
Gly Glu Xaa Xaa Leu Ala Ala Ala Xaa Lys Ser Asn
1               5                   10
```

(2) INFORMATION FOR SEQ ID NO:62:

(i) SEQUENCE CHARACTERISTICS:
        (A) LENGTH: 15 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 12
        (D) OTHER INFORMATION: /note= "Amino acid 12 is
            gamma-carboxyglutamate (Gla)"

(ix) FEATURE:
        (A) NAME/KEY: Modified-site
        (B) LOCATION: 15
        (D) OTHER INFORMATION: /note= "Amino acid 15 has an
            amidated terminus"

(xi) SEQUENCE DESCRIPTION: SEQ ID NO:62:

Gly Glu Xaa Xaa Leu Gln Ala Ala Ala Ala Ala Xaa Lys Ser Asn
1               5                   10                  15

(2) INFORMATION FOR SEQ ID NO:63:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 14
        (D) OTHER INFORMATION: /note= "Amino acid 14 is
            gamma-carboxyglutamate (Gla)"

(ix) FEATURE:
        (A) NAME/KEY: Modified-site
        (B) LOCATION: 17
        (D) OTHER INFORMATION: /note= "Amino acid 17 has an
            amidated terminus"

(xi) SEQUENCE DESCRIPTION: SEQ ID NO:63:

Gly Glu Xaa Xaa Leu Gln Ala Ala Ala Ala Ala Ala Xaa Lys
1               5                   10                  15

Ser Asn (2) INFORMATION FOR SEQ ID NO:64:

(i) SEQUENCE CHARACTERISTICS:
        (A) LENGTH: 11 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Amino acid 3 is
            gamma-carboxyglutamate (Gla)"

(ix) FEATURE:
        (A) NAME/KEY: Modified-site
        (B) LOCATION: 4
        (D) OTHER INFORMATION: /note= "Amino acid 4 is
            gamma-carboxyglutamate (Gla)"

(ix) FEATURE:
        (A) NAME/KEY: Modified-site
        (B) LOCATION: 6
        (D) OTHER INFORMATION: /note= "Amino acid 6 is
            amino isibutryic acid"

-continued

```
    (ix) FEATURE:
         (A) NAME/KEY: Modified-site
         (B) LOCATION: 7
         (D) OTHER INFORMATION: /note= "Amino acid 7 is
             amino isibutryic acid"

(ix) FEATURE:
         (A) NAME/KEY: Modified-site
         (B) LOCATION: 8
         (D) OTHER INFORMATION: /note= "Amino acid 8 is
             gamma-carboxyglutamate (Gla)"

(ix) FEATURE:
         (A) NAME/KEY: Modified-site
         (B) LOCATION: 11
         (D) OTHER INFORMATION: /note= "Amino acid 11 has an
             amidated terminus"

(xi) SEQUENCE DESCRIPTION: SEQ ID NO:64:

Gly Glu Xaa Xaa Leu Xaa Xaa Xaa Lys Ser Asn
1               5                   10

(2) INFORMATION FOR SEQ ID NO:65:

(i) SEQUENCE CHARACTERISTICS:
        (A) LENGTH: 5 amino acids
        (B) TYPE: amino acid
        (D) TOPOLOGY: linear (ii) MOLECULE TYPE: protein (iii) HYPOTHETICAL: NO (ix) FEATURE:
         (A) NAME/KEY: Modified-site
         (B) LOCATION: 3
         (D) OTHER INFORMATION: /note= "Amino acid 3 is
             gamma-carboxyglutamate (Gla)"

(ix) FEATURE:
         (A) NAME/KEY: Modified-site
         (B) LOCATION: 4
         (D) OTHER INFORMATION: /note= "Amino acid 4 is
             gamma-carboxyglutamate (Gla)"

(ix) FEATURE:
         (A) NAME/KEY: Modified-site
         (B) LOCATION: 5
         (D) OTHER INFORMATION: /note= "Amino acid 5 is cyclic
             and has an amidated terminus"

(xi) SEQUENCE DESCRIPTION: SEQ ID NO:65:

Gly Glu Xaa Xaa Leu
1               5
```